(12) United States Patent
Her et al.

(10) Patent No.: US 9,988,611 B2
(45) Date of Patent: Jun. 5, 2018

(54) PROTEIN INHIBITORS TO COMPLEMENT AND VEGF PATHWAYS AND METHODS OF USE THEREOF

(71) Applicants: AP Biosciences, Inc., Taipei (TW); Innovent Biologies, Inc., George Town, Grand Cayman (KY)

(72) Inventors: Jeng-Horng Her, Sunnyvale, CA (US); Huang-Tsu Chen, Cupertino, CA (US)

(73) Assignees: AP Biosciences, Inc., Taipei (TW); Innovent Biologics, Inc., George Town, Grand Cayman (KY)

( * ) Notice: Subject to any disclaimer, the term of this patent is extended or adjusted under 35 U.S.C. 154(b) by 100 days.

(21) Appl. No.: 14/362,109

(22) PCT Filed: Nov. 30, 2012

(86) PCT No.: PCT/US2012/067489
§ 371 (c)(1),
(2) Date: May 30, 2014

(87) PCT Pub. No.: WO2013/082563
PCT Pub. Date: Jun. 6, 2013

(65) Prior Publication Data
US 2015/0079084 A1    Mar. 19, 2015

Related U.S. Application Data

(60) Provisional application No. 61/629,932, filed on Dec. 1, 2011.

(51) Int. Cl.
| | | |
|---|---|---|
| C07K 14/435 | (2006.01) | |
| C12N 9/12 | (2006.01) | |
| C07K 14/71 | (2006.01) | |
| C07K 14/47 | (2006.01) | |
| C07K 14/705 | (2006.01) | |
| C07K 16/00 | (2006.01) | |
| A61K 38/00 | (2006.01) | |

(52) U.S. Cl.
CPC .......... *C12N 9/1205* (2013.01); *C07K 14/472* (2013.01); *C07K 14/70596* (2013.01); *C07K 14/71* (2013.01); *C07K 16/00* (2013.01); *A61K 38/00* (2013.01); *C07K 2317/52* (2013.01); *C07K 2319/00* (2013.01); *C07K 2319/02* (2013.01); *C07K 2319/30* (2013.01); *C07K 2319/70* (2013.01); *C12Y 207/01112* (2013.01)

(58) Field of Classification Search
None
See application file for complete search history.

(56) References Cited

U.S. PATENT DOCUMENTS

| | | |
|---|---|---|
| RE30,985 E | 6/1982 | Cartaya |
| 4,419,446 A | 12/1983 | Howley et al. |
| 4,560,655 A | 12/1985 | Baker |
| 4,601,978 A | 7/1986 | Karin |
| 4,657,760 A | 4/1987 | Kung et al. |
| 4,657,866 A | 4/1987 | Kumar |
| 4,767,704 A | 8/1988 | Cleveland et al. |
| 4,927,762 A | 5/1990 | Darfler |
| 5,122,469 A | 6/1992 | Mather et al. |
| 5,206,344 A | 4/1993 | Katre et al. |
| 5,225,212 A | 7/1993 | Martin et al. |
| 5,648,237 A | 7/1997 | Carter |
| 5,789,199 A | 8/1998 | Joly et al. |
| 5,840,523 A | 11/1998 | Simmons et al. |
| 6,713,606 B1 | 3/2004 | Smith et al. |
| 7,531,173 B2 | 5/2009 | Wiegand et al. |
| 2006/0134105 A1 | 6/2006 | Lazar et al. |
| 2010/0150926 A1 | 6/2010 | Jung et al. |
| 2010/0249382 A1 | 9/2010 | Desjarlais et al. |
| 2015/0004166 A1* | 1/2015 | Baehner ................ C07K 16/22 424/136.1 |

FOREIGN PATENT DOCUMENTS

| | | |
|---|---|---|
| CN | 1369009 A | 9/2002 |
| DE | 266710 A3 | 4/1989 |
| EP | 0073657 B1 | 12/1990 |
| EP | 0402226 A1 | 12/1990 |
| EP | 0183070 B1 | 10/1991 |
| EP | 0244234 B2 | 11/2001 |
| JP | 2006-512325 A | 4/2006 |
| JP | 2009-511496 A | 3/2009 |
| JP | 2009-523821 A | 6/2009 |
| JP | 2009-540831 A | 11/2009 |
| WO | 1987/000195 A1 | 1/1987 |
| WO | 1990/003430 A1 | 4/1990 |
| WO | 1990/013646 A1 | 11/1990 |
| WO | 1994/011026 A2 | 5/1994 |
| WO | WO-00/75319 A1 | 12/2000 |
| WO | 2004/045520 A2 | 6/2004 |
| WO | 2007/044668 A2 | 4/2007 |
| WO | 2007/084765 A2 | 7/2007 |
| WO | 2007/149567 A2 | 12/2007 |

OTHER PUBLICATIONS

Altschuh et al., "Determination of Kinetic Constants for the Interaction between a Monoclonal Antibody and Peptides Using Surface Plasmon Resonance", Biochemistry, vol. 31, No. 27, 1992, pp. 6298-6304.

Barnes et al., "Methods for Growth of Cultured Cells in Serum-Free Medium", Analytical Biochemistry, vol. 102, 1980, pp. 255-270.

Bird, Alan, C., "Therapeutic Targets in Age-Related Macular Disease", The Journal of Clinical Investigation, vol. 120, No. 9, Sep. 2010, pp. 3033-3041.

Bonifati et al., "Role of Complement in Neurodegeneration and Neuroinflammation", Molecular Immunology, vol. 44, 2007, pp. 999-1010.

(Continued)

Primary Examiner — Michael Pak
(74) Attorney, Agent, or Firm — Morrison & Foerster LLP

(57) ABSTRACT

The invention provides bispecific fusion proteins that inhibit activation of complement pathway and vascular endothelial growth factor (VEGF) pathway and methods for using these fusion proteins.

41 Claims, 8 Drawing Sheets

(56) References Cited

OTHER PUBLICATIONS

Carter et al., "High Level *Escherichia coli* Expression and Production of a Bivalent Humanized Antibody Fragment", Biotechnology, vol. 10, Feb. 1992, pp. 163-167.
Cunningham et al., "High-Resolution Epitope Mapping of hGH-receptor Interactions by Alanine-Scanning Mutagenesis", Science, vol. 244, Jun. 2, 1989, pp. 1081-1085.
Ehrnthaller et al., "New Insights of an Old Defense System: Structure, Function, and Clinical Relevance of the Complement System", Molecular Medicine, vol. 17, No. 3-4, Mar.-Apr. 2011, pp. 317-329.
Emerson et al., "Current and Emerging Therapies for the Treatment of Age-Related Macular Degeneration", Clinical Ophthalmology, vol. 2, No. 2, 2008, pp. 377-388.
Ferrara, Napoleone, "Vascular Endothelial Growth Factor: Basic Science and Clinical Progress", Endocrine Reviews, vol. 25, No. 4, Aug. 2004, pp. 581-611.
Fleer et al., "Stable Multicopy Vectors for High-Level Secretion of Recombinant Human Serum Albumin by Kluyveromyces Yeasts", Biotechnology, vol. 9, Oct. 1991, pp. 968-975.
Frampton, James E., "Aflibercept for Intravitreal Injection", Drugs Aging, vol. 29, Oct. 2012, pp. 839-846.
Gehrs et al., "Complement, Age-Related Macular Degeneration and a Vision of the Future", Arch. Ophthalmology, vol. 128, No. 3, Mar. 2010, pp. 349-358.
Gerngross, Tillman U., "Advances in the Production of Human Therapeutic Proteins in Yeasts and Filamentous Fungi", Nature Biotechnology, vol. 22, No. 11, Nov. 2004, pp. 1409-1414.
Graham et al., "Characteristics of a Human Cell Line Transformed by DNA from Human Adenovirus Type 5", Journal of General Virology, vol. 36, No. 1, Jul. 1977, pp. 59-72.
Guo et al., "Role of C5a in Inflammatory Responses", Annual Review of Immunology, vol. 23, 2005, pp. 821-852.
Ham et al., "Media and Growth Requirements", Methods in Enzymology, vol. LVIII, 1979, pp. 44-93.
Hein, Jotun, "Unified Approach to Alignment and Phylogenies", Methods in Enzymology, vol. 183, 1990, pp. 626-645.
Higgins et al., "CLUSTAL: A Package for Performing Multiple Sequence Alignment on a Microcomputer", Gene, vol. 73, 1988, pp. 237-244.
Hodgson et al., "The Synthesis of Peptides and Proteins Containing Non-Natural Amino Acids", Chemical Society Reviews, vol. 33, 2004, pp. 422-430.
Holash et al., "VEGF-Trap: A VEGF Blocker with Potent Antitumor Effects", PNAS, vol. 99, No. 17, Aug. 20, 2002, pp. 11393-11398.
Issa et al., "The Significance of the Complement System for the Pathogenesis of Age-Related Macular Degeneration—Current Evidence and Translation into Clinical Application", Graefes Arch Clin Exp Ophthalmol, vol. 249, 2011, pp. 163-174.
Jones, Elizabeth W., "Proteinase Mutants of *Saccharomyces cerevisiae*", Genetics, vol. 85, Jan. 1977, pp. 23-33.
Kontermann, Roland, "Therapeutic Proteins: Strategies to Modulate Their Plasma Half-Lives", Wiley-Blackwell, 2012, 360 pages.
Krych-Goldberg et al., "Decay Accelerating Activity of Complement Receptor Type 1 (CD35): Two Active Sites Are Required for Dissociating C5 Convertases", The Journal of Biological Chemistry, vol. 274, No. 44, Oct. 29, 1999, pp. 31160-31168.
Krych-Goldberg et al., "Structure-Function Relationships of Complement Receptor Type 1", Immunological Reviews, vol. 180, 2001, pp. 112-122.
Langer, Robert, "New Methods of Drug Delivery", Science, vol. 249, Sep. 28, 1990, pp. 1527-1533.
Li et al., "Optimization of Humanized IgGs in Glycoengineered Pichia Pastoris", Nature Biotechnology, vol. 24, No. 2, Feb. 2006, pp. 210-215.
Lichtlen et al., "Relative Contribution of VEGF and TNF-α in the Cynomolgus Laser-Induced CNV Model: Comparing the Efficacy of Bevacizumab, Adalimumab, and ESBA105", Investigative Ophthalmology & Visual Science, vol. 51, No. 9, Sep. 2010, pp. 4738-4745.
Lindmark et al., "Binding of Immunoglobulins to Protein A and Immunoglobulin Levels in Mammalian Sera", Journal of Immunological Methods, vol. 62, 1983, pp. 1-13.
Liu et al., "Relationship between Complement Membrane Attack Complex, Chemokine (C-C Motif) Ligand 2 (CCL2) and Vascular Endothelial Growth Factor in Mouse Model of Laser-induced Choroidal Neovascularization", The Journal of Biological Chemistry, vol. 286, No. 23, Jun. 10, 2011, pp. 20991-21001.
Makrides, Savvas C., "Therapeutic Inhibition of the Complement System", Pharmacological Reviews, vol. 50, No. 1, 1998, pp. 59-87.
Manderson et al., "The Role of Complement in the Development of Systemic Lupus Erythematosus", Annual Review of Immunology, vol. 22, (First posted online on Nov. 10, 2003), 2004, pp. 431-456.
Markiewski et al., "The Role of Complement in Inflammatory Diseases From Behind the Scenes into the Spotlight", The American Journal of Pathology, vol. 171, No. 3, Sep. 2007, pp. 715-727.
Mather et al., "Culture of Testicular Cells in Hormone-Supplemented Serum-Free Medium", Annals of the New York Academy of Sciences, Testicular Cell Culture, 1982, pp. 44-68.
Mather, Jennie P., "Establishment and Characterization of Two Distinct Mouse Testicular Epithelial Cell Lines", Biology of Reproduction, vol. 23, 1980, pp. 243-252.
Mollnes et al., "Strategies of Therapeutic Complement Inhibition", Molecular Immunology, vol. 43, 2006, pp. 107-121.
Mordenti et al., "The Use of Interspecies Scaling in Toxicokinetics", Toxicokinetics and New Drug Development, 1989, pp. 42-96.
Nork et al., "Prevention of Experimental Choroidal Neovascularization and Resolution of Active Lesions by VEGF Trap in Nonhuman Primates", Arch. Ophthalmol., vol. 129, No. 8, Aug. 2011, pp. 1042-1052.
Ohr et al., "Intravitreal Aflibercept Injection for Neovascular (Wet) Age-Related Macular Degeneration", Expert Opinion on Pharmacotherapy, vol. 13, No. 4, 2012, pp. 585-591.
International Preliminary Report on Patentability received for PCT Patent Application No. PCT/US2012/067489 dated Jun. 12, 2014, 6 pages.
International Search Report and Written Opinion received for PCT Patent Application No. PCT/US2012/067489 dated Feb. 11, 2013, 7 pages.
Perry et al., "Phase I Safety Trial of Soluble Complement Receptor Type I (TP 10) in Acute Myocardial Infarction", Journal of the American College of Cardiology, Feb. 1998, p. 411A (1161-152).
Reyes et al., "Expression of Human p-Interferon cDNA Under the Control of a Thymidine Kinase Promoter from Herpes Simplex Virus", Nature, vol. 297, Jun. 17, 1982, pp. 598-601.
Ricklin et al., "Complement-Targeted Therapeutics", Nature Biotechnology, vol. 25, No. 11, Nov. 2007, pp. 1265-1275.
Rohrer et al., "A Targeted Inhibitor of the Alternative Complement Pathway Reduces Angiogenesis in a Mouse Model of Age-Related Macular Degeneration", Investigative Ophthalmology & Visual Science, vol. 50, No. 7, Jul. 2009, pp. 3056-3064.
Sandberg et al., "New Chemical Descriptors Relevant for the Design of Biologically Active Peptides. A Multivariate Characterization of 87 Amino Acids", Journal of Medicinal Chemistry, vol. 41, No. 14, 1998, pp. 2481-2491.
Scesney et al., "A Soluble Deletion Mutant of the Human Complement Receptor Type 1, Which Lacks the C4b Binding Site, is a Selective Inhibitor of the Alternative Complement Pathway", European Journal of Immunology, vol. 26, 1996, pp. 1729-1735.
Stinchcomb et al., "Isolation and Characterisation of a Yeast Chromosomal Replicator", Nature, vol. 282, Nov. 1, 1979, pp. 39-43.
Sullivan et al., "The Vegf Family in Cancer and Antibody-Based Strategies for Their Inhibition", mAbs, Landes Bioscience, vol. 2, No. 2 Mar./Apr. 2010, pp. 165-175.
Teng et al., "Clinical Applications of VEGF-Trap (Aflibercept) in Cancer Treatment", J. Chin. Med. Assoc. vol. 73, No. 9, Sep. 2010, pp. 449-456.
Urlaub et al., "Isolation of Chinese Hamster Cell Mutants Deficient in Dihydrofolate Reductase Activity", Proc. Natl. Acad. Sci., vol. 77, No. 7, Jul. 1980, pp. 4216-4220.

(56) References Cited

OTHER PUBLICATIONS

Van Den Berg et al., "Kluyveromyces as a Host for Heterologous Gene Expression: Expression and Secretion of Prochymosin", Bio/Technology, vol. 8, Feb. 1990, pp. 135-139.
Wagner et al., "Therapeutic Potential of Complement Modulation", Nature Reviews Drug Discovery, vol. 9, Jan. 2010, pp. 43-56.
Xie et al., "Adding Amino Acids to the Genetic Repertoire", Current Opinion in Chemical Biology, vol. 9, 2005, pp. 548-554.
Yaniv, Moshe, "Enhancing Elements for Activation of Eukaryotic Promoters", Nature, vol. 297, May 6, 1982, pp. 17-18.
Yazaki et al., "Expression of Recombinant Antibodies in Mammalian Cell Lines", Methods in Molecular Biology, vol. 248, 2004, pp. 255-268.
Yu et al., "Soluble Vascular Endothelial Growth Factor Decoy Receptor FP3 Exerts Potent Antiangiogenic Effects", Molecular Therapy, vol. 20, No. 5, May 2012, pp. 938-947.
Zamora et al., "Complement Inhibition Attenuates Human Lung Transplant Reperfusion Injury*: A Multicenter Trial", Chest, vol. 116, No. Suppl_1, Jul. 1999, 1 page.
Zimmerman et al., "Phase I Trial of the Recombinant Soluble Complement Receptor 1 in Acute Lung Injury and Acute Respiratory Distress Syndrome", Critical Care Medicine, vol. 28, No. 9, 2000, pp. 3149-3154.
Costabile, Maurizio, "Measuring the 50% Haemolytic Complement (CH50) Activity of Serum", Journal of Visualized Experiments, vol. 37, 2010, pp. 1-3.
Bora et al., "CD59, a Complement Regulatory Protein, Controls Choroidal Neovascularization in a Mouse Model of Wet-Type Age-Related Macular Degeneration", The Journal of Immunology, vol. 178, No. 3, Feb. 2007, pp. 1783-1790.
Rohrer et al., "The Alternative Pathway is required, but not alone Sufficient, for Retinal Pathology in Mouse Laser-Induced Choroidal Neovascularization", Molecular Immunology, vol. 48, No. 6-7, Mar. 2011, 18 pages.
Smailhodzic, et al., "Risk Alleles in CFH and ARMS2 Are Independently Associated with Systemic Complement Activation in Age-related Macular Degeneration", Ophthalmology, vol. 119, No. 2, Feb. 2012, pp. 339.346.
Meissner et al., "Suppression of VEGFR2 Expression in Human Endothelial Cells by Dimethylfumarate Treatment: Evidence for Anti-Angiogenic Action", Journal of Investigative Dermatology, vol. 131, 2011, pp. 1356-1364.
Pio, Ruben ,"The Role of Complement in Tumor Growth", Adv Exp Med Biol., vol. 772, 2014, pp. 229-262.
Poor et al., "Inhibition of Angiogenesis in a Murine Laser-Induced Choroidal Neovascularization Model", Investigative Ophthalmology & Visual Science, vol. 48, 2007, p. 3429 (Abstract Only).
Szent-Gyorgi, Albert, "Life's Blood: Angiogenesis in Health and Disease", FASEB, 2010, pp. 1-17.
Kumar, P. et al. (Aug. 2008). Clinical Internal Medicine, Err' Edition, Peking University Medical Press, p. 1165, total 9 pp. with English Translation. X.
Liu, X. et al. (Apr. 2010). Cellular and Molecular Basis of Ocular Diseases, Science Press, Beijing, pp. 248-249, total 16 pp. with English Translation. X.
Song, H. et al. (Sep. 2009). Complementolocty, Science Press, Beiji pp. 248-249, total 12 pp. with English Translation. X.

\* cited by examiner

| Test article | Pre-dose | 14-day post dose |
|---|---|---|
| A) Vehicle control (PBS) |  |  |
| B) ACVP-1 (0.5 mg/eye) |  |  |
| C) VID (0.5 mg/eye) |  |  |
| D) CID (0.5 mg/eye) |  |  | ns and cell membrane proteins. Activation of the complement leads to a series of protease activation cascade triggering release of cytokines and amplification of the activation cascade. The end result of the complement activation is activation of the cell-killing membrane attack complex (MAC), inflammation caused by anaphylatoxins C3a and C5a, and opsonization of pathogens. The MAC is essential for eliminating invading pathogens and damaged, necrotic, and apoptotic cells.

SEQUENCE LISTING

<160> NUMBER OF SEQ ID NOS: 44

<210> SEQ ID NO 1
<211> LENGTH: 192
<212> TYPE: PRT
<213> ORGANISM: Homo sapiens

<400> SEQUENCE: 1

Gln Cys Asn Ala Pro Glu Trp Leu Pro Phe Ala Arg Pro Thr Asn Leu
 1               5                  10                  15

Thr Asp Glu Phe Glu Phe Pro Ile Gly Thr Tyr Leu Asn Tyr Glu Cys
            20                  25                  30

Arg Pro Gly Tyr Ser Gly Arg Pro Phe Ser Ile Ile Cys Leu Lys Asn
        35                  40                  45

Ser Val Trp Thr Gly Ala Lys Asp Arg Cys Arg Arg Lys Ser Cys Arg

```
                50                  55                  60
Asn Pro Pro Asp Pro Val Asn Gly Met Val His Val Ile Lys Gly Ile
 65                  70                  75                  80

Gln Phe Gly Ser Gln Ile Lys Tyr Ser Cys Thr Lys Gly Tyr Arg Leu
                 85                  90                  95

Ile Gly Ser Ser Ser Ala Thr Cys Ile Ile Ser Gly Asp Thr Val Ile
                100                 105                 110

Trp Asp Asn Glu Thr Pro Ile Cys Asp Arg Ile Pro Cys Gly Leu Pro
                115                 120                 125

Pro Thr Ile Thr Asn Gly Asp Phe Ile Ser Thr Asn Arg Glu Asn Phe
            130                 135                 140

His Tyr Gly Ser Val Val Thr Tyr Arg Cys Asn Pro Gly Ser Gly Gly
145                 150                 155                 160

Arg Lys Val Phe Glu Leu Val Gly Glu Pro Ser Ile Tyr Cys Thr Ser
                165                 170                 175

Asn Asp Asp Gln Val Gly Ile Trp Ser Gly Pro Ala Pro Gln Cys Ile
            180                 185                 190

<210> SEQ ID NO 2
<211> LENGTH: 192
<212> TYPE: PRT
<213> ORGANISM: Artificial Sequence
<220> FEATURE:
<223> OTHER INFORMATION: Synthetic construct

<400> SEQUENCE: 2

Gln Cys Asn Ala Pro Glu Trp Leu Pro Phe Ala Arg Pro Thr Asn Leu
  1               5                  10                  15

Thr Asp Glu Phe Glu Phe Pro Ile Gly Thr Tyr Leu Lys Tyr Glu Cys
                 20                  25                  30

Arg Pro Gly Tyr Ser Gly Arg Pro Phe Ser Ile Ile Cys Leu Lys Asn
                 35                  40                  45

Ser Val Trp Thr Gly Ala Lys Asp Arg Cys Arg Arg Lys Ser Cys Arg
 50                  55                  60

Asn Pro Pro Asp Pro Val Asn Gly Met Val His Val Ile Lys Gly Ile
 65                  70                  75                  80

Gln Phe Gly Ser Gln Ile Lys Tyr Ser Cys Thr Lys Gly Tyr Arg Leu
                 85                  90                  95

Ile Gly Ser Ser Ser Ala Thr Cys Ile Ile Ser Gly Asn Thr Val Ile
                100                 105                 110

Trp Asp Asn Glu Thr Pro Ile Cys Asp Arg Ile Pro Cys Gly Leu Pro
                115                 120                 125

Pro Thr Ile Thr Asn Gly Asp Phe Ile Ser Thr Asn Arg Glu Asn Phe
            130                 135                 140

His Tyr Gly Ser Val Val Thr Tyr Arg Cys Asn Pro Gly Ser Gly Gly
145                 150                 155                 160

Arg Lys Val Phe Glu Leu Val Gly Glu Pro Ser Ile Tyr Cys Thr Ser
                165                 170                 175

Asn Asp Asp Gln Val Gly Ile Trp Ser Gly Pro Ala Pro Gln Cys Ile
            180                 185                 190

<210> SEQ ID NO 3
<211> LENGTH: 192
<212> TYPE: PRT
<213> ORGANISM: Artificial Sequence
<220> FEATURE:
<223> OTHER INFORMATION: Synthetic construct
```

<400> SEQUENCE: 3

```
Gln Cys Asn Ala Pro Glu Trp Leu Pro Phe Ala Arg Pro Thr Asn Leu
1               5                   10                  15

Thr Asp Glu Phe Glu Phe Pro Ile Gly Thr Tyr Leu Asn Tyr Glu Cys
            20                  25                  30

Arg Pro Gly Tyr Tyr Gly Arg Pro Phe Ser Ile Ile Cys Leu Lys Asn
        35                  40                  45

Ser Val Trp Thr Gly Ala Lys Asp Arg Cys Arg Arg Lys Ser Cys Arg
    50                  55                  60

Asn Pro Pro Asp Pro Val Asn Gly Met Val His Val Ile Lys Asp Ile
65                  70                  75                  80

Gln Phe Gly Ser Gln Ile Lys Tyr Ser Cys Thr Lys Gly Tyr Arg Leu
                85                  90                  95

Ile Gly Ser Ser Ser Ala Thr Cys Ile Ile Ser Gly Asp Thr Val Ile
            100                 105                 110

Trp Asp Asn Glu Thr Pro Ile Cys Asp Arg Ile Pro Cys Gly Leu Pro
        115                 120                 125

Pro Thr Ile Thr Asn Gly Asp Phe Ile Ser Thr Asn Arg Glu Asn Phe
    130                 135                 140

His Tyr Gly Ser Val Val Thr Tyr Arg Cys Asn Pro Gly Ser Gly Gly
145                 150                 155                 160

Arg Lys Val Phe Glu Leu Val Gly Glu Pro Ser Ile Tyr Cys Thr Ser
                165                 170                 175

Asn Asp Asp Gln Val Gly Ile Trp Ser Gly Pro Ala Pro Gln Cys Ile
            180                 185                 190
```

<210> SEQ ID NO 4
<211> LENGTH: 192
<212> TYPE: PRT
<213> ORGANISM: Artificial Sequence
<220> FEATURE:
<223> OTHER INFORMATION: Synthetic construct

<400> SEQUENCE: 4

```
Gln Cys Asn Ala Pro Glu Trp Leu Pro Phe Ala Arg Pro Thr Asn Leu
1               5                   10                  15

Thr Asp Glu Phe Glu Phe Pro Ile Gly Thr Tyr Leu Lys Tyr Glu Cys
            20                  25                  30

Arg Pro Gly Tyr Tyr Gly Arg Pro Phe Ser Ile Ile Cys Leu Lys Asn
        35                  40                  45

Ser Val Trp Thr Gly Ala Lys Asp Arg Cys Arg Arg Lys Ser Cys Arg
    50                  55                  60

Asn Pro Pro Asp Pro Val Asn Gly Met Val His Val Ile Lys Asp Ile
65                  70                  75                  80

Gln Phe Gly Ser Gln Ile Lys Tyr Ser Cys Thr Lys Gly Tyr Arg Leu
                85                  90                  95

Ile Gly Ser Ser Ser Ala Thr Cys Ile Ile Ser Gly Asn Thr Val Ile
            100                 105                 110

Trp Asp Asn Glu Thr Pro Ile Cys Asp Arg Ile Pro Cys Gly Leu Pro
        115                 120                 125

Pro Thr Ile Thr Asn Gly Asp Phe Ile Ser Thr Asn Arg Glu Asn Phe
    130                 135                 140

His Tyr Gly Ser Val Val Thr Tyr Arg Cys Asn Pro Gly Ser Gly Gly
145                 150                 155                 160
```

Arg Lys Val Phe Glu Leu Val Gly Glu Pro Ser Ile Tyr Cys Thr Ser
            165                 170                 175

Asn Asp Asp Gln Val Gly Ile Trp Ser Gly Pro Ala Pro Gln Cys Ile
        180                 185                 190

<210> SEQ ID NO 5
<211> LENGTH: 192
<212> TYPE: PRT
<213> ORGANISM: Homo sapiens

<400> SEQUENCE: 5

His Cys Gln Ala Pro Asp His Phe Leu Phe Ala Lys Leu Lys Thr Gln
1               5                   10                  15

Thr Asn Ala Ser Asp Phe Pro Ile Gly Thr Ser Leu Lys Tyr Glu Cys
            20                  25                  30

Arg Pro Glu Tyr Tyr Gly Arg Pro Phe Ser Ile Thr Cys Leu Asp Asn
        35                  40                  45

Leu Val Trp Ser Ser Pro Lys Asp Val Cys Lys Arg Lys Ser Cys Lys
    50                  55                  60

Thr Pro Pro Asp Pro Val Asn Gly Met Val His Val Ile Thr Asp Ile
65                  70                  75                  80

Gln Val Gly Ser Arg Ile Asn Tyr Ser Cys Thr Thr Gly His Arg Leu
                85                  90                  95

Ile Gly His Ser Ser Ala Glu Cys Ile Leu Ser Gly Asn Ala Ala His
            100                 105                 110

Trp Ser Thr Lys Pro Pro Ile Cys Gln Arg Ile Pro Cys Gly Leu Pro
        115                 120                 125

Pro Thr Ile Ala Asn Gly Asp Phe Ile Ser Thr Asn Arg Glu Asn Phe
    130                 135                 140

His Tyr Gly Ser Val Val Thr Tyr Arg Cys Asn Pro Gly Ser Gly Gly
145                 150                 155                 160

Arg Lys Val Phe Glu Leu Val Gly Glu Pro Ser Ile Tyr Cys Thr Ser
                165                 170                 175

Asn Asp Asp Gln Val Gly Ile Trp Ser Gly Pro Ala Pro Gln Cys Ile
            180                 185                 190

<210> SEQ ID NO 6
<211> LENGTH: 642
<212> TYPE: PRT
<213> ORGANISM: Homo sapiens

<400> SEQUENCE: 6

Gln Cys Asn Ala Pro Glu Trp Leu Pro Phe Ala Arg Pro Thr Asn Leu
1               5                   10                  15

Thr Asp Glu Phe Glu Phe Pro Ile Gly Thr Tyr Leu Asn Tyr Glu Cys
            20                  25                  30

Arg Pro Gly Tyr Ser Gly Arg Pro Phe Ser Ile Ile Cys Leu Lys Asn
        35                  40                  45

Ser Val Trp Thr Gly Ala Lys Asp Arg Cys Arg Arg Lys Ser Cys Arg
    50                  55                  60

Asn Pro Pro Asp Pro Val Asn Gly Met Val His Val Ile Lys Gly Ile
65                  70                  75                  80

Gln Phe Gly Ser Gln Ile Lys Tyr Ser Cys Thr Lys Gly Tyr Arg Leu
                85                  90                  95

Ile Gly Ser Ser Ser Ala Thr Cys Ile Ile Ser Gly Asp Thr Val Ile
            100                 105                 110

-continued

```
Trp Asp Asn Glu Thr Pro Ile Cys Asp Arg Ile Pro Cys Gly Leu Pro
            115                 120                 125
Pro Thr Ile Thr Asn Gly Asp Phe Ile Ser Thr Asn Arg Glu Asn Phe
130                 135                 140
His Tyr Gly Ser Val Val Thr Tyr Arg Cys Asn Pro Gly Ser Gly Gly
145                 150                 155                 160
Arg Lys Val Phe Glu Leu Val Gly Glu Pro Ser Ile Tyr Cys Thr Ser
                165                 170                 175
Asn Asp Asp Gln Val Gly Ile Trp Ser Gly Pro Ala Pro Gln Cys Ile
            180                 185                 190
Ile Pro Asn Lys Cys Thr Pro Pro Asn Val Glu Asn Gly Ile Leu Val
        195                 200                 205
Ser Asp Asn Arg Ser Leu Phe Ser Leu Asn Glu Val Val Glu Phe Arg
210                 215                 220
Cys Gln Pro Gly Phe Val Met Lys Gly Pro Arg Arg Val Lys Cys Gln
225                 230                 235                 240
Ala Leu Asn Lys Trp Glu Pro Glu Leu Pro Ser Cys Ser Arg Val Cys
                245                 250                 255
Gln Pro Pro Pro Asp Val Leu His Ala Glu Arg Thr Gln Arg Asp Lys
            260                 265                 270
Asp Asn Phe Ser Pro Gly Gln Glu Val Phe Tyr Ser Cys Glu Pro Gly
        275                 280                 285
Tyr Asp Leu Arg Gly Ala Ala Ser Met Arg Cys Thr Pro Gln Gly Asp
290                 295                 300
Trp Ser Pro Ala Ala Pro Thr Cys Glu Val Lys Ser Cys Asp Asp Phe
305                 310                 315                 320
Met Gly Gln Leu Leu Asn Gly Arg Val Leu Phe Pro Val Asn Leu Gln
                325                 330                 335
Leu Gly Ala Lys Val Asp Phe Val Cys Asp Glu Gly Phe Gln Leu Lys
            340                 345                 350
Gly Ser Ser Ala Ser Tyr Cys Val Leu Ala Gly Met Glu Ser Leu Trp
        355                 360                 365
Asn Ser Ser Val Pro Val Cys Glu Gln Ile Phe Cys Pro Ser Pro Pro
370                 375                 380
Val Ile Pro Asn Gly Arg His Thr Gly Lys Pro Leu Glu Val Phe Pro
385                 390                 395                 400
Phe Gly Lys Thr Val Asn Tyr Thr Cys Asp Pro His Pro Asp Arg Gly
                405                 410                 415
Thr Ser Phe Asp Leu Ile Gly Glu Ser Thr Ile Arg Cys Thr Ser Asp
            420                 425                 430
Pro Gln Gly Asn Gly Val Trp Ser Ser Pro Ala Pro Arg Cys Gly Ile
        435                 440                 445
Leu Gly His Cys Gln Ala Pro Asp His Phe Leu Phe Ala Lys Leu Lys
450                 455                 460
Thr Gln Thr Asn Ala Ser Asp Phe Pro Ile Gly Thr Ser Leu Lys Tyr
465                 470                 475                 480
Glu Cys Arg Pro Glu Tyr Tyr Gly Arg Pro Phe Ser Ile Thr Cys Leu
                485                 490                 495
Asp Asn Leu Val Trp Ser Ser Pro Lys Asp Val Cys Lys Arg Lys Ser
            500                 505                 510
Cys Lys Thr Pro Pro Asp Pro Val Asn Gly Met Val His Val Ile Thr
        515                 520                 525
Asp Ile Gln Val Gly Ser Arg Ile Asn Tyr Ser Cys Thr Thr Gly His
```

-continued

```
                530             535             540
Arg Leu Ile Gly His Ser Ser Ala Glu Cys Ile Leu Ser Gly Asn Ala
545                 550                 555                 560

Ala His Trp Ser Thr Lys Pro Pro Ile Cys Gln Arg Ile Pro Cys Gly
                565                 570                 575

Leu Pro Pro Thr Ile Ala Asn Gly Asp Phe Ile Ser Thr Asn Arg Glu
                580                 585                 590

Asn Phe His Tyr Gly Ser Val Val Thr Tyr Arg Cys Asn Pro Gly Ser
                595                 600                 605

Gly Gly Arg Lys Val Phe Glu Leu Val Gly Glu Pro Ser Ile Tyr Cys
            610                 615                 620

Thr Ser Asn Asp Asp Gln Val Gly Ile Trp Ser Gly Pro Ala Pro Gln
625                 630                 635                 640

Cys Ile

<210> SEQ ID NO 7
<211> LENGTH: 227
<212> TYPE: PRT
<213> ORGANISM: Homo sapiens

<400> SEQUENCE: 7

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 8
<211> LENGTH: 6
<212> TYPE: PRT
```

-continued

```
<213> ORGANISM: Artificial Sequence
<220> FEATURE:
<223> OTHER INFORMATION: Synthetic construct

<400> SEQUENCE: 8

Gly Gly Gly Gly Gly Gly
  1               5

<210> SEQ ID NO 9
<211> LENGTH: 19
<212> TYPE: PRT
<213> ORGANISM: Artificial Sequence
<220> FEATURE:
<223> OTHER INFORMATION: Synthetic construct

<400> SEQUENCE: 9

Met Ala Trp Met Met Leu Leu Leu Gly Leu Leu Ala Tyr Gly Ser Gly
  1               5                  10                  15

Val Asp Ser

<210> SEQ ID NO 10
<211> LENGTH: 22
<212> TYPE: PRT
<213> ORGANISM: Artificial Sequence
<220> FEATURE:
<223> OTHER INFORMATION: Synthetic construct

<400> SEQUENCE: 10

Met Glu Thr Asp Thr Leu Leu Leu Trp Val Leu Leu Leu Trp Val Pro
  1               5                  10                  15

Gly Ser Thr Gly Asp Thr
            20

<210> SEQ ID NO 11
<211> LENGTH: 202
<212> TYPE: PRT
<213> ORGANISM: Homo sapiens

<400> SEQUENCE: 11

Gly Arg Pro Phe Val Glu Met Tyr Ser Glu Ile Pro Glu Ile Ile His
  1               5                  10                  15

Met Thr Glu Gly Arg Glu Leu Val Ile Pro Cys Arg Val Thr Ser Pro
                20                  25                  30

Asn Ile Thr Val Thr Leu Lys Lys Phe Pro Leu Asp Thr Leu Ile Pro
            35                  40                  45

Asp Gly Lys Arg Ile Ile Trp Asp Ser Arg Lys Gly Phe Ile Ile Ser
        50                  55                  60

Asn Ala Thr Tyr Lys Glu Ile Gly Leu Leu Thr Cys Glu Ala Thr Val
 65                  70                  75                  80

Asn Gly His Leu Tyr Lys Thr Asn Tyr Leu Thr His Arg Gln Thr Asn
                85                  90                  95

Thr Ile Ile Asp Val Val Leu Ser Pro Ser His Gly Ile Glu Leu Ser
                100                 105                 110

Val Gly Glu Lys Leu Val Leu Asn Cys Thr Ala Arg Thr Glu Leu Asn
            115                 120                 125

Val Gly Ile Asp Phe Asn Trp Glu Tyr Pro Ser Ser Lys His Gln His
        130                 135                 140

Lys Lys Leu Val Asn Arg Asp Leu Lys Thr Gln Ser Gly Ser Glu Met
145                 150                 155                 160

Lys Lys Phe Leu Ser Thr Leu Thr Ile Asp Gly Val Thr Arg Ser Asp
```

```
                    165                 170                 175

Gln Gly Leu Tyr Thr Cys Ala Ala Ser Ser Gly Leu Met Thr Lys Lys
            180                 185                 190

Asn Ser Thr Phe Val Arg Val His Glu Lys
        195                 200

<210> SEQ ID NO 12
<211> LENGTH: 627
<212> TYPE: PRT
<213> ORGANISM: Artificial Sequence
<220> FEATURE:
<223> OTHER INFORMATION: Synthetic construct

<400> SEQUENCE: 12

Gly Arg Pro Phe Val Glu Met Tyr Ser Glu Ile Pro Glu Ile Ile His
1               5                   10                  15

Met Thr Glu Gly Arg Glu Leu Val Ile Pro Cys Arg Val Thr Ser Pro
            20                  25                  30

Asn Ile Thr Val Thr Leu Lys Lys Phe Pro Leu Asp Thr Leu Ile Pro
        35                  40                  45

Asp Gly Lys Arg Ile Ile Trp Asp Ser Arg Lys Gly Phe Ile Ile Ser
50                  55                  60

Asn Ala Thr Tyr Lys Glu Ile Gly Leu Leu Thr Cys Glu Ala Thr Val
65                  70                  75                  80

Asn Gly His Leu Tyr Lys Thr Asn Tyr Leu Thr His Arg Gln Thr Asn
                85                  90                  95

Thr Ile Ile Asp Val Val Leu Ser Pro Ser His Gly Ile Glu Leu Ser
            100                 105                 110

Val Gly Glu Lys Leu Val Leu Asn Cys Thr Ala Arg Thr Glu Leu Asn
        115                 120                 125

Val Gly Ile Asp Phe Asn Trp Glu Tyr Pro Ser Ser Lys His Gln His
    130                 135                 140

Lys Lys Leu Val Asn Arg Asp Leu Lys Thr Gln Ser Gly Ser Glu Met
145                 150                 155                 160

Lys Lys Phe Leu Ser Thr Leu Thr Ile Asp Gly Val Thr Arg Ser Asp
                165                 170                 175

Gln Gly Leu Tyr Thr Cys Ala Ala Ser Ser Gly Leu Met Thr Lys Lys
            180                 185                 190

Asn Ser Thr Phe Val Arg Val His Glu Lys Asp Lys Thr His Thr Cys
        195                 200                 205

Pro Pro Cys Pro Ala Pro Glu Leu Leu Gly Gly Pro Ser Val Phe Leu
    210                 215                 220

Phe Pro Pro Lys Pro Lys Asp Thr Leu Met Ile Ser Arg Thr Pro Glu
225                 230                 235                 240

Val Thr Cys Val Val Val Asp Val Ser His Glu Asp Pro Glu Val Lys
                245                 250                 255

Phe Asn Trp Tyr Val Asp Gly Val Glu Val His Asn Ala Lys Thr Lys
            260                 265                 270

Pro Arg Glu Glu Gln Tyr Asn Ser Thr Tyr Arg Val Val Ser Val Leu
        275                 280                 285

Thr Val Leu His Gln Asp Trp Leu Asn Gly Lys Glu Tyr Lys Cys Lys
    290                 295                 300

Val Ser Asn Lys Ala Leu Pro Ala Pro Ile Glu Lys Thr Ile Ser Lys
305                 310                 315                 320

Ala Lys Gly Gln Pro Arg Glu Pro Gln Val Tyr Thr Leu Pro Pro Ser
```

```
                    325                 330                 335
Arg Asp Glu Leu Thr Lys Asn Gln Val Ser Leu Thr Cys Leu Val Lys
            340                 345                 350

Gly Phe Tyr Pro Ser Asp Ile Ala Val Glu Trp Glu Ser Asn Gly Gln
        355                 360                 365

Pro Glu Asn Asn Tyr Lys Thr Thr Pro Val Leu Asp Ser Asp Gly
370                 375                 380

Ser Phe Phe Leu Tyr Ser Lys Leu Thr Val Asp Lys Ser Arg Trp Gln
385                 390                 395                 400

Gln Gly Asn Val Phe Ser Cys Ser Val Met His Glu Ala Leu His Asn
                405                 410                 415

His Tyr Thr Gln Lys Ser Leu Ser Leu Ser Pro Gly Lys Gly Gly Gly
            420                 425                 430

Gly Gly Gly Gln Cys Asn Ala Pro Glu Trp Leu Pro Phe Ala Arg Pro
        435                 440                 445

Thr Asn Leu Thr Asp Glu Phe Glu Phe Pro Ile Gly Thr Tyr Leu Lys
    450                 455                 460

Tyr Glu Cys Arg Pro Gly Tyr Tyr Gly Arg Pro Phe Ser Ile Ile Cys
465                 470                 475                 480

Leu Lys Asn Ser Val Trp Thr Gly Ala Lys Asp Arg Cys Arg Arg Lys
                485                 490                 495

Ser Cys Arg Asn Pro Pro Asp Pro Val Asn Gly Met Val His Val Ile
            500                 505                 510

Lys Asp Ile Gln Phe Gly Ser Gln Ile Lys Tyr Ser Cys Thr Lys Gly
        515                 520                 525

Tyr Arg Leu Ile Gly Ser Ser Ser Ala Thr Cys Ile Ile Ser Gly Asn
530                 535                 540

Thr Val Ile Trp Asp Asn Glu Thr Pro Ile Cys Asp Arg Ile Pro Cys
545                 550                 555                 560

Gly Leu Pro Pro Thr Ile Thr Asn Gly Asp Phe Ile Ser Thr Asn Arg
                565                 570                 575

Glu Asn Phe His Tyr Gly Ser Val Val Thr Tyr Arg Cys Asn Pro Gly
            580                 585                 590

Ser Gly Gly Arg Lys Val Phe Glu Leu Val Gly Glu Pro Ser Ile Tyr
        595                 600                 605

Cys Thr Ser Asn Asp Asp Gln Val Gly Ile Trp Ser Gly Pro Ala Pro
    610                 615                 620

Gln Cys Ile
625

<210> SEQ ID NO 13
<211> LENGTH: 189
<212> TYPE: PRT
<213> ORGANISM: Homo sapiens

<400> SEQUENCE: 13

Arg Ser Cys Glu Val Pro Thr Arg Leu Asn Ser Ala Ser Leu Lys Gln
  1               5                  10                  15

Pro Tyr Ile Thr Gln Asn Tyr Phe Pro Val Gly Thr Val Val Glu Tyr
             20                  25                  30

Glu Cys Arg Pro Gly Tyr Arg Arg Glu Pro Ser Leu Ser Pro Lys Leu
         35                  40                  45

Thr Cys Leu Gln Asn Leu Lys Trp Ser Thr Ala Val Glu Phe Cys Lys
     50                  55                  60
```

```
Lys Lys Ser Cys Pro Asn Pro Gly Glu Ile Arg Asn Gly Gln Ile Asp
 65                  70                  75                  80

Val Pro Gly Gly Ile Leu Phe Gly Ala Thr Ile Ser Phe Ser Cys Asn
                 85                  90                  95

Thr Gly Tyr Lys Leu Phe Gly Ser Thr Ser Ser Phe Cys Leu Ile Ser
            100                 105                 110

Gly Ser Ser Val Gln Trp Ser Asp Pro Leu Pro Glu Cys Arg Glu Ile
        115                 120                 125

Tyr Cys Pro Ala Pro Pro Gln Ile Asp Asn Gly Ile Ile Gln Gly Glu
    130                 135                 140

Arg Asp His Tyr Gly Tyr Arg Gln Ser Val Thr Tyr Ala Cys Asn Lys
145                 150                 155                 160

Gly Phe Thr Met Ile Gly Glu His Ser Ile Tyr Cys Thr Val Asn Asn
                165                 170                 175

Asp Glu Gly Glu Trp Ser Gly Pro Pro Pro Glu Cys Arg
            180                 185

<210> SEQ ID NO 14
<211> LENGTH: 189
<212> TYPE: PRT
<213> ORGANISM: Homo sapiens

<400> SEQUENCE: 14

Arg Glu Thr Cys Pro Tyr Ile Arg Asp Pro Leu Asn Gly Gln Ala Val
  1               5                  10                  15

Pro Ala Asn Gly Thr Tyr Glu Phe Gly Tyr Gln Met His Phe Ile Cys
                 20                  25                  30

Asn Glu Gly Tyr Tyr Leu Ile Gly Glu Glu Ile Leu Tyr Cys Glu Leu
             35                  40                  45

Lys Gly Ser Val Ala Ile Trp Ser Gly Lys Pro Pro Ile Cys Glu Lys
         50                  55                  60

Val Leu Cys Thr Pro Pro Lys Ile Lys Asn Gly Lys His Thr Phe
 65                  70                  75                  80

Ser Glu Val Glu Val Phe Glu Tyr Leu Asp Ala Val Thr Tyr Ser Cys
                 85                  90                  95

Asp Pro Ala Pro Gly Pro Asp Pro Phe Ser Leu Ile Gly Glu Ser Thr
                100                 105                 110

Ile Tyr Cys Gly Asp Asn Ser Val Trp Ser Arg Ala Ala Pro Glu Cys
            115                 120                 125

Lys Val Val Lys Cys Arg Phe Pro Val Val Glu Asn Gly Lys Gln Ile
        130                 135                 140

Ser Gly Phe Gly Lys Lys Phe Tyr Tyr Lys Ala Thr Val Met Phe Glu
145                 150                 155                 160

Cys Asp Lys Gly Phe Tyr Leu Asp Gly Ser Asp Thr Ile Val Cys Asp
                165                 170                 175

Ser Asn Ser Thr Trp Asp Pro Val Pro Lys Cys Leu
            180                 185

<210> SEQ ID NO 15
<211> LENGTH: 245
<212> TYPE: PRT
<213> ORGANISM: Homo sapiens

<400> SEQUENCE: 15

Glu Asp Cys Asn Glu Leu Pro Pro Arg Arg Asn Thr Glu Ile Leu Thr
  1               5                  10                  15
```

Gly Ser Trp Ser Asp Gln Thr Tyr Pro Glu Gly Thr Gln Ala Ile Tyr
            20                  25                  30

Lys Cys Arg Pro Gly Tyr Arg Ser Leu Gly Asn Val Ile Met Val Cys
         35                  40                  45

Arg Lys Gly Glu Trp Val Ala Leu Asn Pro Leu Arg Lys Cys Gln Lys
 50                  55                  60

Arg Pro Cys Gly His Pro Gly Asp Thr Pro Phe Gly Thr Phe Thr Leu
 65                  70                  75                  80

Thr Gly Gly Asn Val Phe Glu Tyr Gly Val Lys Ala Val Tyr Thr Cys
                 85                  90                  95

Asn Glu Gly Tyr Gln Leu Leu Gly Glu Ile Asn Tyr Arg Glu Cys Asp
            100                 105                 110

Thr Asp Gly Trp Thr Asn Asp Ile Pro Ile Cys Glu Val Val Lys Cys
        115                 120                 125

Leu Pro Val Thr Ala Pro Glu Asn Gly Lys Ile Val Ser Ser Ala Met
130                 135                 140

Glu Pro Asp Arg Glu Tyr His Phe Gly Gln Ala Val Arg Phe Val Cys
145                 150                 155                 160

Asn Ser Gly Tyr Lys Ile Glu Gly Asp Glu Glu Met His Cys Ser Asp
                165                 170                 175

Asp Gly Phe Trp Ser Lys Glu Lys Pro Lys Cys Val Glu Ile Ser Cys
            180                 185                 190

Lys Ser Pro Asp Val Ile Asn Gly Ser Pro Ile Ser Gln Lys Ile Ile
        195                 200                 205

Tyr Lys Glu Asn Glu Arg Phe Gln Tyr Lys Cys Asn Met Gly Tyr Glu
210                 215                 220

Tyr Ser Glu Arg Gly Asp Ala Val Cys Thr Glu Ser Gly Trp Arg Pro
225                 230                 235                 240

Leu Pro Ser Cys Glu
                245

<210> SEQ ID NO 16
<211> LENGTH: 187
<212> TYPE: PRT
<213> ORGANISM: Homo sapiens

<400> SEQUENCE: 16

Asn Cys Gly Pro Pro Thr Leu Ser Phe Ala Ala Pro Met Asp Ile
 1               5                  10                  15

Thr Leu Thr Glu Thr Arg Phe Lys Thr Gly Thr Thr Leu Lys Tyr Thr
            20                  25                  30

Cys Leu Pro Gly Tyr Val Arg Ser His Ser Thr Gln Thr Leu Thr Cys
         35                  40                  45

Asn Ser Asp Gly Glu Trp Val Tyr Asn Thr Phe Cys Ile Tyr Lys Arg
 50                  55                  60

Cys Arg His Pro Gly Glu Leu Arg Asn Gly Gln Val Glu Ile Lys Thr
 65                  70                  75                  80

Asp Leu Ser Phe Gly Ser Gln Ile Glu Phe Ser Cys Ser Glu Gly Phe
                 85                  90                  95

Phe Leu Ile Gly Ser Thr Thr Ser Arg Cys Glu Val Gln Asp Arg Gly
            100                 105                 110

Val Gly Trp Ser His Pro Leu Pro Gln Cys Glu Ile Val Lys Cys Lys
        115                 120                 125

Pro Pro Pro Asp Ile Arg Asn Gly Arg His Ser Gly Glu Glu Asn Phe
130                 135                 140

```
Tyr Ala Tyr Gly Phe Ser Val Thr Tyr Ser Cys Asp Pro Arg Phe Ser
145                 150                 155                 160

Leu Leu Gly His Ala Ser Ile Ser Cys Thr Val Glu Asn Glu Thr Ile
            165                 170                 175

Gly Val Trp Arg Pro Ser Pro Pro Thr Cys Glu
            180                 185
```

<210> SEQ ID NO 17
<211> LENGTH: 576
<212> TYPE: DNA
<213> ORGANISM: Homo sapiens

<400> SEQUENCE: 17

```
caatgcaatg ccccagaatg gcttccattt gccaggccta ccaacctaac tgatgaattt      60
gagtttccca ttgggacata tctgaactat gaatgccgcc ctggttattc cggaagaccg     120
ttttctatca tctgcctaaa aaactcagtc tggactggtg ctaaggacag gtgcagacgt     180
aaatcatgtc gtaatcctcc agatcctgtg aatggcatgg tgcatgtgat caaaggcatc     240
cagttcggat cccaaattaa atattcttgt actaaaggat accgactcat tggttcctcg     300
tctgccacat gcatcatctc aggtgatact gtcatttggg ataatgaaac acctatttgt     360
gacagaattc cttgtgggct acccccccacc atcaccaatg agatttcat tagcaccaac     420
agagagaatt ttcactatgg atcagtggtg acctaccgct gcaatcctgg aagcggaggg     480
agaaaggtgt ttgagcttgt gggtgagccc tccatatact gcaccagcaa tgacgatcaa     540
gtgggcatct ggagcggccc cgcccctcag tgcatt                               576
```

<210> SEQ ID NO 18
<211> LENGTH: 576
<212> TYPE: DNA
<213> ORGANISM: Artificial Sequence
<220> FEATURE:
<223> OTHER INFORMATION: Synthetic construct

<400> SEQUENCE: 18

```
caatgcaatg ccccagaatg gcttccattt gccaggccta ccaacctaac tgatgaattt      60
gagtttccca ttgggacata tctgaaatat gaatgccgcc ctggttattc cggaagaccg     120
ttttctatca tctgcctaaa aaactcagtc tggactggtg ctaaggacag gtgcagacgt     180
aaatcatgtc gtaatcctcc agatcctgtg aatggcatgg tgcatgtgat caaaggcatc     240
cagttcggat cccaaattaa atattcttgt actaaaggat accgactcat tggttcctcg     300
tctgccacat gcatcatctc aggtaatact gtcatttggg ataatgaaac acctatttgt     360
gacagaattc cttgtgggct acccccccacc atcaccaatg agatttcat tagcaccaac     420
agagagaatt ttcactatgg atcagtggtg acctaccgct gcaatcctgg aagcggaggg     480
agaaaggtgt ttgagcttgt gggtgagccc tccatatact gcaccagcaa tgacgatcaa     540
gtgggcatct ggagcggccc cgcccctcag tgcatt                               576
```

<210> SEQ ID NO 19
<211> LENGTH: 576
<212> TYPE: DNA
<213> ORGANISM: Artificial Sequence
<220> FEATURE:
<223> OTHER INFORMATION: Synthetic construct

<400> SEQUENCE: 19

```
caatgcaatg ccccagaatg gcttccattt gccaggccta ccaacctaac tgatgaattt      60
```

```
gagtttccca ttgggacata tctgaactat gaatgccgcc ctggttatta cggaagaccg    120
ttttctatca tctgcctaaa aaactcagtc tggactggtg ctaaggacag gtgcagacgt    180
aaatcatgtc gtaatcctcc agatcctgtg aatggcatgg tgcatgtgat caaagacatc    240
cagttcggat cccaaattaa atattcttgt actaaaggat accgactcat tggttcctcg    300
tctgccacat gcatcatctc aggtgatact gtcatttggg ataatgaaac acctatttgt    360
gacagaattc cttgtgggct acccccccacc atcaccaatg gagatttcat tagcaccaac    420
agagagaatt ttcactatgg atcagtggtg acctaccgct gcaatcctgg aagcggaggg    480
agaaaggtgt ttgagcttgt gggtgagccc tccatatact gcaccagcaa tgacgatcaa    540
gtgggcatct ggagcggccc cgcccctcag tgcatt                              576

<210> SEQ ID NO 20
<211> LENGTH: 576
<212> TYPE: DNA
<213> ORGANISM: Artificial Sequence
<220> FEATURE:
<223> OTHER INFORMATION: Synthetic construct

<400> SEQUENCE: 20
caatgcaatg ccccagaatg gcttccattt gccaggccta ccaacctaac tgatgaattt     60
gagtttccca ttgggacata tctgaaatat gaatgccgcc ctggttatta cggaagaccg    120
ttttctatca tctgcctaaa aaactcagtc tggactggtg ctaaggacag gtgcagacgt    180
aaatcatgtc gtaatcctcc agatcctgtg aatggcatgg tgcatgtgat caaagacatc    240
cagttcggat cccaaattaa atattcttgt actaaaggat accgactcat tggttcctcg    300
tctgccacat gcatcatctc aggtaatact gtcatttggg ataatgaaac acctatttgt    360
gacagaattc cttgtgggct acccccccacc atcaccaatg gagatttcat tagcaccaac    420
agagagaatt ttcactatgg atcagtggtg acctaccgct gcaatcctgg aagcggaggg    480
agaaaggtgt ttgagcttgt gggtgagccc tccatatact gcaccagcaa tgacgatcaa    540
gtgggcatct ggagcggccc cgcccctcag tgcatt                              576

<210> SEQ ID NO 21
<211> LENGTH: 576
<212> TYPE: DNA
<213> ORGANISM: Homo sapiens

<400> SEQUENCE: 21
cactgtcaag ccccagatca ttttctgttt gccaagttga aaacccaaac caatgcatct     60
gactttccca ttgggacatc tttaaagtac gaatgccgtc ctgagtacta cgggaggcca    120
ttctctatca catgtctaga taacctggtc tggtcaagtc ccaaagatgt ctgtaaacgt    180
aaatcatgta aaactcctcc agatccagtg aatggcatgg tgcatgtgat cacagacatc    240
caggttggat ccagaatcaa ctattcttgt actacagggc accgactcat tggtcactca    300
tctgctgaat gtatcctctc gggcaatgct gcccattgga gcacgaagcc gccaatttgt    360
caacgaattc cttgtgggct acccccccacc atcgccaatg gagatttcat tagcaccaac    420
agagagaatt ttcactatgg atcagtggtg acctaccgct gcaatcctgg aagcggaggg    480
agaaaggtgt ttgagcttgt gggtgagccc tccatatact gcaccagcaa tgacgatcaa    540
gtgggcatct ggagcggccc ggcccctcag tgcatt                              576

<210> SEQ ID NO 22
```

<211> LENGTH: 1926
<212> TYPE: DNA
<213> ORGANISM: Homo sapiens

<400> SEQUENCE: 22

| | | | | | |
|---|---|---|---|---|---|
| caatgcaatg | ccccagaatg | gcttccattt | gccaggccta | ccaacctaac | tgatgaattt | 60 |
| gagtttccca | ttgggacata | tctgaactat | gaatgccgcc | ctggttattc | cggaagaccg | 120 |
| ttttctatca | tctgcctaaa | aaactcagtc | tggactggtg | ctaaggacag | gtgcagacgt | 180 |
| aaatcatgtc | gtaatcctcc | agatcctgtg | aatggcatgg | tgcatgtgat | caaaggcatc | 240 |
| cagttcggat | cccaaattaa | atattcttgt | actaaaggat | accgactcat | tggttcctcg | 300 |
| tctgccacat | gcatcatctc | aggtgatact | gtcatttggg | ataatgaaac | acctatttgt | 360 |
| gacagaattc | cttgtgggct | accccccacc | atcaccaatg | gagatttcat | tagcaccaac | 420 |
| agagagaatt | ttcactatgg | atcagtggtg | acctaccgct | gcaatcctgg | aagcggaggg | 480 |
| agaaaggtgt | ttgagcttgt | gggtgagccc | tccatatact | gcaccagcaa | tgacgatcaa | 540 |
| gtgggcatct | ggagcggccc | cgcccctcag | tgcattatac | ctaacaaatg | cacgcctcca | 600 |
| aatgtggaaa | atggaatatt | ggtatctgac | aacagaagct | tattttcctt | aaatgaagtt | 660 |
| gtggagttta | ggtgtcagcc | tggctttgtc | atgaaaggac | cccgccgtgt | gaagtgccag | 720 |
| gccctgaaca | atgggagcc | ggagctacca | agctgctcca | gggtatgtca | gccacctcca | 780 |
| gatgtcctgc | atgctgagcg | tacccaaagg | gacaaggaca | acttttcacc | tgggcaggaa | 840 |
| gtgttctaca | gctgtgagcc | cggctacgac | ctcagagggg | ctgcgtctat | gcgctgcaca | 900 |
| ccccagggag | actggagccc | tgcagccccc | acatgtgaag | tgaaatcctg | tgatgacttc | 960 |
| atgggccaac | ttcttaatgg | ccgtgtgcta | tttccagtaa | atctccagct | tggagcaaaa | 1020 |
| gtggattttg | tttgtgatga | aggatttcaa | ttaaaaggca | gctctgctag | ttactgtgtc | 1080 |
| ttggctggaa | tggaaagcct | ttggaatagc | agtgttccag | tgtgtgaaca | aatcttttgt | 1140 |
| ccaagtcctc | cagttattcc | taatgggaga | cacacaggaa | aacctctgga | agtctttccc | 1200 |
| tttgggaaaa | cagtaaatta | cacatgcgac | ccccacccag | acagagggac | gagcttcgac | 1260 |
| ctcattggag | agagcaccat | ccgctgcaca | agtgaccctc | aagggaatgg | ggtttggagc | 1320 |
| agccctgccc | ctcgctgtgg | aattctgggt | cactgtcaag | ccccagatca | ttttctgttt | 1380 |
| gccaagttga | aaacccaaac | caatgcatct | gactttccca | ttgggacatc | tttaaagtac | 1440 |
| gaatgccgtc | ctgagtacta | cgggaggcca | ttctctatca | catgtctaga | taacctggtc | 1500 |
| tggtcaagtc | ccaaagatgt | ctgtaaacgt | aaatcatgta | aaactcctcc | agatccagtg | 1560 |
| aatggcatgg | tgcatgtgat | cacagacatc | caggttggat | ccagaatcaa | ctattcttgt | 1620 |
| actacagggc | accgactcat | tggtcactca | tctgctgaat | gtatcctctc | gggcaatgct | 1680 |
| gcccattgga | gcacgaagcc | gccaatttgt | caacgaattc | cttgtgggct | accccccacc | 1740 |
| atcgccaatg | gagatttcat | tagcaccaac | agagagaatt | ttcactatgg | atcagtggtg | 1800 |
| acctaccgct | gcaatcctgg | aagcggaggg | agaaaggtgt | ttgagcttgt | gggtgagccc | 1860 |
| tccatatact | gcaccagcaa | tgacgatcaa | gtgggcatct | ggagcggccc | ggcccctcag | 1920 |
| tgcatt | | | | | | 1926 |

<210> SEQ ID NO 23
<211> LENGTH: 681
<212> TYPE: DNA
<213> ORGANISM: Homo sapiens

<400> SEQUENCE: 23

```
gacaaaactc acacatgccc accgtgccca gcacctgaac tcctgggggg accgtcagtc    60
ttcctcttcc cccaaaacc caaggacacc ctcatgatct cccggacccc tgaggtcaca    120
tgcgtggtgg tggacgtgag ccacgaagac cctgaggtca agttcaactg gtacgtggac    180
ggcgtggagg tgcataatgc caagacaaag ccgcggagg agcagtacaa cagcacgtac    240
cgtgtggtca gcgtcctcac cgtcctgcac caggactggc tgaatggcaa ggagtacaag    300
tgcaaggtct ccaacaaagc cctcccagcc cccatcgaga aaaccatctc caaagccaaa    360
gggcagcccc gagaaccaca ggtgtacacc ctgcccccat cccgggagga tgaccaag    420 aaccaggtca gcctgacctg cctggtcaaa ggcttctatc ccagcgacat cgccgtggag    480
tgggagagca atgggcagcc ggagaacaac tacaagacca cgcctcccgt gctggactcc    540
gacggctcct tcttcctcta tagcaagctc accgtggaca agagcaggtg gcagcagggg    600
aacgtcttct catgctccgt gatgcatgag gctctgcaca accactatac gcagaagagc    660 ctctcccctgt ctccgggtaa a                                              681
```

```
<210> SEQ ID NO 24
<211> LENGTH: 18
<212> TYPE: DNA
<213> ORGANISM: Artificial Sequence
<220> FEATURE:
<223> OTHER INFORMATION: Synthetic construct

<400> SEQUENCE: 24
ggaggtggag gcggtggt                                                   18

<210> SEQ ID NO 25
<211> LENGTH: 57
<212> TYPE: DNA
<213> ORGANISM: Artificial Sequence
<220> FEATURE:
<223> OTHER INFORMATION: Synthetic construct

<400> SEQUENCE: 25
atggcctgga tgatgcttct cctcggactc cttgcttatg gatcaggagt cgactct       57

<210> SEQ ID NO 26
<211> LENGTH: 66
<212> TYPE: DNA
<213> ORGANISM: Artificial Sequence
<220> FEATURE:
<223> OTHER INFORMATION: Synthetic construct

<400> SEQUENCE: 26
atggagacag acacactcct gctatgggta ctgctgctct gggttccagg gtcgactggc    60
gacact                                                                66

<210> SEQ ID NO 27
<211> LENGTH: 606
<212> TYPE: DNA
<213> ORGANISM: Homo sapiens

<400> SEQUENCE: 27
ggtagacctt tcgtagagat gtacagtgaa atccccgaaa ttatacacat gactgaagga    60
agggagctcg tcattccctg ccgggttacg tcacctaaca tcactgttac tttaaaaaag    120
tttccacttg acactttgat ccctgatgga aaacgcataa tctgggacag tagaaagggc    180
ttcatcatat caaatgcaac gtacaaagaa atagggcttc tgacctgtga agcaacagtc    240
```

| | |
|---|---|
| aatgggcatt tgtataagac aaactatctc acacatcgac aaaccaatac aatcatagat | 300 |
| gtggttctga gtccgtctca tggaattgaa ctatctgttg agaaaagct tgtcttaaat | 360 |
| tgtacagcaa gaactgaact aaatgtgggg attgacttca actgggaata cccttcttcg | 420 |
| aagcatcagc ataagaaact tgtaaaccga gacctaaaaa cccagtctgg gagtgagatg | 480 |
| aagaaatttt tgagcacctt aactatagat ggtgtaaccc ggagtgacca aggattgtac | 540 |
| acctgtgcag catccagtgg gctgatgacc aagaagaaca gcacatttgt cagggtccat | 600 |
| gaaaag | 606 |

<210> SEQ ID NO 28
<211> LENGTH: 1881
<212> TYPE: DNA
<213> ORGANISM: Artificial Sequence
<220> FEATURE:
<223> OTHER INFORMATION: Synthetic construct

<400> SEQUENCE: 28

| | |
|---|---|
| ggaagacctt ttgttgaaat gtattctgaa attcctgaaa ttattcatat gactgaagga | 60 |
| agagaacttg ttattccttg tagagttact tctcctaata ttactgttac tcttaagaag | 120 |
| tttcctcttg atactcttat tcctgatgga aagagaatta tttgggattc tagaaaggga | 180 |
| tttattattt ctaatgctac ttataaggaa attggacttc ttacttgtga agctactgtt | 240 |
| aatggacatc tttataagac taattatctt actcatagac aaactaatac catcatcgac | 300 |
| gtggttctga gtccgtctca tggaattgaa ctatctgttg agaaaagct tgtcttaaat | 360 |
| tgtacagcaa gaactgaact aaatgtgggg attgacttca actgggaata cccttcttcg | 420 |
| aagcatcagc ataagaaact tgtaaaccga gacctaaaaa cccagtctgg gagtgagatg | 480 |
| aagaaattct tgagcaccct gactatagat ggtgtaaccc ggagtgacca aggattgtac | 540 |
| acctgtgcag catccagtgg gctgatgacc aagaagaaca gcacatttgt cagggtccat | 600 |
| gaaaaagaca aaactcacac atgtccaccg tgtccagcac ctgaactcct gggtggaccg | 660 |
| tcagtcttcc tcttcccccc aaaacccaag gacaccctca tgatctcccg gacccctgag | 720 |
| gtcacatgcg tggtggtgga cgtgagccac gaagaccctg aggtcaagtt caactggtac | 780 |
| gtggacggcg tggaggtgca taatgccaag acaaagccgc gggaggagca gtacaacagc | 840 |
| acgtaccgtg tggtcagcgt cctcaccgtc ctgcaccagg actggctgaa tggcaaggag | 900 |
| tacaagtgca aggtctccaa caaagccctc ccagccccca tcgagaaaac catctccaaa | 960 |
| gccaaagggc agccccgaga accacaggtg tacaccctgc ccccatcccg ggatgagctg | 1020 |
| accaagaacc aggtcagcct gacctgcctg gtcaaaggct tctatcccag cgacatcgcc | 1080 |
| gtggagtggg agagcaatgg gcagccggag aacaactaca agaccacgcc tcccgtgctg | 1140 |
| gactccgacg gctccttctt cctctacagc aagctcaccg tggacaagag caggtggcag | 1200 |
| caggggaacg tcttctcatg ctccgtgatg catgaggctc tgcacaacca ctacacgcag | 1260 |
| aagagcctct ccctgtctcc gggtaaaggt ggaggaggcg tggtcaatg caatgcccca | 1320 |
| gaatggcttc catttgccag gcctaccaac ctaactgatg aatttgagtt tcccattggg | 1380 |
| acatatctga aatatgaatg ccgccctggt tattacggaa gaccgttttc tatcatctgc | 1440 |
| ctaaaaaact cagtctggac tggtgctaag gacaggtgca gacgtaaatc atgtcgtaat | 1500 |
| cctccagatc ctgtgaatgg catggtgcat gtgatcaaag acatccagtt cggatcccaa | 1560 |
| attaaatatt cttgtactaa aggataccga ctcattggtt cctcgtctgc cacatgcatc | 1620 |
| atctcaggta atactgtcat ttgggataat gaaacaccta tttgtgacag aattcctgt | 1680 |

| | |
|---|---|
| gggctacccc ccaccatcac caatggagat ttcattagca ccaacagaga gaattttcac | 1740 |
| tatggatcag tggtgaccta ccgctgcaat cctggaagcg gagggagaaa ggtgtttgag | 1800 |
| cttgtgggtg agccctccat atactgcacc agcaatgacg atcaagtggg catctggagc | 1860 |
| ggccccgcac ctcagtgcat t | 1881 |

<210> SEQ ID NO 29
<211> LENGTH: 567
<212> TYPE: DNA
<213> ORGANISM: Homo sapiens

<400> SEQUENCE: 29

| | |
|---|---|
| cgtagctgcg aggtgccaac aaggctaaat tctgcatccc tcaaacagcc ttatatcact | 60 |
| cagaattatt ttccagtcgg tactgttgtg aaatatgagt gccgtccagg ttacagaaga | 120 |
| gaaccttctc tatcaccaaa actaacttgc cttcagaatt taaaatggtc cacagcagtc | 180 |
| gaattttgta aaagaaatc atgccctaat ccgggagaaa tacgaaatgg tcagattgat | 240 |
| gtaccaggtg gcatattatt tggtgcaacc atctccttct catgtaacac agggtacaaa | 300 |
| ttatttggct cgacttctag ttttttgtctt atttcaggca gctctgtcca gtggagtgac | 360 |
| ccgttgccag agtgcagaga aatttattgt ccagcaccac cacaaattga caatggaata | 420 |
| attcaagggg aacgtgacca ttatggatat agacagtctg taacgtatgc atgtaataaa | 480 |
| ggattcacca tgattggaga gcactctatt tattgtactg tgaataatga tgaaggagag | 540 |
| tggagtggcc caccacctga atgcaga | 567 |

<210> SEQ ID NO 30
<211> LENGTH: 567
<212> TYPE: DNA
<213> ORGANISM: Homo sapiens

<400> SEQUENCE: 30

| | |
|---|---|
| agagaaacat gtccatatat acgggatcct ttaaatggcc aagcagtccc tgcaaatggg | 60 |
| acttacgagt ttggttatca gatgcacttt atttgtaatg agggttatta cttaattggt | 120 |
| gaagaaattc tatattgtga acttaaagga tcagtagcaa tttggagcgg taagccccca | 180 |
| atatgtgaaa aggttttgtg tacaccacct ccaaaaataa aaaatggaaa acacaccttt | 240 |
| agtgaagtag aagtatttga gtatcttgat gcagtaactt atagttgtga tcctgcacct | 300 |
| ggaccagatc cattttcact tattggagag agcacgattt attgtggtga caattcagtg | 360 |
| tggagtcgtg ctgctccaga gtgtaaagtg gtcaaatgtc gatttccagt agtcgaaaat | 420 |
| ggaaaacaga tatcaggatt tggaaaaaaa ttttactaca agcaacagt tatgtttgaa | 480 |
| tgcgataagg gttttacct cgatggcagc gacacaattg tctgtgacag taacagtact | 540 |
| tgggatcccc cagttccaaa gtgtctt | 567 |

<210> SEQ ID NO 31
<211> LENGTH: 735
<212> TYPE: DNA
<213> ORGANISM: Homo sapiens

<400> SEQUENCE: 31

| | |
|---|---|
| gaagattgca atgaacttcc tccaagaaga aatacagaaa ttctgacagg ttcctggtct | 60 |
| gaccaaacat atccagaagg cacccaggct atctataaat gccgccctgg atatagatct | 120 |
| cttggaaatg taataatggt atgcaggaag ggagaatggg ttgctcttaa tccattaagg | 180 |

```
aaatgtcaga aaaggccctg tggacatcct ggagatactc cttttggtac ttttacccct    240
acaggaggaa atgtgtttga atatggtgta aaagctgtgt atacatgtaa tgagggtat     300 caattgctag gtgagattaa ttaccgtgaa tgtgacacag atggatggac caatgatatt    360
cctatatgtg aagttgtgaa gtgtttacca gtgacagcac cagagaatgg aaaaattgtc    420
agtagtgcaa tggaaccaga tcgggaatac cattttggac aagcagtacg gtttgtatgt    480
aactcaggct acaagattga aggagatgaa gaaatgcatt gttcagacga tggttttttgg   540 agtaaagaga accaaagtg tgtggaaatt tcatgcaaat ccccagatgt tataaatgga     600
tctcctatat ctcagaagat tatttataag gagaatgaac gatttcaata taaatgtaac    660
atgggttatg aatacagtga agaggagat gctgtatgca ctgaatctgg atggcgtccg     720
ttgccttcat gtgaa                                                    735

<210> SEQ ID NO 32
<211> LENGTH: 561
<212> TYPE: DNA
<213> ORGANISM: Homo sapiens

<400> SEQUENCE: 32
aattgtggtc ctccacccac tttatcattt gctgccccga tggatattac gttgactgag     60
acacgcttca aaactggaac tactctgaaa tacacctgcc tccctggcta cgtcagatcc    120
cattcaactc agacgcttac ctgtaattct gatggcgaat gggtgtataa caccttctgt    180
atctacaaac gatgcagaca cccaggagag ttacgtaatg ggcaagtaga gattaagaca    240
gatttatctt ttggatcaca aatagaattc agctgttcag aaggattttt cttaattggc    300
tcaaccacta gtcgttgtga agtccaagat agaggagttg gctggagtca tcctctccca    360
caatgtgaaa ttgtcaagtg taagcctcct ccagacatca ggaatggaag gcacagcggt    420
gaagaaaatt tctacgcata cggcttttct gtcacctaca gctgtgaccc ccgcttctca    480
ctcttgggcc atgcctccat tcttgcact gtggagaatg aaacaatagg tgtttggaga     540
ccaagccctc ctacctgtga a                                              561

<210> SEQ ID NO 33
<211> LENGTH: 633
<212> TYPE: PRT
<213> ORGANISM: Artificial Sequence
<220> FEATURE:
<223> OTHER INFORMATION: Synthetic construct

<400> SEQUENCE: 33

Gln Cys Asn Ala Pro Glu Trp Leu Pro Phe Ala Arg Pro Thr Asn Leu
  1               5                  10                  15

Thr Asp Glu Phe Glu Phe Pro Ile Gly Thr Tyr Leu Tyr Glu Cys
                 20                  25                  30

Arg Pro Gly Tyr Tyr Gly Arg Pro Phe Ser Ile Ile Cys Leu Lys Asn
             35                  40                  45

Ser Val Trp Thr Gly Ala Lys Asp Arg Cys Arg Arg Lys Ser Cys Arg
     50                  55                  60

Asn Pro Pro Asp Pro Val Asn Gly Met Val His Val Ile Lys Asp Ile
 65                  70                  75                  80

Gln Phe Gly Ser Gln Ile Lys Tyr Ser Cys Thr Lys Gly Tyr Arg Leu
                 85                  90                  95

Ile Gly Ser Ser Ser Ala Thr Cys Ile Ile Ser Gly Asn Thr Val Ile
            100                 105                 110
```

-continued

```
Trp Asp Asn Glu Thr Pro Ile Cys Asp Arg Ile Pro Cys Gly Leu Pro
            115                 120                 125

Pro Thr Ile Thr Asn Gly Asp Phe Ile Ser Thr Asn Arg Glu Asn Phe
        130                 135                 140

His Tyr Gly Ser Val Val Thr Tyr Arg Cys Asn Pro Gly Ser Gly Gly
145                 150                 155                 160

Arg Lys Val Phe Glu Leu Val Gly Glu Pro Ser Ile Tyr Cys Thr Ser
                165                 170                 175

Asn Asp Asp Gln Val Gly Ile Trp Ser Gly Pro Ala Pro Gln Cys Ile
            180                 185                 190

Gly Gly Gly Gly Gly Asp Lys Thr His Thr Cys Pro Pro Cys Pro
        195                 200                 205

Ala Pro Glu Leu Leu Gly Gly Pro Ser Val Phe Leu Phe Pro Pro Lys
210                 215                 220

Pro Lys Asp Thr Leu Met Ile Ser Arg Thr Pro Glu Val Thr Cys Val
225                 230                 235                 240

Val Val Asp Val Ser His Glu Asp Pro Glu Val Lys Phe Asn Trp Tyr
                245                 250                 255

Val Asp Gly Val Glu Val His Asn Ala Lys Thr Lys Pro Arg Glu Glu
        260                 265                 270

Gln Tyr Asn Ser Thr Tyr Arg Val Val Ser Val Leu Thr Val Leu His
                275                 280                 285

Gln Asp Trp Leu Asn Gly Lys Glu Tyr Lys Cys Lys Val Ser Asn Lys
        290                 295                 300

Ala Leu Pro Ala Pro Ile Glu Lys Thr Ile Ser Lys Ala Lys Gly Gln
305                 310                 315                 320

Pro Arg Glu Pro Gln Val Tyr Thr Leu Pro Pro Ser Arg Glu Glu Met
                325                 330                 335

Thr Lys Asn Gln Val Ser Leu Thr Cys Leu Val Lys Gly Phe Tyr Pro
            340                 345                 350

Ser Asp Ile Ala Val Glu Trp Glu Ser Asn Gly Gln Pro Glu Asn Asn
        355                 360                 365

Tyr Lys Thr Thr Pro Pro Val Leu Asp Ser Asp Gly Ser Phe Phe Leu
    370                 375                 380

Tyr Ser Lys Leu Thr Val Asp Lys Ser Arg Trp Gln Gln Gly Asn Val
385                 390                 395                 400

Phe Ser Cys Ser Val Met His Glu Ala Leu His Asn His Tyr Thr Gln
                405                 410                 415

Lys Ser Leu Ser Leu Ser Pro Gly Lys Gly Gly Gly Gly Gly Gly
            420                 425                 430

Arg Pro Phe Val Glu Met Tyr Ser Glu Ile Pro Glu Ile Ile His Met
        435                 440                 445

Thr Glu Gly Arg Glu Leu Val Ile Pro Cys Arg Val Thr Ser Pro Asn
450                 455                 460

Ile Thr Val Thr Leu Lys Lys Phe Pro Leu Asp Thr Leu Ile Pro Asp
465                 470                 475                 480

Gly Lys Arg Ile Ile Trp Asp Ser Arg Lys Gly Phe Ile Ile Ser Asn
                485                 490                 495

Ala Thr Tyr Lys Glu Ile Gly Leu Leu Thr Cys Glu Ala Thr Val Asn
            500                 505                 510

Gly His Leu Tyr Lys Thr Asn Tyr Leu Thr His Arg Gln Thr Asn Thr
        515                 520                 525

Ile Ile Asp Val Val Leu Ser Pro Ser His Gly Ile Glu Leu Ser Val
```

```
                530            535            540
Gly Glu Lys Leu Val Leu Asn Cys Thr Ala Arg Thr Glu Leu Asn Val
545                 550                 555                 560

Gly Ile Asp Phe Asn Trp Glu Tyr Pro Ser Ser Lys His Gln His Lys
                565                 570                 575

Lys Leu Val Asn Arg Asp Leu Lys Thr Gln Ser Gly Ser Glu Met Lys
            580                 585                 590

Lys Phe Leu Ser Thr Leu Thr Ile Asp Gly Val Thr Arg Ser Asp Gln
        595                 600                 605

Gly Leu Tyr Thr Cys Ala Ala Ser Ser Gly Leu Met Thr Lys Lys Asn
    610                 615                 620

Ser Thr Phe Val Arg Val His Glu Lys
625                 630

<210> SEQ ID NO 34
<211> LENGTH: 627
<212> TYPE: PRT
<213> ORGANISM: Artificial Sequence
<220> FEATURE:
<223> OTHER INFORMATION: Synthetic construct

<400> SEQUENCE: 34

Gln Cys Asn Ala Pro Glu Trp Leu Pro Phe Ala Arg Pro Thr Asn Leu
1               5                   10                  15

Thr Asp Glu Phe Glu Phe Pro Ile Gly Thr Tyr Leu Lys Tyr Glu Cys
                20                  25                  30

Arg Pro Gly Tyr Tyr Gly Arg Pro Phe Ser Ile Ile Cys Leu Lys Asn
            35                  40                  45

Ser Val Trp Thr Gly Ala Lys Asp Arg Cys Arg Arg Lys Ser Cys Arg
    50                  55                  60

Asn Pro Pro Asp Pro Val Asn Gly Met Val His Val Ile Lys Asp Ile
65                  70                  75                  80

Gln Phe Gly Ser Gln Ile Lys Tyr Ser Cys Thr Lys Gly Tyr Arg Leu
                85                  90                  95

Ile Gly Ser Ser Ser Ala Thr Cys Ile Ile Ser Gly Asn Thr Val Ile
            100                 105                 110

Trp Asp Asn Glu Thr Pro Ile Cys Asp Arg Ile Pro Cys Gly Leu Pro
        115                 120                 125

Pro Thr Ile Thr Asn Gly Asp Phe Ile Ser Thr Asn Arg Glu Asn Phe
    130                 135                 140

His Tyr Gly Ser Val Val Thr Tyr Arg Cys Asn Pro Gly Ser Gly Gly
145                 150                 155                 160

Arg Lys Val Phe Glu Leu Val Gly Glu Pro Ser Ile Tyr Cys Thr Ser
                165                 170                 175

Asn Asp Asp Gln Val Gly Ile Trp Ser Gly Pro Ala Pro Gln Cys Ile
            180                 185                 190

Gly Gly Gly Gly Gly Gly Arg Pro Phe Val Glu Met Tyr Ser Glu
        195                 200                 205

Ile Pro Glu Ile Ile His Met Thr Glu Gly Arg Glu Leu Val Ile Pro
    210                 215                 220

Cys Arg Val Thr Ser Pro Asn Ile Thr Val Thr Leu Lys Lys Phe Pro
225                 230                 235                 240

Leu Asp Thr Leu Ile Pro Asp Gly Lys Arg Ile Ile Trp Asp Ser Arg
                245                 250                 255

Lys Gly Phe Ile Ile Ser Asn Ala Thr Tyr Lys Glu Ile Gly Leu Leu
```

```
            260                 265                 270
Thr Cys Glu Ala Thr Val Asn Gly His Leu Tyr Lys Thr Asn Tyr Leu
        275                 280                 285
Thr His Arg Gln Thr Asn Thr Ile Ile Asp Val Val Leu Ser Pro Ser
    290                 295                 300
His Gly Ile Glu Leu Ser Val Gly Glu Lys Leu Val Leu Asn Cys Thr
305                 310                 315                 320
Ala Arg Thr Glu Leu Asn Val Gly Ile Asp Phe Asn Trp Glu Tyr Pro
                325                 330                 335
Ser Ser Lys His Gln His Lys Lys Leu Val Asn Arg Asp Leu Lys Thr
            340                 345                 350
Gln Ser Gly Ser Glu Met Lys Lys Phe Leu Ser Thr Leu Thr Ile Asp
        355                 360                 365
Gly Val Thr Arg Ser Asp Gln Gly Leu Tyr Thr Cys Ala Ala Ser Ser
    370                 375                 380
Gly Leu Met Thr Lys Lys Asn Ser Thr Phe Val Arg Val His Glu Lys
385                 390                 395                 400
Asp Lys Thr His Thr Cys Pro Pro Cys Pro Ala Pro Glu Leu Leu Gly
                405                 410                 415
Gly Pro Ser Val Phe Leu Phe Pro Pro Lys Pro Lys Asp Thr Leu Met
            420                 425                 430
Ile Ser Arg Thr Pro Glu Val Thr Cys Val Val Asp Val Ser His
        435                 440                 445
Glu Asp Pro Glu Val Lys Phe Asn Trp Tyr Val Asp Gly Val Glu Val
    450                 455                 460
His Asn Ala Lys Thr Lys Pro Arg Glu Glu Gln Tyr Asn Ser Thr Tyr
465                 470                 475                 480
Arg Val Val Ser Val Leu Thr Val Leu His Gln Asp Trp Leu Asn Gly
                485                 490                 495
Lys Glu Tyr Lys Cys Lys Val Ser Asn Lys Ala Leu Pro Ala Pro Ile
            500                 505                 510
Glu Lys Thr Ile Ser Lys Ala Lys Gly Gln Pro Arg Glu Pro Gln Val
        515                 520                 525
Tyr Thr Leu Pro Pro Ser Arg Glu Glu Met Thr Lys Asn Gln Val Ser
    530                 535                 540
Leu Thr Cys Leu Val Lys Gly Phe Tyr Pro Ser Asp Ile Ala Val Glu
545                 550                 555                 560
Trp Glu Ser Asn Gly Gln Pro Glu Asn Asn Tyr Lys Thr Thr Pro Pro
                565                 570                 575
Val Leu Asp Ser Asp Gly Ser Phe Phe Leu Tyr Ser Lys Leu Thr Val
            580                 585                 590
Asp Lys Ser Arg Trp Gln Gln Gly Asn Val Phe Ser Cys Ser Val Met
        595                 600                 605
His Glu Ala Leu His Asn His Tyr Thr Gln Lys Ser Leu Ser Leu Ser
    610                 615                 620
Pro Gly Lys
625

<210> SEQ ID NO 35
<211> LENGTH: 632
<212> TYPE: PRT
<213> ORGANISM: Artificial Sequence
<220> FEATURE:
<223> OTHER INFORMATION: Synthetic construct
```

<400> SEQUENCE: 35

```
Gly Arg Pro Phe Val Glu Met Tyr Ser Glu Ile Pro Glu Ile Ile His
 1               5                  10                  15
Met Thr Glu Gly Arg Glu Leu Val Ile Pro Cys Arg Val Thr Ser Pro
             20                  25                  30
Asn Ile Thr Val Thr Leu Lys Lys Phe Pro Leu Asp Thr Leu Ile Pro
         35                  40                  45
Asp Gly Lys Arg Ile Ile Trp Asp Ser Arg Lys Gly Phe Ile Ile Ser
     50                  55                  60
Asn Ala Thr Tyr Lys Glu Ile Gly Leu Leu Thr Cys Glu Ala Thr Val
 65                  70                  75                  80
Asn Gly His Leu Tyr Lys Thr Asn Tyr Leu Thr His Arg Gln Thr Asn
                 85                  90                  95
Thr Ile Ile Asp Val Val Leu Ser Pro Ser His Gly Ile Glu Leu Ser
            100                 105                 110
Val Gly Glu Lys Leu Val Leu Asn Cys Thr Ala Arg Thr Glu Leu Asn
        115                 120                 125
Val Gly Ile Asp Phe Asn Trp Glu Tyr Pro Ser Ser Lys His Gln His
    130                 135                 140
Lys Lys Leu Val Asn Arg Asp Leu Lys Thr Gln Ser Gly Ser Glu Met
145                 150                 155                 160
Lys Lys Phe Leu Ser Thr Leu Thr Ile Asp Gly Val Thr Arg Ser Asp
                165                 170                 175
Gln Gly Leu Tyr Thr Cys Ala Ala Ser Ser Gly Leu Met Thr Lys Lys
            180                 185                 190
Asn Ser Thr Phe Val Arg Val His Glu Lys Gly Gly Gly Gly Gly Gly
        195                 200                 205
Gln Cys Asn Ala Pro Glu Trp Leu Pro Phe Ala Arg Pro Thr Asn Leu
    210                 215                 220
Thr Asp Glu Phe Glu Phe Pro Ile Gly Thr Tyr Leu Lys Tyr Glu Cys
225                 230                 235                 240
Arg Pro Gly Tyr Tyr Gly Arg Pro Phe Ser Ile Ile Cys Leu Lys Asn
                245                 250                 255
Ser Val Trp Thr Gly Ala Lys Asp Arg Cys Arg Arg Lys Ser Cys Arg
            260                 265                 270
Asn Pro Pro Asp Pro Val Asn Gly Met Val His Val Ile Lys Asp Ile
        275                 280                 285
Gln Phe Gly Ser Gln Ile Lys Tyr Ser Cys Thr Lys Gly Tyr Arg Leu
    290                 295                 300
Ile Gly Ser Ser Ser Ala Thr Cys Ile Ile Ser Gly Asn Thr Val Ile
305                 310                 315                 320
Trp Asp Asn Glu Thr Pro Ile Cys Asp Arg Ile Pro Cys Gly Leu Pro
                325                 330                 335
Pro Thr Ile Thr Asn Gly Asp Phe Ile Ser Thr Asn Arg Glu Asn Phe
            340                 345                 350
His Tyr Gly Ser Val Val Thr Tyr Arg Cys Asn Pro Gly Ser Gly Gly
        355                 360                 365
Arg Lys Val Phe Glu Leu Val Gly Glu Pro Ser Ile Tyr Cys Thr Ser
    370                 375                 380
Asn Asp Asp Gln Val Gly Ile Trp Ser Gly Pro Ala Pro Gln Cys Ile
385                 390                 395                 400
Gly Gly Gly Gly Gly Gly Asp Lys Thr His Thr Cys Pro Pro Cys Pro
                405                 410                 415
```

```
Ala Pro Glu Leu Leu Gly Gly Pro Ser Val Phe Leu Phe Pro Pro Lys
            420                 425                 430

Pro Lys Asp Thr Leu Met Ile Ser Arg Thr Pro Glu Val Thr Cys Val
        435                 440                 445

Val Val Asp Val Ser His Glu Asp Pro Glu Val Lys Phe Asn Trp Tyr
    450                 455                 460

Val Asp Gly Val Glu Val His Asn Ala Lys Thr Lys Pro Arg Glu Glu
465                 470                 475                 480

Gln Tyr Asn Ser Thr Tyr Arg Val Val Ser Val Leu Thr Val Leu His
                485                 490                 495

Gln Asp Trp Leu Asn Gly Lys Glu Tyr Lys Cys Lys Val Ser Asn Lys
            500                 505                 510

Ala Leu Pro Ala Pro Ile Glu Lys Thr Ile Ser Lys Ala Lys Gly Gln
        515                 520                 525

Pro Arg Glu Pro Gln Val Tyr Thr Leu Pro Pro Ser Arg Glu Glu Met
    530                 535                 540

Thr Lys Asn Gln Val Ser Leu Thr Cys Leu Val Lys Gly Phe Tyr Pro
545                 550                 555                 560

Ser Asp Ile Ala Val Glu Trp Glu Ser Asn Gly Gln Pro Glu Asn Asn
                565                 570                 575

Tyr Lys Thr Thr Pro Pro Val Leu Asp Ser Asp Gly Ser Phe Phe Leu
            580                 585                 590

Tyr Ser Lys Leu Thr Val Asp Lys Ser Arg Trp Gln Gln Gly Asn Val
        595                 600                 605

Phe Ser Cys Ser Val Met His Glu Ala Leu His Asn His Tyr Thr Gln
    610                 615                 620

Lys Ser Leu Ser Leu Ser Pro Gly
625                 630

<210> SEQ ID NO 36
<211> LENGTH: 632
<212> TYPE: PRT
<213> ORGANISM: Artificial Sequence
<220> FEATURE:
<223> OTHER INFORMATION: Synthetic construct

<400> SEQUENCE: 36

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140
```

```
Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Gly Gly Gly Arg Pro Phe Val Glu Met Tyr
225                 230                 235                 240

Ser Glu Ile Pro Glu Ile Ile His Met Thr Glu Gly Arg Glu Leu Val
                245                 250                 255

Ile Pro Cys Arg Val Thr Ser Pro Asn Ile Thr Val Thr Leu Lys Lys
            260                 265                 270

Phe Pro Leu Asp Thr Leu Ile Pro Asp Gly Lys Arg Ile Ile Trp Asp
        275                 280                 285

Ser Arg Lys Gly Phe Ile Ile Ser Asn Ala Thr Tyr Lys Glu Ile Gly
    290                 295                 300

Leu Leu Thr Cys Glu Ala Thr Val Asn Gly His Leu Tyr Lys Thr Asn
305                 310                 315                 320

Tyr Leu Thr His Arg Gln Thr Asn Thr Ile Ile Asp Val Val Leu Ser
                325                 330                 335

Pro Ser His Gly Ile Glu Leu Ser Val Gly Glu Lys Leu Val Leu Asn
            340                 345                 350

Cys Thr Ala Arg Thr Glu Leu Asn Val Gly Ile Asp Phe Asn Trp Glu
        355                 360                 365

Tyr Pro Ser Ser Lys His Gln His Lys Lys Leu Val Asn Arg Asp Leu
    370                 375                 380

Lys Thr Gln Ser Gly Ser Glu Met Lys Lys Phe Leu Ser Thr Leu Thr
385                 390                 395                 400

Ile Asp Gly Val Thr Arg Ser Asp Gln Gly Leu Tyr Thr Cys Ala Ala
                405                 410                 415

Ser Ser Gly Leu Met Thr Lys Lys Asn Ser Thr Phe Val Arg Val His
            420                 425                 430

Glu Lys Gly Gly Gly Gly Gly Gly Gln Cys Asn Ala Pro Glu Trp Leu
        435                 440                 445

Pro Phe Ala Arg Pro Thr Asn Leu Thr Asp Glu Phe Glu Phe Pro Ile
    450                 455                 460

Gly Thr Tyr Leu Lys Tyr Glu Cys Arg Pro Gly Tyr Tyr Gly Arg Pro
465                 470                 475                 480

Phe Ser Ile Ile Cys Leu Lys Asn Ser Val Trp Thr Gly Ala Lys Asp
                485                 490                 495

Arg Cys Arg Arg Lys Ser Cys Arg Asn Pro Pro Asp Pro Val Asn Gly
            500                 505                 510

Met Val His Val Ile Lys Asp Ile Gln Phe Gly Ser Gln Ile Lys Tyr
        515                 520                 525

Ser Cys Thr Lys Gly Tyr Arg Leu Ile Gly Ser Ser Ser Ala Thr Cys
    530                 535                 540

Ile Ile Ser Gly Asn Thr Val Ile Trp Asp Asn Glu Thr Pro Ile Cys
545                 550                 555                 560
```

```
Asp Arg Ile Pro Cys Gly Leu Pro Pro Thr Ile Asn Gly Asp Phe
            565                 570                 575

Ile Ser Thr Asn Arg Glu Asn Phe His Tyr Gly Ser Val Val Thr Tyr
            580                 585                 590

Arg Cys Asn Pro Gly Ser Gly Gly Arg Lys Val Phe Glu Leu Val Gly
            595                 600                 605

Glu Pro Ser Ile Tyr Cys Thr Ser Asn Asp Asp Gln Val Gly Ile Trp
            610                 615                 620

Ser Gly Pro Ala Pro Gln Cys Ile
625                 630

<210> SEQ ID NO 37
<211> LENGTH: 632
<212> TYPE: PRT
<213> ORGANISM: Artificial Sequence
<220> FEATURE:
<223> OTHER INFORMATION: Synthetic construct

<400> SEQUENCE: 37

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Gly Gly Gln Cys Asn Ala Pro Glu Trp Leu
225                 230                 235                 240

Pro Phe Ala Arg Pro Thr Asn Leu Thr Asp Glu Phe Glu Phe Pro Ile
                245                 250                 255

Gly Thr Tyr Leu Lys Tyr Glu Cys Arg Pro Gly Tyr Tyr Gly Arg Pro
            260                 265                 270

Phe Ser Ile Ile Cys Leu Lys Asn Ser Val Trp Thr Gly Ala Lys Asp
        275                 280                 285
```

-continued

Arg Cys Arg Arg Lys Ser Cys Arg Asn Pro Pro Asp Pro Val Asn Gly
290                 295                 300

Met Val His Val Ile Lys Asp Ile Gln Phe Gly Ser Gln Ile Lys Tyr
305                 310                 315                 320

Ser Cys Thr Lys Gly Tyr Arg Leu Ile Gly Ser Ser Ala Thr Cys
            325                 330                 335

Ile Ile Ser Gly Asn Thr Val Ile Trp Asp Asn Glu Thr Pro Ile Cys
                340                 345                 350

Asp Arg Ile Pro Cys Gly Leu Pro Pro Thr Ile Thr Asn Gly Asp Phe
            355                 360                 365

Ile Ser Thr Asn Arg Glu Asn Phe His Tyr Gly Ser Val Val Thr Tyr
370                 375                 380

Arg Cys Asn Pro Gly Ser Gly Gly Arg Lys Val Phe Glu Leu Val Gly
385                 390                 395                 400

Glu Pro Ser Ile Tyr Cys Thr Ser Asn Asp Asp Gln Val Gly Ile Trp
            405                 410                 415

Ser Gly Pro Ala Pro Gln Cys Ile Gly Gly Gly Gly Gly Gly Arg
                420                 425                 430

Pro Phe Val Glu Met Tyr Ser Glu Ile Pro Glu Ile Ile His Met Thr
            435                 440                 445

Glu Gly Arg Glu Leu Val Ile Pro Cys Arg Val Thr Ser Pro Asn Ile
450                 455                 460

Thr Val Thr Leu Lys Lys Phe Pro Leu Asp Thr Leu Ile Pro Asp Gly
465                 470                 475                 480

Lys Arg Ile Ile Trp Asp Ser Arg Lys Gly Phe Ile Ile Ser Asn Ala
            485                 490                 495

Thr Tyr Lys Glu Ile Gly Leu Leu Thr Cys Glu Ala Thr Val Asn Gly
            500                 505                 510

His Leu Tyr Lys Thr Asn Tyr Leu Thr His Arg Gln Thr Asn Thr Ile
            515                 520                 525

Ile Asp Val Val Leu Ser Pro Ser His Gly Ile Glu Leu Ser Val Gly
530                 535                 540

Glu Lys Leu Val Leu Asn Cys Thr Ala Arg Thr Glu Leu Asn Val Gly
545                 550                 555                 560

Ile Asp Phe Asn Trp Glu Tyr Pro Ser Ser Lys His Gln His Lys Lys
            565                 570                 575

Leu Val Asn Arg Asp Leu Lys Thr Gln Ser Gly Ser Glu Met Lys Lys
            580                 585                 590

Phe Leu Ser Thr Leu Thr Ile Asp Gly Val Thr Arg Ser Asp Gln Gly
            595                 600                 605

Leu Tyr Thr Cys Ala Ala Ser Ser Gly Leu Met Thr Lys Lys Asn Ser
610                 615                 620

Thr Phe Val Arg Val His Glu Lys
625                 630

<210> SEQ ID NO 38
<211> LENGTH: 204
<212> TYPE: PRT
<213> ORGANISM: Homo sapiens

<400> SEQUENCE: 38

Asp Thr Gly Arg Pro Phe Val Glu Met Tyr Ser Glu Ile Pro Glu Ile
1               5                   10                  15

Ile His Met Thr Glu Gly Arg Glu Leu Val Ile Pro Cys Arg Val Thr
                20                  25                  30

Ser Pro Asn Ile Thr Val Thr Leu Lys Lys Phe Pro Leu Asp Thr Leu
        35                  40                  45

Ile Pro Asp Gly Lys Arg Ile Ile Trp Asp Ser Arg Lys Gly Phe Ile
 50                  55                  60

Ile Ser Asn Ala Thr Tyr Lys Glu Ile Gly Leu Leu Thr Cys Glu Ala
 65                  70                  75                  80

Thr Val Asn Gly His Leu Tyr Lys Thr Asn Tyr Leu Thr His Arg Gln
                 85                  90                  95

Thr Asn Thr Ile Ile Asp Val Val Leu Ser Pro Ser His Gly Ile Glu
                100                 105                 110

Leu Ser Val Gly Glu Lys Leu Val Leu Asn Cys Thr Ala Arg Thr Glu
                115                 120                 125

Leu Asn Val Gly Ile Asp Phe Asn Trp Glu Tyr Pro Ser Ser Lys His
            130                 135                 140

Gln His Lys Lys Leu Val Asn Arg Asp Leu Lys Thr Gln Ser Gly Ser
145                 150                 155                 160

Glu Met Lys Lys Phe Leu Ser Thr Leu Thr Ile Asp Gly Val Thr Arg
                165                 170                 175

Ser Asp Gln Gly Leu Tyr Thr Cys Ala Ala Ser Ser Gly Leu Met Thr
                180                 185                 190

Lys Lys Asn Ser Thr Phe Val Arg Val His Glu Lys
            195                 200

<210> SEQ ID NO 39
<211> LENGTH: 227
<212> TYPE: PRT
<213> ORGANISM: Homo sapiens

<400> SEQUENCE: 39

Asp Lys Thr His Thr Cys Pro Pro Cys Pro Ala Pro Glu Leu Leu Gly
 1               5                  10                  15

Gly Pro Ser Val Phe Leu Phe Pro Pro Lys Pro Lys Asp Thr Leu Met
                 20                  25                  30

Ile Ser Arg Thr Pro Glu Val Thr Cys Val Val Val Asp Val Ser His
             35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
            130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met

His Glu Ala Leu His Asn His Tyr Thr Gln Lys Ser Leu Ser Leu Ser
210                 215                 220

Pro Gly Lys
225

<210> SEQ ID NO 40
<211> LENGTH: 629
<212> TYPE: PRT
<213> ORGANISM: Artificial Sequence
<220> FEATURE:
<223> OTHER INFORMATION: Synthetic construct

<400> SEQUENCE: 40

Asp Thr Gly Arg Pro Phe Val Glu Met Tyr Ser Glu Ile Pro Glu Ile
1               5                   10                  15

Ile His Met Thr Glu Gly Arg Glu Leu Val Ile Pro Cys Arg Val Thr
                20                  25                  30

Ser Pro Asn Ile Thr Val Thr Leu Lys Lys Phe Pro Leu Asp Thr Leu
            35                  40                  45

Ile Pro Asp Gly Lys Arg Ile Ile Trp Asp Ser Arg Lys Gly Phe Ile
50                  55                  60

Ile Ser Asn Ala Thr Tyr Lys Glu Ile Gly Leu Leu Thr Cys Glu Ala
65                  70                  75                  80

Thr Val Asn Gly His Leu Tyr Lys Thr Asn Tyr Leu Thr His Arg Gln
                85                  90                  95

Thr Asn Thr Ile Ile Asp Val Val Leu Ser Pro Ser His Gly Ile Glu
            100                 105                 110

Leu Ser Val Gly Glu Lys Leu Val Leu Asn Cys Thr Ala Arg Thr Glu
        115                 120                 125

Leu Asn Val Gly Ile Asp Phe Asn Trp Glu Tyr Pro Ser Ser Lys His
130                 135                 140

Gln His Lys Lys Leu Val Asn Arg Asp Leu Lys Thr Gln Ser Gly Ser
145                 150                 155                 160

Glu Met Lys Lys Phe Leu Ser Thr Leu Thr Ile Asp Gly Val Thr Arg
                165                 170                 175

Ser Asp Gln Gly Leu Tyr Thr Cys Ala Ala Ser Ser Gly Leu Met Thr
            180                 185                 190

Lys Lys Asn Ser Thr Phe Val Arg Val His Glu Lys Asp Lys Thr His
        195                 200                 205

Thr Cys Pro Pro Cys Pro Ala Pro Glu Leu Leu Gly Gly Pro Ser Val
210                 215                 220

Phe Leu Phe Pro Pro Lys Pro Lys Asp Thr Leu Met Ile Ser Arg Thr
225                 230                 235                 240

Pro Glu Val Thr Cys Val Val Val Asp Val Ser His Glu Asp Pro Glu
                245                 250                 255

Val Lys Phe Asn Trp Tyr Val Asp Gly Val Glu Val His Asn Ala Lys
            260                 265                 270

Thr Lys Pro Arg Glu Glu Gln Tyr Asn Ser Thr Tyr Arg Val Val Ser
        275                 280                 285

Val Leu Thr Val Leu His Gln Asp Trp Leu Asn Gly Lys Glu Tyr Lys
290                 295                 300

Cys Lys Val Ser Asn Lys Ala Leu Pro Ala Pro Ile Glu Lys Thr Ile
305                 310                 315                 320

Ser Lys Ala Lys Gly Gln Pro Arg Glu Pro Gln Val Tyr Thr Leu Pro

```
                325                 330                 335
Pro Ser Arg Asp Glu Leu Thr Lys Asn Gln Val Ser Leu Thr Cys Leu
            340                 345                 350
Val Lys Gly Phe Tyr Pro Ser Asp Ile Ala Val Glu Trp Glu Ser Asn
        355                 360                 365
Gly Gln Pro Glu Asn Asn Tyr Lys Thr Thr Pro Pro Val Leu Asp Ser
    370                 375                 380
Asp Gly Ser Phe Phe Leu Tyr Ser Lys Leu Thr Val Asp Lys Ser Arg
385                 390                 395                 400
Trp Gln Gln Gly Asn Val Phe Ser Cys Ser Val Met His Glu Ala Leu
                405                 410                 415
His Asn His Tyr Thr Gln Lys Ser Leu Ser Leu Ser Pro Gly Lys Gly
            420                 425                 430
Gly Gly Gly Gly Gly Gln Cys Asn Ala Pro Glu Trp Leu Pro Phe Ala
        435                 440                 445
Arg Pro Thr Asn Leu Thr Asp Glu Phe Glu Phe Pro Ile Gly Thr Tyr
    450                 455                 460
Leu Lys Tyr Glu Cys Arg Pro Gly Tyr Tyr Gly Arg Pro Phe Ser Ile
465                 470                 475                 480
Ile Cys Leu Lys Asn Ser Val Trp Thr Gly Ala Lys Asp Arg Cys Arg
                485                 490                 495
Arg Lys Ser Cys Arg Asn Pro Pro Asp Pro Val Asn Gly Met Val His
            500                 505                 510
Val Ile Lys Asp Ile Gln Phe Gly Ser Gln Ile Lys Tyr Ser Cys Thr
        515                 520                 525
Lys Gly Tyr Arg Leu Ile Gly Ser Ser Ser Ala Thr Cys Ile Ile Ser
    530                 535                 540
Gly Asn Thr Val Ile Trp Asp Asn Glu Thr Pro Ile Cys Asp Arg Ile
545                 550                 555                 560
Pro Cys Gly Leu Pro Pro Thr Ile Thr Asn Gly Asp Phe Ile Ser Thr
                565                 570                 575
Asn Arg Glu Asn Phe His Tyr Gly Ser Val Val Thr Tyr Arg Cys Asn
            580                 585                 590
Pro Gly Ser Gly Gly Arg Lys Val Phe Glu Leu Val Gly Glu Pro Ser
        595                 600                 605
Ile Tyr Cys Thr Ser Asn Asp Asp Gln Val Gly Ile Trp Ser Gly Pro
    610                 615                 620
Ala Pro Gln Cys Ile
625

<210> SEQ ID NO 41
<211> LENGTH: 227
<212> TYPE: PRT
<213> ORGANISM: Homo sapiens

<400> SEQUENCE: 41

Asp Lys Thr His Thr Cys Pro Pro Cys Pro Ala Pro Glu Leu Leu Gly
1               5                   10                  15
Gly Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
        35                  40                  45
Glu Asp Pro Glu Val Gln Phe Asn Trp Tyr Val Asp Gly Val Glu Val
    50                  55                  60
```

His Asn Ala Lys Thr Lys Pro Arg Glu Glu Gln Phe Asn Ser Thr Phe
 65                  70                  75                  80

Arg Val Val Ser Val Leu Thr Val Val His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Thr Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Met Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 42
<211> LENGTH: 227
<212> TYPE: PRT
<213> ORGANISM: Homo sapiens

<400> SEQUENCE: 42

Asp Lys Thr His Thr Cys Pro Pro Cys Pro Ala Pro Glu Leu Leu Gly
  1               5                  10                  15

Gly Pro Ser Val Phe Leu Phe Pro Pro Lys Pro Lys Asp Thr Leu Met
             20                  25                  30

Ile Ser Arg Thr Pro Glu Val Thr Cys Val Val Val Asp Val Ser His
         35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Asp Tyr Lys Cys Lys Val Ser Asn Lys Ala Leu Pro Ala Pro Met
            100                 105                 110

Gln Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Arg His Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

```
His Glu Ala Leu His Asn His Tyr Thr Gln Lys Ser Leu Ser Leu Ser
    210                 215                 220

Pro Gly Lys
225

<210> SEQ ID NO 43
<211> LENGTH: 20
<212> TYPE: PRT
<213> ORGANISM: Artificial Sequence
<220> FEATURE:
<223> OTHER INFORMATION: Synthetic construct

<400> SEQUENCE: 43

Met Glu Thr Asp Thr Leu Leu Leu Trp Val Leu Leu Leu Trp Val Pro
1               5                   10                  15

Gly Ser Thr Gly
            20

<210> SEQ ID NO 44
<211> LENGTH: 627
<212> TYPE: PRT
<213> ORGANISM: Artificial Sequence
<220> FEATURE:
<223> OTHER INFORMATION: Synthetic construct

<400> SEQUENCE: 44

Gly Arg Pro Phe Val Glu Met Tyr Ser Glu Ile Pro Glu Ile Ile His
1               5                   10                  15

Met Thr Glu Gly Arg Glu Leu Val Ile Pro Cys Arg Val Thr Ser Pro
            20                  25                  30

Asn Ile Thr Val Thr Leu Lys Lys Phe Pro Leu Asp Thr Leu Ile Pro
        35                  40                  45

Asp Gly Lys Arg Ile Ile Trp Asp Ser Arg Lys Gly Phe Ile Ile Ser
    50                  55                  60

Asn Ala Thr Tyr Lys Glu Ile Gly Leu Leu Thr Cys Glu Ala Thr Val
65                  70                  75                  80

Asn Gly His Leu Tyr Lys Thr Asn Tyr Leu Thr His Arg Gln Thr Asn
                85                  90                  95

Thr Ile Ile Asp Val Val Leu Ser Pro Ser His Gly Ile Glu Leu Ser
            100                 105                 110

Val Gly Glu Lys Leu Val Leu Asn Cys Thr Ala Arg Thr Glu Leu Asn
        115                 120                 125

Val Gly Ile Asp Phe Asn Trp Glu Tyr Pro Ser Ser Lys His Gln His
    130                 135                 140

Lys Lys Leu Val Asn Arg Asp Leu Lys Thr Gln Ser Gly Ser Glu Met
145                 150                 155                 160

Lys Lys Phe Leu Ser Thr Leu Thr Ile Asp Gly Val Thr Arg Ser Asp
                165                 170                 175

Gln Gly Leu Tyr Thr Cys Ala Ala Ser Ser Gly Leu Met Thr Lys Lys
            180                 185                 190

Asn Ser Thr Phe Val Arg Val His Glu Lys Asp Lys Thr His Thr Cys
        195                 200                 205

Pro Pro Cys Pro Ala Pro Glu Leu Leu Gly Gly Pro Ser Val Phe Leu
    210                 215                 220

Phe Pro Pro Lys Pro Lys Asp Thr Leu Met Ile Ser Arg Thr Pro Glu
225                 230                 235                 240

Val Thr Cys Val Val Val Asp Val Ser His Glu Asp Pro Glu Val Lys
```

```
            245                 250                 255
Phe Asn Trp Tyr Val Asp Gly Val Glu Val His Asn Ala Lys Thr Lys
            260                 265                 270

Pro Arg Glu Glu Gln Tyr Asn Ser Thr Tyr Arg Val Val Ser Val Leu
            275                 280                 285

Thr Val Leu His Gln Asp Trp Leu Asn Gly Lys Glu Tyr Lys Cys Lys
            290                 295                 300

Val Ser Asn Lys Ala Leu Pro Ala Pro Ile Glu Lys Thr Ile Ser Lys
305                 310                 315                 320

Ala Lys Gly Gln Pro Arg Glu Pro Gln Val Tyr Thr Leu Pro Pro Ser
            325                 330                 335

Arg Glu Glu Met Thr Lys Asn Gln Val Ser Leu Thr Cys Leu Val Lys
            340                 345                 350

Gly Phe Tyr Pro Ser Asp Ile Ala Val Glu Trp Glu Ser Asn Gly Gln
            355                 360                 365

Pro Glu Asn Asn Tyr Lys Thr Thr Pro Pro Val Leu Asp Ser Asp Gly
            370                 375                 380

Ser Phe Phe Leu Tyr Ser Lys Leu Thr Val Asp Lys Ser Arg Trp Gln
385                 390                 395                 400

Gln Gly Asn Val Phe Ser Cys Ser Val Met His Glu Ala Leu His Asn
            405                 410                 415

His Tyr Thr Gln Lys Ser Leu Ser Leu Ser Pro Gly Lys Gly Gly Gly
            420                 425                 430

Gly Gly Gly Gln Cys Asn Ala Pro Glu Trp Leu Pro Phe Ala Arg Pro
            435                 440                 445

Thr Asn Leu Thr Asp Glu Phe Glu Phe Pro Ile Gly Thr Tyr Leu Lys
450                 455                 460

Tyr Glu Cys Arg Pro Gly Tyr Tyr Gly Arg Pro Phe Ser Ile Ile Cys
465                 470                 475                 480

Leu Lys Asn Ser Val Trp Thr Gly Ala Lys Asp Arg Cys Arg Arg Lys
            485                 490                 495

Ser Cys Arg Asn Pro Pro Asp Pro Val Asn Gly Met Val His Val Ile
            500                 505                 510

Lys Asp Ile Gln Phe Gly Ser Gln Ile Lys Tyr Ser Cys Thr Lys Gly
            515                 520                 525

Tyr Arg Leu Ile Gly Ser Ser Ser Ala Thr Cys Ile Ile Ser Gly Asn
            530                 535                 540

Thr Val Ile Trp Asp Asn Glu Thr Pro Ile Cys Asp Arg Ile Pro Cys
545                 550                 555                 560

Gly Leu Pro Pro Thr Ile Thr Asn Gly Asp Phe Ile Ser Thr Asn Arg
            565                 570                 575

Glu Asn Phe His Tyr Gly Ser Val Val Thr Tyr Arg Cys Asn Pro Gly
            580                 585                 590

Ser Gly Gly Arg Lys Val Phe Glu Leu Val Gly Glu Pro Ser Ile Tyr
            595                 600                 605

Cys Thr Ser Asn Asp Asp Gln Val Gly Ile Trp Ser Gly Pro Ala Pro
            610                 615                 620

Gln Cys Ile
625
```

PROTEIN INHIBITORS TO COMPLEMENT AND VEGF PATHWAYS AND METHODS OF USE THEREOF

CROSS-REFERENCE TO RELATED PATENT APPLICATIONS

This Application is a National Phase application under 35 U.S.C. § 371 of International Application No. PCT/US2012/067489, filed Nov. 30, 2012, which claims the priority benefit of U.S. provisional application Ser. No. 61/629,932, filed Dec. 1, 2011, the contents of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 701672000100SEQLIST.txt, date recorded: Oct. 17, 2014, size: 89,832 bytes).

FIELD OF THE INVENTION

The present invention relates to bispecific fusion proteins that inhibit activation of the complement pathway and vascular endothelial growth factor (VEGF) pathway, compositions comprising these fusion proteins as well as methods for producing and using the same.

BACKGROUND OF THE INVENTION

The complement system is functional effector of the innate immune system consisting of a number of plasma proteins and cell membrane proteins. Activation of the complement leads to a series of protease activation cascade triggering release of cytokines and amplification of the activation cascade. The end result of the complement activation is activation of the cell-killing membrane attack complex (MAC), inflammation caused by anaphylatoxins C3a and C5a, and opsonization of pathogens. The MAC is essential for eliminating invading pathogens and damaged, necrotic, and apoptotic cells.

A delicate balance between defense against pathogen and avoidance of excess inflammation has to be achieved by complement system (Ricklin, D., et al., (2007). *Nature Biotechnology*, 25(11): 1265-1275). Many inflammatory, autoimmune, neurodegenerative and infectious diseases have been shown to be associated with excessive complement activity. For example, pathogenesis due to ischemia/reperfusion (I/R) injury has indicated that the complement activation leads to inflammation-induced damage in a number of diseases, including Acute Myocardial Infarction (AMI), Stroke, Hemorrhagic and Septic Shock, and complication of coronary artery bypass graft (CABG) surgery (Markiewski, M. M., et al, (2007). *Am. J. Pathol.* 171: 715-727). In addition, complement activation is a major contributor to a number of autoimmune diseases, including Systemic Lupus Erythematosus (Manderson, A. P., et al, (2004). *Annu. Rev. Immunol.* 22: 431-456), Rheumatoid Arthritis (RA), Psoriasis, and Asthma (Guo, R. F., et al, (2005). *Annu. Rev. Immunol.* 23: 821-852). Complement activation has also been correlated with the pathology of Alzheimer's disease (Bonifati, D. M., et al, (2007). *Mol. Immunol.* 44: 999-1010) and other neurodegenerative diseases such as Huntington's disease, Parkinson's disease, and age-related macular degeneration (AMD) (Gehrs, K. M., (2010). *Arch. Ophthalmol.*, 128 (3): 249-258).

The complement system can be activated through three different pathways: the classical pathway, the alternative pathway, and the lectin pathway. All three pathways go through critical protease complexes of C3-convertase and C5-convertase that cleave complement components C3 and C5, respectively. The classical pathway is initiated by binding of C1q to antibodies IgM or IgG leading to activation of the C1 complex that cleaves complement components C2 and C4, producing C2a, C2b, C4a, and C4b. C4b and C2b then forms the classical pathway C3-convertase, which promotes cleavage of C3 into C3a and C3b. C3b then forms the C5-convertase by binding to C4bC2b (the C3-convertase). The lectin pathway is identical to the classical pathway downstream of the C3-convertase, and is activated by binding of mannose-binding lectin (MBL) to mannose residues on the pathogen surface. The MBL-associated serine proteases MASP-1 and MASP-2 can then cleave C4 and C2 to form the same C3-convertase as in the classical pathway. Unlike the classical and the lectin pathways that are specific immune responses requiring antigens, the alternative pathway is a non-specific immune response that is continuously active at a low level. Spontaneously hydrolysis of C3 leads to C3a and C3b. C3b can bind Factor B and then cleave Factor B to Ba and Bb with facilitation of factor D. The C3bBb complex which can be stabilized by binding of Factor P (Properdin) is the C3-convertase of the alternative pathway that cleaves C3 to C3a and C3b. C3b can join the C3bBb complex to form C3bBbC3b complex that is the C5-convertase of the alternative pathway. The C5-convertases from all three pathways can cleave C5 to C5a and C5b. The C5b then recruits and assembles C6, C7, C7, C8 and multiple C9 molecules to assemble the MAC. This creates a hole or pore in the membrane that can kill or damage the pathogen or cell. The complement system is tightly regulated by two mechanisms: decay accelerating activity (DAA) and cofactor activity (CA). DAA refers to the ability to promoting dissociation of the C3-convertase or C5-convertase. CA refers to the ability of facilitating Factor I to cleave C3b or C4b to inactive fragments. For a review the complement system see Wagner, E., et al., (2010), *Nat. Rev. Drug Discov.*, 9(1): 43-56.

Human Complement Receptor type 1 (CR1) is the only complement regulator that has DAA for the both classical and alternative C3-convertases and C5-convertases and CA for C3b and C4b, and therefore has generated interest in therapeutic applications (Krych-Goldberg, M., et al, (2001), *Immunological Reviews*, 180: 112-122). A naturally occurred soluble human CR1 (sCR1) lacking the transmembrane and the intracellular domain have been shown to inhibit the complement system in vitro and various in vivo animal studies (Mollnes, T. E., et al, (2006), *Molecular Immunology*, 43: 107-121). sCR1 has also been tested in human clinical trials to reduce tissue damage in myocardial infarction (Perry, G. J., et al, (1998), *J. Am. Coll. Cardiol.*, 31: 41 1A), adult respiratory distress syndrome (Zimmerman, J. L., et al, (2000), *Crit. Care. Med.*, 28(9): 3149-3154), and lung transplantation (Zamora, M. R., et al, (1999), *Chest*, 116: 46s). It has been found safe, non-immunogenic, and efficacious in term of inhibiting complement activities in vivo. However, the molecular structure makes sCR1 difficult to produce as a therapeutic agent. Deletion mutagenesis has identified that the first 3 SCRs (SCR1-3) was sufficient to convey the DAA for the C3-convertases but not the CA for C3b and C4b (Krych-Goldberg, M., (1999), *J. Bio. Chem.*, 274(44): 31160-31168). Similar to CR1, complement regulatory proteins DAF, MCP, Factor H, and C4BP contain a number of SCRs where the binding sites of C3b or C4b and the active sites for complement inhibitions have been mapped (Makrides, S. C., (1998), *Pharmacological Reviews*, 50 (1): 59-87). Soluble forms of MCP, DAF, and Protectin have been produced and shown to be effective to inhibit complement in vitro and various animal models (Wagner, E., et al., (2010), *Nat. Rev. Drug Discov.*, 9(1): 43-56). However, they have relatively low potencies and short half-lives in vivo.

Vascular endothelial growth factor (VEGF) is one of the most important proteins that promote angiogenesis, which is a tightly regulated process of developing new blood vessels from a pre-existing vascular network (Ferrara, N., (2004), *Endocrine Reviews*, 25(4): 581-611). Angiogenesis is required during development and normal physiological processes such as wound healing, and is also involved in a number of disease pathogenesis, including AMD, RA, Diabetic Retinopathy, tumor growth and metastasis. Inhibition of angiogenesis has been shown to be effective in therapeutic applications.

The VEGF pathway and complement pathway both contribute to the formation of diseases with similar etiologies. Therefore there is a need for the development of therapeutic agents that target both the VEGF pathway and complement pathway. Provided herein are fusion proteins that inhibit activation of both the complement pathway and the VEGF pathway. Fusion proteins of the present invention can be used as therapeutic agent to for use in treatment of complement- and VEGF-related diseases.

BRIEF SUMMARY OF THE INVENTION

The invention provided herein discloses, inter alia, a fusion protein comprising a complement inhibiting domain (CID), a VEGF inhibiting domain (VID), and a half-life prolonging domain, compositions comprising fusion proteins, methods of making the fusion proteins, and methods of using these fusion proteins for inhibition of complement activation and the VEGF signaling pathway (e.g., inhibition of VEGF activity).

Accordingly, in one aspect, the invention provides for a fusion protein comprising a complement inhibiting domain (CID), a VEGF inhibiting domain (VID), and a half-life prolonging domain, wherein the fusion protein inhibits complement activation and VEGF signaling pathway (e.g., inhibition of VEGF activity). In one embodiment, the CID comprises at least one short consensus repeat (SCR) of a human complement regulatory protein selected from the group consisting of CR1, Factor H, C4-BP, DAF, and MCP. In a further embodiment, the CID comprises an amino acid sequence selected from the group consisting of SEQ ID NO:1-6 and 13-16, or an amino acid sequence having at least 90% identity to an amino acid sequence selected from the group consisting of SEQ ID NOs:1-6 and 13-16. In any of the embodiments herein, the VID comprises a portion of the extracellular domain of a human VEGF receptor. In one embodiment, the VID comprises an immunoglobulin-like (Ig) domain 2 of human VEGFR-1 and Ig-like domain 3 of human VEGFR-2. In a further embodiment, the VID comprises the amino acid sequence of SEQ ID NO:11 or 38, or an amino acid sequence having at least 90% identity to the amino acid sequence of SEQ ID NO:11 or 38. In any of the embodiments herein, the half-life prolonging domain comprises an immunoglobulin Fc region. In one embodiment, the Fc region is a human Fc of IgG1, IgG2, IgG3, or IgG4. In another embodiment, the Fc region comprises an amino acid sequence selected from the group consisting of SEQ ID NOs:7, 39, 41 and 42, or an amino acid sequence having at least 90% identity to the amino acid sequence selected from the group consisting of SEQ ID NOs:7, 39, 41 and 42. In any of the embodiments herein, the fusion protein further comprises a peptide linker between domains. In one embodiment, the peptide linker comprises the amino acid sequence of SEQ ID NO:8 or an amino acid sequence having at least 90% identity to the amino acid sequence of SEQ ID NO:8. In any of the embodiments herein, the fusion protein comprises said VID, CID, and Fc from N-terminal to C-terminal in an order selected from the group consisting of (1) VID, Fc, CID; (2) CID, Fc, VID; (3) CID, VID, Fc; (4) VID, CID, Fc; (5) Fc, VID, CID; and (6) Fc, CID, VID.

In another aspect, the invention provides for a fusion protein comprising, from the N-terminal to C-terminal, a VEGF inhibiting domain (VID), an immunoglobulin Fc region, and a complement inhibiting domain (CID), wherein the fusion protein inhibits complement activation and VEGF signaling pathway (e.g., inhibition of VEGF activity). In one embodiment, the CID comprises an amino acid sequence selected from the group consisting of SEQ ID NO:1-6 and 13-16, or an amino acid sequence having at least 90% identity to an amino acid sequence selected from the group consisting of SEQ ID NO:1-6 and 13-16. In any of the embodiments herein, the VID comprises a portion of the extracellular domain of a human VEGF receptor. In one embodiment, the VID comprises an immunoglobulin-like (Ig) domain 2 of human VEGFR-1 and Ig-like domain 3 of human VEGFR-2. In a further embodiment, the VID comprises the amino acid sequence of SEQ ID NO:11 or 38, or an amino acid sequence having at least 90% identity to the amino acid sequence of SEQ ID NO:11 or 38. In any of the embodiments herein, the Fc region is a human Fc of IgG1, IgG2, IgG3 or IgG4. In one embodiment, the Fc region comprises an amino acid sequence selected from the group consisting of SEQ ID NOs:7, 39, 41 and 42, or an amino acid sequence having at least 90% identity to the amino acid sequence selected from the group consisting of SEQ ID NOs:7, 39, 41 and 42. In any of the embodiments herein, the fusion protein further comprises a peptide linker between domains. In one embodiment, the peptide linker is between the Fc region and the CID. In a further embodiment, the peptide linker comprises the amino acid sequence of SEQ ID NO:8 or an amino acid sequence having at least 90% identity to the amino acid sequence of SEQ ID NO:8. In one embodiment, the fusion protein comprises the amino acid sequence selected from the group consisting of SEQ ID NOs:12, 33-37 and 40, or an amino acid sequence having at least 90% identity to the amino acid sequence selected from the group consisting of SEQ ID NOs:12, 33-37 and 40.

In another aspect, the invention provides a fusion protein produced by culturing a host cell comprising a nucleic acid encoding any fusion protein disclosed herein under a condition that produces the fusion protein, and recovering the fusion protein produced by the host cell. In one embodiment, the fusion protein comprises the amino acid sequence selected from the group consisting of SEQ ID NOs:12, 33-37 and 40, or an amino acid sequence having at least 90% identity to the amino acid sequence selected from the group consisting of SEQ ID NOs:12, 33-37 and 40. In a further embodiment, the fusion protein further comprises a signal peptide at its N-terminus comprising the amino acid sequence selected from the group consisting of SEQ ID NOs:9, 10 and 43. In a further embodiment, the recovered fusion protein produced by the host cell can comprise a signal peptide that is partially cleaved at the N-terminus. In one embodiment, the host cell is a mammalian cell. In a further embodiment, the mammalian cell is a CHO cell.

In another aspect, the invention provides a dimeric fusion protein (e.g., a dimeric Fc fusion protein) comprising two fusion proteins, wherein each fusion protein comprises any fusion protein disclosed herein. In one embodiment, the dimeric fusion protein comprises two identical fusion proteins. In another embodiment, the dimeric fusion protein comprises two different fusion proteins. In another embodiment, the dimeric fusion protein comprises at least one fusion protein comprising the amino acid sequence selected from the group consisting of SEQ ID NOs:12, 33-37 and 40, or an amino acid sequence having at least 90% identity to the amino acid sequence selected from the group consisting of SEQ ID NOs:12, 33-37 and 40.

In one aspect, the invention also provides for compositions comprising any fusion protein disclosed herein and a pharmaceutically acceptable carrier. In one embodiment, the fusion protein comprises the amino acid sequence selected from the group consisting of SEQ ID NOs:12, 33-37 and 40, or an amino acid sequence having at least 90% identity to the amino acid sequence selected from the group consisting of SEQ ID NOs:12, 33-37 and 40. In one embodiment, the fusion protein is a dimeric form. In further embodiment, the dimeric fusion protein comprises two identical fusion proteins. In another further embodiment, the dimeric fusion protein comprises two different fusion proteins. In another further embodiment, the dimeric fusion protein comprises at least one fusion protein comprising the amino acid sequence selected from the group consisting of SEQ ID NOs:12, 33-37 and 40, or an amino acid sequence having at least 90% identity to the amino acid sequence selected from the group consisting of SEQ ID NOs:12, 33-37 and 40.

In another aspect, the invention provides for a nucleic acid encoding any of the fusion proteins disclosed herein. In one embodiment, the nucleic acid encodes for a fusion protein comprises a complement inhibiting domain (CID), a VEGF inhibiting domain (VID), and a half-life prolonging domain, wherein the fusion protein inhibits complement activation and VEGF signaling pathway (e.g., inhibition of VEGF activity). In one embodiment, the nucleic acid encodes for a CID comprising at least one short consensus repeat (SCR) of a human complement regulatory protein selected from the group consisting of CR1, Factor H, C4-BP, DAF, and MCP. In a further embodiment, the nucleic acid encodes for a CID comprising an amino acid sequence selected from the group consisting of SEQ ID NO:1-6 and 13-16, or an amino acid sequence having at least 90% identity to an amino acid sequence selected from the group consisting of SEQ ID NO:1-6 and 13-16. In any of the embodiments herein, the nucleic acid encodes for a VID comprising a portion of the extracellular domain of a human VEGF receptor. In one embodiment, the nucleic acid encodes for a VID comprising an immunoglobulin-like (Ig) domain 2 of human VEGFR-1 and Ig-like domain 3 of human VEGFR-2. In a further embodiment, the nucleic acid encodes for a VID comprising the amino acid sequence of SEQ ID NO:11 or 38, or an amino acid sequence having at least 90% identity to the amino acid sequence of SEQ ID NO:11 or 38. In any of the embodiments herein, the nucleic acid encodes for a half-life prolonging domain comprising an immunoglobulin Fc region. In one embodiment, the nucleic acid encodes for an Fc region comprising the amino acid sequence selected from the group consisting of SEQ ID NOs:7, 39, 41 and 42, or an amino acid sequence having at least 90% identity to the amino acid sequence selected from the group consisting of SEQ ID NOs:7, 39, 41 and 42. In any of the embodiments herein, the nucleic acid further encodes a peptide linker comprising the amino acid sequence of SEQ ID NO:8 or an amino acid sequence having at least 90% identity to the amino acid sequence of SEQ ID NO:8. In any of the embodiments herein, the nucleic acid encodes for a fusion protein comprises the amino acid sequence selected from the group consisting of SEQ ID NOs:12, 33-37 and 40, or an amino acid sequence having at least 90% identity to the amino acid sequence selected from the group consisting of SEQ ID NOs:12, 33-37 and 40.

In another aspect, the invention provides for a vector comprising a nucleic acid encoding any of the fusion proteins disclosed herein. In one embodiment, the fusion protein comprises a complement inhibiting domain (CID), a VEGF inhibiting domain (VID), and a half-life prolonging domain, wherein the fusion protein inhibits complement activation and VEGF signaling pathway (e.g., inhibition of VEGF activity). In any of the embodiments herein, the vector comprises any of the nucleic acids disclosed herein that encode a fusion protein as described herein. In one embodiment, the vector comprises a nucleic acid encoding for a fusion protein comprising the amino acid sequence selected from the group consisting of SEQ ID NOs:12, 33-37 and 40, or an amino acid sequence having at least 90% identity to the amino acid sequence selected from the group consisting of SEQ ID NOs:12, 33-37 and 40. In any aspects, the invention provides a host cell comprises any of the nucleic acids disclosed here that encode a fusion protein as described herein. In one embodiment, the host cell comprises a nucleic acid encoding for a fusion protein comprising the amino acid sequence selected from the group consisting of SEQ ID NOs:12, 33-37 and 40, or an amino acid sequence having at least 90% identity to the amino acid sequence selected from the group consisting of SEQ ID NOs:12, 33-37 and 40.

In yet another aspect, the invention provides for a method of producing a fusion protein comprising culturing a host cell comprising a nucleic acid encoding any of the fusion proteins disclosed herein under a condition that produces the fusion protein, and recovering the fusion protein produced by the host cell. In one embodiment, the fusion protein is recovered from the cell culture medium and purified. In a further embodiment, the host cell is a mammalian cell or a yeast cell. In any of the embodiments herein, the fusion protein recovered is a dimer. In any of the embodiments herein, the fusion protein recovered is a partially cleaved fusion protein as described herein.

In another aspect, the invention provides for a method of treating a subject with an inflammatory disease, an autoimmune disease, an ocular disease or cancer, comprising administering to the subject an effective amount of any of the fusion proteins disclosed herein. In one embodiment, the fusion protein comprises a complement inhibiting domain (CID), a VEGF inhibiting domain (VID), and a half-life prolonging domain, wherein the fusion protein inhibits complement activation and VEGF signaling pathway (e.g., inhibition of VEGF activity). In one embodiment, the fusion protein comprises the amino acid sequence selected from the group consisting of SEQ ID NOs:12, 33-37 and 40, or an amino acid sequence having at least 90% identity to the amino acid sequence selected from the group consisting of SEQ ID NOs:12, 33-37 and 40. In one embodiment, the subject has rheumatoid arthritis, psoriasis, macular degeneration, diabetic retinopathy, retinal central vein occlusion, or corneal transplantation. In a further embodiment, the macular degeneration is wet age-related macular degeneration or dry age-related macular degeneration. In one embodiment, the subject has breast cancer, colorectal cancer, lung cancer, kidney cancer, gastric cancer, ovarian cancer, or retinoblastoma. In another embodiment, the method further comprises administering a second therapeutic agent for treating the disease.

In an additional aspect, the invention provides for a kit comprising any of the fusion proteins disclosed herein. In one embodiment, the fusion protein comprises a complement inhibiting domain (CID), a VEGF inhibiting domain (VID), and a half-life prolonging domain, wherein the fusion protein inhibits complement activation and VEGF signaling pathway (e.g., inhibition of VEGF activity). In one embodiment, the fusion protein comprises the amino acid sequence selected from the group consisting of SEQ ID NOs:12, 33-37 and 40, or an amino acid sequence having at least 90% identity to the amino acid sequence selected from the group consisting of SEQ ID NOs:12, 33-37 and 40. In one embodiment, the kit further comprises a package insert comprising instructions for use of the fusion protein for treating an inflammatory disease, an autoimmune disease, an ocular disease or cancer in a subject.

It is to be understood that one, some, or all of the properties of the various embodiments described herein may be combined to form other embodiments of the present invention. These and other aspects of the invention will become apparent to one of skill in the art.

DETAILED DESCRIPTION

Figure 1A:
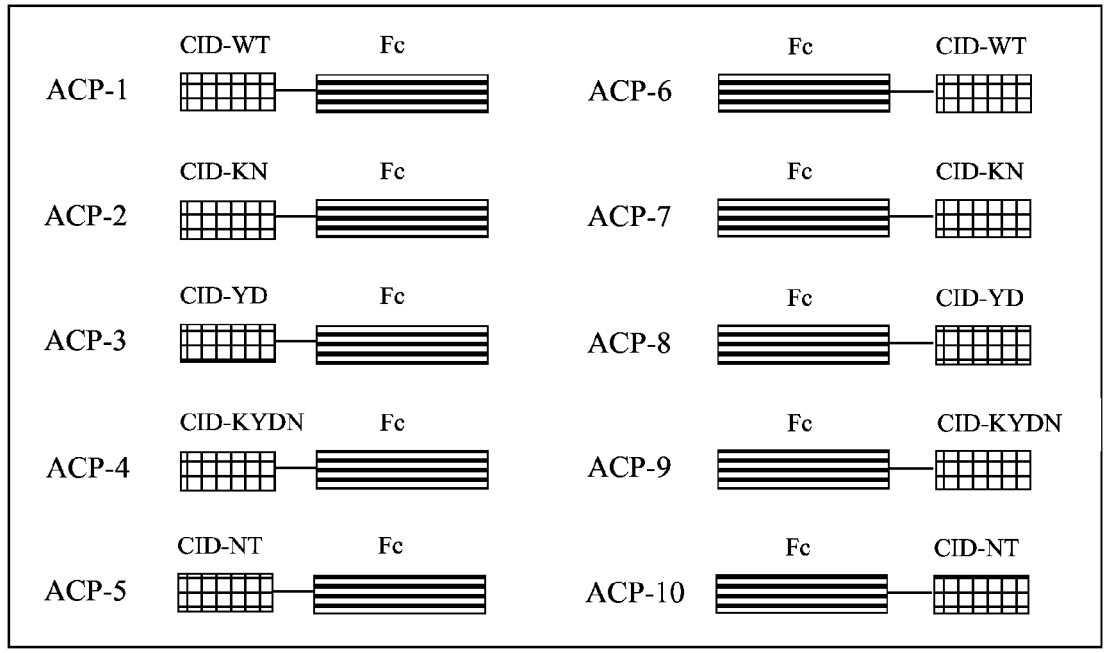
FIG. 1 provides schematic drawings of fusion proteins. A) Anti-complement proteins (ACPs), ACP-1 to ACP-10. CID-WT is human wild-type CR1 SCR1-3; CID-KN is human variant CR1 SCR1-3_N29K/D109N; CID-YD is human variant CR1 SCR1-3_S37Y/G79D; CID-KYDN is human variant CR1 SCR1-3_N29K/S37Y/G79D/D109N, CID-NT is human wild-type CR1 SCR8-10; and Fc is human IgG1 Fc region. B) Bispecific anti-complement/VEGF proteins (ACVPs), ACVP-1 to ACVP-6. CID is human variant CR1 SCR1-3_N29K/S37Y/G79D/D109N; VID is fusion of the $2^{nd}$ Ig-like domain of VEGFR1 and the $3^{rd}$ Ig-like domain of VEGFR2; and Fc is human IgG1 Fc region.

The present invention provides, inter alia, fusion proteins, and compositions thereof, that inhibit the complement pathway and the vascular endothelial growth factor (VEGF) pathway. A fusion protein of the invention as described herein comprises a complement inhibiting domain (CID), a VEGF inhibiting domain (VID), and a half-life prolonging domain, wherein the fusion protein inhibits complement activation and VEGF signaling pathway (e.g., inhibition of VEGF activity). Also provided herein are methods for production of the fusion proteins and methods of using the fusion proteins in the treatment of autoimmune diseases, complement-related diseases, inflammatory diseases, ocular diseases, and/or cancer.

I. General Techniques

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual, and Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclo-* nal *Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 1993).

II. Definitions

An "isolated" molecule (e.g., nucleic acid or protein) or cell is one which has been identified and separated and/or recovered from a component of its natural environment.

As used herein, "substantially pure" refers to material which is at least 50% pure (i.e., free from contaminants), more preferably at least 90% pure, more preferably at least 95% pure, more preferably at least 98% pure, more preferably at least 99% pure.

A "fusion polypeptide" or "fusion protein" (used interchangeably herein) refers to a polypeptide having two or more portions covalently linked together, where each of the portions is derived from different proteins. The two or more portions may be linked directly by a single peptide bond or through a peptide linker containing one or more amino acid residues. Generally, the two portions and the linker will be in reading frame with each other and are produced using recombinant techniques.

"Percent (%) amino acid or nucleotide sequence identity" with respect to a reference polypeptide or nucleic acid sequence is defined as the percentage of amino acid residues or nucleotides in a candidate sequence that are identical with the amino acid residues or nucleotides in the reference polypeptide or nucleic acid sequence, after aligning the sequences and introducing gaps, if necessary, to achieve the maximum percent sequence identity, and not considering any conservative substitutions as part of the sequence identity. Alignment for purposes of determining percent amino acid or nucleic acid sequence identity can be achieved in various ways that are within the skill in the art, for instance, using publicly available computer software such as BLAST, BLAST-2, ALIGN or Megalign (DNASTAR) software or those described in Ausubel et al., *Current Protocols in Molecular Biology*, John Wiley & Sons, New York, (2009). Those skilled in the art can determine appropriate parameters for aligning sequences, including any algorithms needed to achieve maximal alignment over the full length of the sequences being compared. For example, the Megalign (DNASTAR) program can create alignments between two or more sequences according to different methods, e.g., the clustal method. See, e.g., Higgins, D. G. and P. M. Sharp. (1988). *Gene*. 73:237-244. The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. See, e.g., Hein, J. (1990) *Methods Enzymol*. 183:626-645.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As used herein, "treatment" or "treating" is an approach for obtaining beneficial or desired results including and preferably clinical results. For purposes of this invention, beneficial or desired clinical results include, but are not limited to, one or more of the following: decreasing symptoms resulting from the disease, increasing the quality of life of those suffering from the disease, decreasing the dose of other medications required to treat the disease, delaying the progression of the disease, and/or prolonging survival of individuals.

As used herein, "delaying development of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In some embodiments, the individual or subject is a human.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject., A pharmaceutically acceptable carrier includes, but is not limited to, a buffer, excipient, stabilizer, or preservative.

An "effective amount or dosage" of an agent, e.g., a pharmaceutical formulation, refers to an amount effective, at dosages and for periods of time necessary, to achieve the desired therapeutic or prophylactic result. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective amount or dosage" may be considered in the context of administering one or more therapeutic agents, and a single agent may be considered to be given in an effective amount if, in conjunction with one or more other agents, a desirable result may be or is achieved.

As used herein, "in conjunction with" refers to administration of one treatment modality in addition to another treatment modality. As such, "in conjunction with" refers to administration of one treatment modality before, during or after administration of the other treatment modality to the individual.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein and in the appended claims, the singular forms "a," "an," and "the" include plural reference unless the context clearly indicates otherwise. For example, reference to an "fusion protein" or "fusion polypeptide" is a reference to from one to many fusion proteins or fusion polypeptides, such as molar amounts, and includes equivalents thereof known to those skilled in the art, and so forth.

Reference to "about" a value or parameter herein includes (and describes) embodiments that are directed to that value or parameter per se. For example, description referring to "about X" includes description of "X."

It is understood that embodiments, aspects and variations of the invention described herein include "consisting" and/or "consisting essentially of" embodiments, aspects and variations.

III. Fusion Proteins

The present invention provides fusion proteins that inhibit activation of the complement pathway and the VEGF pathway. In some embodiments, the complement pathway that is inhibited by the fusion protein may be the classical complement pathway, the alternative complement pathway, and/or the lectin pathway. In some embodiments, the VEGF pathway that is inhibited by the fusion proteins is mediated by VEGF receptors, e.g., VEGFR-1, VEGFR-2, and VEGFR-3. In some embodiments, the VEGF pathway that is inhibited by the fusion proteins is mediated by VEGF-A VEGF-B, VEGF-C, VEGF-D and PlGF. In some embodiments, the fusion proteins described herein inhibit complement activation and VEGF signaling pathway (e.g., inhibition of VEGF activity). The fusion proteins described herein comprise a complement inhibiting domain (CID), a VEGF inhibiting domain (VID), and a half-life prolonging domain.

Complement Inhibiting Domain (CID)

The present invention provides complement inhibiting domains (CIDs) that can be a component of any fusion polypeptide disclosed herein. The CID can comprise a polypeptide fragment of a complement regulating protein involved in the complement pathway which include members of the regulators of complement activation (RCA) and complement control proteins (CCP). In some embodiments, a CID comprises a fragment of a complement regulating protein that includes, but is not limited to, complement receptor 1 (CR1), Factor H, Decay-accelerating factor (DAF), membrane cofactor protein (MCP), and C4b-binding protein (C4BP). In any of the embodiments herein, the complement regulatory protein is from a mammal, such as a human, baboon, chimpanzee, mouse, or rat. In some embodiments, the complement regulatory protein is a human protein. Complement regulating proteins bind to components of the complement pathway including, but not limited to, C3b, C4b, iC3b, C3dg, C1q, and MBP. In some embodiments, the fragment of the complement regulating protein binds to a complement component (such as C3b, C4b, iC3b, C3dg, C1q, and MBP) and inhibits activation of the complement pathway (such as the classical pathway, the alternative pathway, and/or the lectin pathway). Methods of testing proteins that inhibit any of the complement pathways are known in the art and include the methods described in the examples (such as Examples 2, 3, and 6). See for example Scesney S. M., et al, (1996). *Eur. J. Immunol*, 26:1729-1735, which is incorporated herein in its entirety by reference. In some embodiments, the CID comprises at least one SCR of a human complement regulatory protein selected from the group consisting of CR1, Factor H, DAF, MCP, and C4BP.

The CID can comprise a portion of a complement regulating protein that binds to a complement component and inhibits complement activation. For example, human CR1 (allotype A) is a large glycoprotein (~200 kD) consisting of an extracellular domain comprising 30 repeating homologous short consensus repeats (SCR) each ranging from 60 to 70 amino acids, a transmembrane domain, and a cytoplasmic domain. The first 28 SCRs are organized into 4 long homologous repeat (LHR-A, -B, -C, and -D) of 7 SCRs each. The first 3 SCRs (SCR1-3) of the first LHR (LHR-A) binds to C4b with an intermediate affinity and C3b with a low affinity. The first 3 SCRs (SCR8-10) of the second LHR (LHR-B) and the first 3 SCRs (SCR15-17) of the third LHR (LHR-C) are nearly identical. They both bind C3b with a high affinity and C4b with an intermediate affinity. The LHR-A has high decay accelerating activity (DAA) for both the classical and alternative C3-convertases, but low cofactor activity (CA), whereas the LHR-B and LHR-C have high CA, but low DAA for the C3-convertases. Both LHR-A and LHR-B with appropriate spacing are required for DAA for the C5-convertases. Provided herein are CIDs comprising at least one SCR of a complement regulatory protein. In some embodiments, a CID comprises at least 1, 2, 3, 4, 5, 6, 7, 8, 9, 10, 11, 12, 13, 14 15, 16, 17, 18, 19, 20, 21, 22, 23, 24, 25, 26, 27, 28, 29 but no more than 30 SCRs of a complement regulatory protein. In some aspects, a CID comprises any one of 1 to 30, 1 to 29, 1 to 28, 1 to 27, 1 to 26, 1 to 25, 1 to 24, 1 to 23, 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9, 1 to 8, 1 to 7, 1 to 6, 1 to 5, 1 to 4, 1 to 3, or 1 to 2 SCRs of a complement regulatory protein. In some embodiments, a CID comprises one or more SCRs of a complement regulatory protein selected from the group consisting of, but is not limited to, CR1, Factor H, DAF, MCP, and C4BP. In some embodiments, a CID comprises at least one, at least two, at least three, at least four, at least five, at least six, at least seven, at least eight, at least nine, or at least ten SCR of CR1, Factor H, DAF, MCP, or C4BP. A CID comprising at least one SCR of two or more complement regulatory proteins is also contemplated. In some embodiments, a CID comprises at least one SCR from two or more complement regulatory proteins selected from the group consisting of CR1, Factor H, DAF, MCP, and C4BP.

Provided herein are CIDs comprising at least one SCR of any of the complement regulatory protein presented herein. Unless explicitly mentioned herein, SCRs are numbered sequentially from the N-terminus to C-terminus of the complement regulatory protein. For example, human CR1 contains 30 SCRs that are numbered 1 to 30 with SCR1 at the N-terminus of the human CR1 protein and SCR30 at the C-terminus of the human CR1 protein. In some embodiments, the CID comprises SCR1-10 of CR1, such as the amino acid sequence of SEQ ID NO:6. In other embodiments, the CID comprises SCR1-3 of CR1, such as the amino acid sequence of SEQ ID NO:1. In still other embodiments, the CID comprises SCR8-10 of CR1, such as the amino acid sequence of SEQ ID NO:5. In some embodiments, the CID comprises SCR2-4 of DAF, such as the amino acid sequence of SEQ ID NO:13. In other embodiments, the CID comprises SCR2-4 of MCP, such as the amino acid sequence of SEQ ID NO:14. In still other embodiments, the CID comprises SCR1-4 of Factor H. In some aspects, SCR1-4 of Factor H, such as the amino acid sequence of SEQ ID NO:15. In yet other embodiments, the CID comprises SCR1-3 of C4BPA, such as the amino acid sequence of SEQ ID NO:16. In any of the aspects herein, a CID can comprise an amino acid sequence selected from the group consisting of SEQ ID NO:1-6 and 13-16. Factor H SCR1-4 is a CID that specifically targets the alternative pathway but not the classical pathway. Since the classical complement pathway is required for antibody dependent pathogen clearance, therapeutic applications of a fusion protein containing a CID comprising Factor H SCR1-4 that inhibits only the alternative pathway might be a preferred fusion protein to limit potential side effect of serious infections.

The CIDs described in the present invention could be any peptide inhibitors or oligonucleotide inhibitors against Factor B, or Factor D, or Factor P, or C3, or C5. The CIDs could also be any full-length or fragments of antibodies, or the antibody variable regions (VH or VK), or the scFv antibodies derived from antibodies against Factor B, or Factor D, or Factor P, or C3, or C5.

In some embodiments, amino acid sequence variants of the CIDs provided herein are contemplated. For example, it may be desirable to improve the binding affinity and/or other biological properties of a CID. Amino acid sequence variants of a CID may be prepared by introducing appropriate modifications into the nucleotide sequence encoding the CID, or by peptide synthesis. Such modifications include, for example, deletions from, and/or insertions into and/or substitutions of residues within the amino acid sequences of the CID. Any combination of deletion, insertion, and substitution can be made to arrive at the final construct, provided that the final construct possesses the desired characteristics, e.g., binding to a complement component and inhibiting activation of complement pathway. Provided herein are variants of a CID that is a component of any fusion proteins disclosed herein. In some embodiments, a CID comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to an amino acid sequence selected from the group consisting of SEQ ID NOs:1-6 and 13-16.

In some aspects, the CID variant comprises one or more substitutions at amino acid residues selected from the group consisting of N29, S37, G79, and D109, wherein the amino acid residue position is relative to SEQ ID NO:1. In a particular embodiment, the CID variant comprises substitutions at amino acid residues N29 and D109, wherein the amino acid residue position is relative to SEQ ID NO:1. In another particular embodiment, the CID variant comprises substitutions at amino acid residues S37 and G79, wherein the amino acid residue position is relative to SEQ ID NO:1. In yet another particular embodiment, the CID variant comprises substitutions at amino acid residues N29, S37, G79, and D109, wherein the amino acid residue position is relative to SEQ ID NO:1. In some embodiments, the CID variant comprises substitutions at amino acid residues N29K, S37Y, G79D, and D109N, wherein the amino acid residue position is relative to SEQ ID NO:1. In some aspects, the CID variant comprises substitutions of any of the amino acid positions relative to SEQ ID NO:1 as shown in Table 1.

TABLE 1

| CID amino acid substitutions | | | | |
|---|---|---|---|---|
| | Amino acid substitutions (A) | | | |
| CID | A29 | A37 | A79 | A109 |
| CID-WT | N | S | G | D |
| CID-KN | K | S | G | N |
| CID-YD | N | Y | D | D |
| CID-KYDN | K | Y | D | N |

VEGF Inhibiting Domain (VID)

The present invention provides VEGF inhibiting domains (VIDs) that can be a component of any fusion protein disclosed herein. The human VEGF gene family contains five members: VEGF-A VEGF-B, VEGF-C, VEGF-D and placental growth factor (PlGF). In addition, multiple isoforms of VEGF-A, VEGF-B and PlGF are generated through alternative RNA splicing (Sullivan L. A., et al, (2010), MAbs, 2(2): 165-75). All members of the VEGF family stimulate cellular responses by binding to cell surface VEGF receptors (VEGFRs). For example, VEGF-A has been shown to stimulate endothelial cell mitogenesis, promote cell survival and proliferation, induce cell migration, and increase microvascular permeability. The VEGFR receptors are tyrosine kinase receptors that have extracellular regions consisting of 7 immunoglobulin (Ig)-like domains. VEGFR-1 (Flt-1) binds VEGF-A, -B, and PlGF, and can function as a decoy receptor for VEGFs or a regulator of VEGFR-2. VEGFR-2 (KDR/Flk-1) binds all VEGF isoforms and is the predominant mediator of VEGF-induced angiogenesis signaling). VEGFR-3 (Flt-4) binds VEGF-C and VEGF-D, but not VEGF-A, and functions as a mediator of lymphangiogenesis.

In any aspects of the invention disclosed herein, a VID comprises a polypeptide fragment of a VEGFR that includes, but is not limited to, VEGFR-1, VEGFR-2, and VEGFR-3. In some embodiments, a VID comprises a portion of the extracellular domain of a VEGFR that includes, but is not limited to, VEGFR-1, VEGFR-2, and VEGFR-3. In any of the embodiments herein, the VEGFR is from a mammal, such as a human, baboon, chimpanzee, mouse, or rat. In any of the aspects herein, a portion of the extracellular domain is an immunoglobulin-like (Ig) domain. For example, human VEGFR-1 contains seven Ig-like domains that are numbered 1, 2, 3, 4, 5, 6, and 7 with Ig-like domain 1 at the N-terminus of the extracellular domain and Ig-like domain 7 at the C-terminus of the extracellular domain. Unless explicitly mentioned herein, Ig-like domains are numbered sequentially from the N-terminus to C-terminus of the VEGFR protein. In some embodiments, a VID comprises at least one Ig-like domain of one or more VEGFRs selected from the group consisting of VEGFR-1, VEGFR-2, and VEGFR-3. In some aspects, a VID comprises at least 1, 2, 3, 4, 5, 6, but no more than 7 Ig-like domains of a VEGFR.

In a further aspect, a VID comprises 1 to 7, 1 to 6, 1 to 5, 1 to 4, 1 to 3, or 1 to 2 Ig-like domains of a VEGFR.

A VID comprising at least one Ig-like domain of two or more VEGFRs is contemplated herein. In some embodiments, a VID comprises at least one Ig-like from two or more VEGFRs selected from the group consisting of VEGFR-1, VEGFR-2, and VEGFR-3. In some aspects, a VID comprises at least 1, 2, 3, 4, 5, 6, 7, 8, 9, 10, 11, 12, 13, 14, 15, 16, 17, 18, 19, 20 but no more than 21 Ig-like domains of at least two or more VEGFRs. In a further aspect, a VID comprises 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9, 1 to 8, 1 to 7, 1 to 6, 1 to 5, 1 to 4, 1 to 3, or 1 to 2 Ig-like domains of at least two or more VEGFR. VIDs comprising any combination of the seven Ig-like domains of each VEGFR are contemplated herein. For example, a VID can comprise the Ig-like domain 2 of VEGFR-1 (e.g., human VEGFR-1) and Ig-like domain 3 of VEGFR-2 (e.g., human VEGFR-2). In another example, a VID can comprise the Ig-like domains 1-3 of VEGFR-1 (e.g., human VEGFR-1), the Ig-like domains 2-3 of VEGFR-1 (e.g., human VEGFR-1), the Ig-like domains 1-3 of VEGFR-2 (e.g., human VEGFR-2), the Ig-like domain 2 of VEGFR-1 (e.g., human VEGFR-1) and Ig-like domains 3-4 of VEGFR-2 (e.g., human VEGFR-2), or the Ig-like domain 2 of VEGFR-1 (e.g., human VEGFR-1) and Ig-like domain 3 of VEGFR-3 (e.g., human VEGFR-3). For a more detailed description of these Ig-like domains and other Ig-like domains that can be used as part of a VID, see U.S. Pat. No. 7,531,173, Yu, D., et al., (2012). *Mol. Ther.* 20(3):938-947, and Holash, J. et al., (2002). *PNAS.* 99(17):11393-11398, all of which are incorporated herein their entirety by reference. In some aspects, a VID comprises the amino acid sequence of SEQ ID NO:11. In some aspects, a VID comprises the amino acid sequence of SEQ ID NO:38. In some embodiments, a VID binds a vascular endothelial growth factor selected from the group consisting of VEGF-A, VEGF-B, VEGF-C, VEGF-D, and PlGF. As provided herein, a polypeptide or peptide that binds a vascular endothelial growth factor (e.g., VEGF-A, VEGF-B, VEGF-C, VEGF-D, and PlGF) or that binds a VEGFR (e.g., VEGFR-1, VEGFR-2, and VEGFR-3) to inhibit activation of a VEGF pathway is a VID. For example, a VID can comprise an antibody or fragment thereof (e.g., Fab, Fab', Fab-SH, Fv, scFv or F(ab')$_2$), a natural peptide, or a synthetic peptide that binds a vascular endothelial growth factor (e.g., VEGF-A, VEGF-B, VEGF-C, VEGF-D, and PlGF) and blocks its interaction with VEGFR. In some aspects, a VID is an antibody or fragment thereof (e.g., Fab, Fab', Fab-SH, Fv, scFv or F(ab')$_2$), a natural peptide, or a synthetic peptide that binds a VEGFR (e.g., VEGFR-1, VEGFR-2, and VEGFR-3) and blocks its interaction with VEGF. In some aspects, the VID is acetylated. In any of the embodiments herein, the VID is from a mammal, such as a human, baboon, chimpanzee, mouse, or rat.

The VIDs of the present invention could be any extracellular domain of VEGFRs, dominate negative forms of VEGF family members, antibodies against VEGF family members, antibodies against VEGFRs, peptide inhibitors to VEGF family members or VEGFRs, oligonucleotide inhibitors to VEGF family members or VEGFRs.

In some embodiments, amino acid sequence variants of any VIDs provided herein are contemplated. For example, it may be desirable to improve the binding affinity and/or other biological properties of the VID. Amino acid sequence variants of a VID may be prepared by introducing appropriate modifications into the nucleotide sequence encoding the VID, or by peptide synthesis. Such modifications include, for example, deletions from, and/or insertions into and/or substitutions of residues within the amino acid sequences of the VID. Any combination of deletion, insertion, and substitution can be made to arrive at the final construct, provided that the final construct possesses the desired characteristics, e.g., binding to a VEGF and inhibiting activation of the VEGF pathway. Provided herein are variants of VID that can be a component of any fusion polypeptide disclosed herein. In some embodiments, a VID comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to an amino acid sequence for any one of Ig-like domains 1, 2, 3, 4, 5, 6 or 7 of VEGFR-1 (e.g., human VEGFR-1). In some embodiments, a VID comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence for any one of Ig-like domains 1, 2, 3, 4, 5, 6 or 7 of VEGFR-2 (e.g., human VEGFR-2). In some embodiments, a VID comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence for any one of Ig-like domains 1, 2, 3, 4, 5, 6 or 7 of VEGFR-3. In some embodiments, a VID comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence to an amino acid sequence selected from the group consisting of SEQ ID NOs:11 and 38.

Half-Life Prolonging Domain

The present invention provides a half-life prolonging domain that can be a component of any fusion protein disclosed herein. For example, Fc regions from an immunoglobulin can be incorporated into a fusion polypeptide to increase half-life in vivo. A half-life prolonging domain can comprise an Fc region from any immunoglobulin isotype, subclass, or allotype. In some embodiments, the half-life prolonging domain is an Fc region from an immunoglobulin isotype selected from the group consisting of IgG, IgA, IgD, IgM, and IgE. In some embodiments, the half-life prolonging domain comprises an immunoglobulin Fc region. In some aspects, the Fc region is a human Fc of IgG1, IgG2, IgG3 or IgG4. In some aspects, the Fc region is a human Fc of IgA1 or IgA2. In some aspects, the Fc region is a human Fc of IgD. In some aspects, the Fc region is a human Fc of IgE. In some aspects, the Fc region is a human Fc of IgM. In some aspects, the Fc region is glycosylated. In some embodiments, the Fc region comprises the amino acid sequence selected from the group consisting of SEQ ID NOs:7, 39, 41, and 42. In any of the aspects provided herein, the half-life prolonging domain can be a polypeptide or fragment thereof selected from the group consisting of, but not limited to, an antibody, albumin, or protease inhibitor (e.g., alpha 1-antitrypsin). In any of the aspects provided herein, the half-life prolonging domain can be an amino acid sequence selected from the group consisting of, but not limited to, a glycine-rich amino acid sequence, PESTAG sequence, or PAS sequence. The half-life prolonging domain can be any polypeptide or amino acid sequence known in the art to increase the half-life of a polypeptide in vivo. See Kontermann, R. (Ed.) (2011). Therapeutic Proteins: Strategies to Modulate their Plasma Half-lives, which is incorporated herein by reference in its entirety. In any of the embodiments herein, the half-life prolonging domain is from a mammal, such as a human, baboon, chimpanzee, mouse, or rat.

In some embodiments, amino acid sequence variants of the half-life prolonging domains provided herein are contemplated. For example, it may be desirable to improve the biological properties of the half-life prolonging domain. Amino acid sequence variants of a half-life prolonging domain may be prepared by introducing appropriate modifications into the nucleotide sequence encoding the half-life prolonging domain, or by peptide synthesis. Such modifications include, for example, deletions from, and/or insertions into and/or substitutions of residues within the amino acid sequences of the half-life prolonging domain. Any combination of deletion, insertion, and substitution can be made to arrive at the final construct, provided that the final construct possesses the desired characteristics, e.g., prolonging half-life of the fusion protein. Provided herein are variants of a half-life prolonging domain that can be a component of any fusion polypeptide disclosed herein. In some embodiments, the half-life prolonging domain variant is an Fc region variant. Variants of the Fc region are known in the art, for example U.S. Patent Application Publication No. 2010/02493852, and U.S. patent application publication number 2006/01341105, which are incorporated herein by reference in their entirety. In some embodiments, one or more amino acid modifications may be introduced into the Fc region of a fusion polypeptide provided herein, thereby generating an Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions. In some embodiments, the Fc region comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to an amino acid sequence selected from the group consisting of SEQ ID NOs:7, 39, 41, and 42. In some embodiments, the Fc region variant is glycosylated.

Fusion Peptide Linker

The present invention provides a linker that can be a component of any fusion protein disclosed herein. For example, short flexible peptides can be used between the domains (e.g., CID, VID, and half-life prolonging domain) of the fused polypeptide to ensure correct folding of each domain and to minimize steric hindrance. In some embodiments, the linker is a peptide linker. In some embodiments, the linker is a peptide comprised of amino acids selected from the group consisting of glycine, alanine, and serine. In some embodiments, the linker comprises 2 to 100 amino acids. In other embodiments, the linker comprises 100 amino acids or less. In some embodiments, the linker comprises 20 or less amino acids. In some embodiments, the linker comprises 15 or less amino acids. In some embodiments, the peptide linker comprises 10 or less amino acids. In some embodiments, the linker comprises 6 or less amino acids. In some aspects, the linker comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, but no greater than 100 amino acids. In some embodiments, the linker comprises the amino acid sequence of SEQ ID NO:8. In some embodiments, the linker is used between the CID and half-life prolonging domain. In some embodiments, the linker is used between the VID and the half-life prolonging domain. In other embodiments, the linker is used between the VID and CID. In still other embodiments, the linker is used between the both the VID and half-life prolonging domain and the CID and half-life prolonging domain. In other embodiments, the linker is used between the both the VID and CID and the CID and half-life prolonging domain. In some embodiments, the linker is used between the both the CID and VID and the VID and half-life prolonging domain. In some embodiments, a fusion polypeptide comprises at least one linker but no more than four linkers. For example, a fusion polypeptide can comprise a CID, a VID, an Fc region (Fc), and at least one linker from N-terminal to C-terminal in an order selected from the group consisting of (1) VID, Fc, linker, CID; (2) CID, linker, Fc, linker, VID; (3) CID, linker, VID, Fc; (4) VID, linker, CID, linker, Fc; (5) Fc, linker, VID, linker, CID; and (6) Fc, linker, CID, linker, VID. In some embodiments, the fusion polypeptide comprises a CID, a VID, Fc, and linker from N-terminal to C-terminal in an order of VID, Fc, linker, CID.

Fusion Proteins

As disclosed herein fusion proteins are polypeptides that have binding specificities for two different target binding partners. In some embodiments, fusion polypeptides are human polypeptides. In some embodiments, fusion polypeptides comprise a first binding specificity to a component of the complement pathway (e.g., C3b, C4b, iC3b, C3dg, C1q, or MBP) and a second binding specificity to a VEGF (e.g., VEGF-A VEGF-B, VEGF-C, VEGF-D, or PlGF). In some embodiments, the fusion polypeptide comprises a first binding specificity to a mammalian (e.g., human) component of the complement pathway and a second binding specificity to a mammalian (e.g., human) VEGF. In some embodiments, fusion polypeptides bind to the same component of the complement pathway as any of the complement regulating proteins described herein. In some embodiments, fusion polypeptides bind to the same component of the complement pathway as any one of CR1, Factor H, DAF, MCP, or C4BP. In some embodiments, fusion polypeptides comprise at least one CID of any of the CIDs described herein. In some aspects, a fusion polypeptide comprises a CID comprising the amino acid sequence selected from the group consisting of SEQ ID NOs:1-6 and 13-16. In some embodiments, fusion polypeptides bind to the same component of the VEGF pathway as any of the VEGFRs described herein. In some embodiments, fusion polypeptides bind to the same component of the VEGF pathway as any one of VEGFR-1, VEGFR-2, or VEGFR-3. In some embodiments, fusion polypeptides comprise at least one VID of any of the VIDs described herein. In some aspects, a fusion polypeptide comprises a VID comprising the amino acid sequence of SEQ ID NO:11. In other aspects, a fusion polypeptide comprises a VID comprising the amino acid sequence of SEQ ID NO:38. Any of the fusion polypeptides disclosed herein comprising a CID and a VID can further comprise a half-life prolonging domain. In some embodiments, the half-life prolong domain is an Fc region. In some embodiments, the Fc region comprises the amino acid sequence selected from the group consisting of SEQ ID NOs:7, 39, 41, and 42. In some embodiments, the fusion polypeptide comprising a CID, a VID, and a half-life prolonging domain inhibits complement activation and VEGF signaling path way (e.g., inhibition of VEGF activity). Any of the fusion polypeptides disclosed herein comprising a CID, a VID, and a half-life prolonging domain can further comprise a linker. In some embodiments, the linker comprises the amino acid sequence of SEQ ID NO:8. In some embodiments, the CID comprises at least one short SCR of a mammalian (e.g., human) complement regulatory protein. In further embodiments, the VID comprises a portion of the extracellular domain of a mammalian (e.g., human) VEGFR. In some embodiments, the fusion polypeptide comprises a CID comprising at least one short SCR of a human complement regulatory protein and a VID comprising a portion of the extracellular domain of a human VEGFR. In one aspect, the invention provides a fusion polypeptide comprising:

a) a CID comprising the amino acid sequence of
(SEQ ID NO: 4)
QCNAPEWLPFARPTNLTDEFEFPIGTYLKYECRPGYYGRPFSIICLKNSVWTGAKDRC

RRKSCRNPPDPVNGMVHVIKDIQFGSQIKYSCTKGYRLIGSSSATCIISGNTVIWDNET

PICDRIPCGLPPTITNGDFISTNRENFHYGSVVTYRCNPGSGGRKVFELVGEPSIYCTSN

DDQVGIWSGPAPQCI;

b) a VID comprising the amino acid sequence of
(SEQ ID NO: 11)
GRPFVEMYSEIPEIIHMTEGRELVIPCRVTSPNITVTLKKFPLDTLIPDGKRIIWDSRKG

FIISNATYKEIGLLTCEATVNGHLYKTNYLTHRQTNTIIDVVLSPSHGIELSVGEKLVL

NCTARTELNVGIDFNWEYPSSKHQHKKLVNRDLKTQSGSEMKKFLSTLTIDGVTRSD

QGLYTCAASSGLMTKKNSTFVRVHEK;
and c) a half-life prolonging domain comprising the amino acid sequence of
(SEQ ID NO: 39)
DKTHTCPPCPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQKSLSLSPGK.

In another aspect, the invention provides a fusion polypeptide comprising:

a) a CID comprising the amino acid sequence of
(SEQ ID NO: 4)
QCNAPEWLPFARPTNLTDEFEFPIGTYLKYECRPGYYGRPFSIICLKNSVWTGAKDRC

RRKSCRNPPDPVNGMVHVIKDIQFGSQIKYSCTKGYRLIGSSSATCIISGNTVIWDNET

PICDRIPCGLPPTITNGDFISTNRENFHYGSVVTYRCNPGSGGRKVFELVGEPSIYCTSN

DDQVGIWSGPAPQCI;

b) a VID comprising the amino acid sequence of
(SEQ ID NO: 38)
DTGRPFVEMYSEIPEIIHMTEGRELVIPCRVTSPNITVTLKKFPLDTLIPDGKRIIWDSR

KGFIISNATYKEIGLLTCEATVNGHLYKTNYLTHRQTNTIIDVVLSPSHGIELSVGEKL

VLNCTARTELNVGIDFNWEYPSSKHQHKKLVNRDLKTQSGSEMKKFLSTLTIDGVTR

SDQGLYTCAASSGLMTKKNSTFVRVHEK;
and c) a half-life prolonging domain comprising the amino acid sequence of
(SEQ ID NO: 39)
DKTHTCPPCPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKALPAPIE

KTISKAKGQPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQKSLSLSPGK.

Provided herein are fusion polypeptides comprising a CID, a VID and a half-long prolonging domain in any order. For example, a fusion polypeptide can comprise a CID, a VID, and a Fc region (Fc) from N-terminal to C-terminal in an order selected from the group consisting of (1) VID, Fc, CID; (2) CID, Fc, VID; (3) CID, VID, Fc; (4) VID, CID, Fc; (5) Fc, VID, CID; and (6) Fc, CID, VID. In some embodiments, the fusion polypeptide comprises a CID, a VID, and Fc from N-terminal to C-terminal in an order of VID, Fc, CID. In some embodiments, the fusion polypeptide comprises the amino acid sequence of:

```
                                                    (SEQ ID NO: 12)
GRPFVEMYSEIPEIIHMTEGRELVIPCRVTSPNITVTLKKFPLDTLIPDGKRIIWDSRKG

FIISNATYKEIGLLTCEATVNGHLYKTNYLTHRQTNTIIDVVLSPSHGIELSVGEKLVL

NCTARTELNVGIDFNWEYPSSKHQHKKLVNRDLKTQSGSEMKKFLSTLTIDGVTRSD

QGLYTCAASSGLMTKKNSTFVRVHEKDKTHTCPPCPAPELLGGPSVFLFPPKPKDTL

MISRTPEVTCVVVDVSHEDPEVKFNWYVDGVEVHNAKTKPREEQYNSTYRVVSVLT

VLHQDWLNGKEYKCKVSNKALPAPIEKTISKAKGQPREPQVYTLPPSREEMTKNQVS

LTCLVKGFYPSDIAVEWESNGQPENNYKTTPPVLDSDGSFFLYSKLTVDKSRWQQG

NVFSCSVMHEALHNHYTQKSLSLSPGKGGGGGGQCNAPEWLPFARPTNLTDEFEFPI

GTYLKYECRPGYYGRPFSIICLKNSVWTGAKDRCRRKSCRNPPDPVNGMVHVIKDIQ

FGSQIKYSCTKGYRLIGSSSATCIISGNTVIWDNETPICDRIPCGLPPTITNGDFISTNRE

NFHYGSVVTYRCNPGSGGRKVFELVGEPSIYCTSNDDQVGIWSGPAPQCI.
```

In other embodiments, the fusion polypeptide comprises the amino acid sequence of:

```
                                                    (SEQ ID NO: 33)
QCNAPEWLPFARPTNLTDEFEFPIGTYLKYECRPGYYGRPFSIICLKNSVWTGAKDRC

RRKSCRNPPDPVNGMVHVIKDIQFGSQIKYSCTKGYRLIGSSSATCIISGNTVIWDNET

PICDRIPCGLPPTITNGDFISTNRENFHYGSVVTYRCNPGSGGRKVFELVGEPSIYCTSN

DDQVGIWSGPAPQCIGGGGGGDKTHTCPPCPAPELLGGPSVFLFPPKPKDTLMISRTP

EVTCVVVDVSHEDPEVKFNWYVDGVEVHNAKTKPREEQYNSTYRVVSVLTVLHQD

WLNGKEYKCKVSNKALPAPIEKTISKAKGQPREPQVYTLPPSREEMTKNQVSLTCLV

KGFYPSDIAVEWESNGQPENNYKTTPPVLDSDGSFFLYSKLTVDKSRWQQGNVFSCS

VMHEALHNHYTQKSLSLSPGKGGGGGGRPFVEMYSEIPEIIHMTEGRELVIPCRVTS

PNITVTLKKFPLDTLIPDGKRIIWDSRKGFIISNATYKEIGLLTCEATVNGHLYKTNYLT

HRQTNTIIDVVLSPSHGIELSVGEKLVLNCTARTELNVGIDFNWEYPSSKHQHKKLVN

RDLKTQSGSEMKKFLSTLTIDGVTRSDQGLYTCAASSGLMTKKNSTFVRVHEK.
```

In still other embodiments, the fusion polypeptide comprises the amino acid sequence of:

```
                                                    (SEQ ID NO: 34)
QCNAPEWLPFARPTNLTDEFEFPIGTYLKYECRPGYYGRPFSIICLKNSVWTGAKDRC

RRKSCRNPPDPVNGMVHVIKDIQFGSQIKYSCTKGYRLIGSSSATCIISGNTVIWDNET

PICDRIPCGLPPTITNGDFISTNRENFHYGSVVTYRCNPGSGGRKVFELVGEPSIYCTSN

DDQVGIWSGPAPQCIGGGGGGRPFVEMYSEIPEIIHMTEGRELVIPCRVTSPNITVTL

KKFPLDTLIPDGKRIIWDSRKGFIISNATYKEIGLLTCEATVNGHLYKTNYLTHRQTNT

IIDVVLSPSHGIELSVGEKLVLNCTARTELNVGIDFNWEYPSSKHQHKKLVNRDLKTQ

SGSEMKKFLSTLTIDGVTRSDQGLYTCAASSGLMTKKNSTFVRVHEKDKTHTCPPCP

APELLGGPSVFLFPPKPKDTLMISRTPEVTCVVVDVSHEDPEVKFNWYVDGVEVHNA
```

-continued

KTKPREEQYNSTYRVVSVLTVLHQDWLNGKEYKCKVSNKALPAPIEKTISKAKGQP

REPQVYTLPPSREEMTKNQVSLTCLVKGFYPSDIAVEWESNGQPENNYKTTPPVLDS

DGSFFLYSKLTVDKSRWQQGNVFSCSVMHEALHNHYTQKSLSLSPGK.

In yet other embodiments, the fusion polypeptide comprises the amino acid sequence of:

(SEQ ID NO: 35)
GRPFVEMYSEIPEIIHMTEGRELVIPCRVTSPNITVTLKKFPLDTLIPDGKRIIWDSRKG

FIISNATYKEIGLLTCEATVNGHLYKTNYLTHRQTNTIIDVVLSPSHGIELSVGEKLVL

NCTARTELNVGIDFNWEYPSSKHQHKKLVNRDLKTQSGSEMKKFLSTLTIDGVTRSD

QGLYTCAASSGLMTKKNSTFVRVHEKGGGGGGQCNAPEWLPFARPTNLTDEFEFPI

GTYLKYECRPGYYGRPFSIICLKNSVWTGAKDRCRRKSCRNPPDPVNGMVHVIKDIQ

FGSQIKYSCTKGYRLIGSSSATCIISGNTVIWDNETPICDRIPCGLPPTITNGDFISTNRE

NFHYGSVVTYRCNPGSGGRKVFELVGEPSIYCTSNDDQVGIWSGPAPQCIGGGGGGD

KTHTCPPCPAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALPAPIEK

TISKAKGQPREPQVYTLPPSREEMTKNQVSLTCLVKGFYPSDIAVEWESNGQPENNY

KTTPPVLDSDGSFFLYSKLTVDKSRWQQGNVFSCSVMHEALHNHYTQKSLSLSPG.

In other embodiments, the fusion polypeptide comprises the amino acid sequence of:

(SEQ ID NO: 36)
DKTHTCPPCPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKALPAPIE

KTISKAKGQPREPQVYTLPPSREEMTKNQVSLTCLVKGFYPSDIAVEWESNGQPENN

YKTTPPVLDSDGSFFLYSKLTVDKSRWQQGNVFSCSVMHEALHNHYTQKSLSLSPG

GGGGGGGRPFVEMYSEIPEIIHMTEGRELVIPCRVTSPNITVTLKKFPLDTLIPDGKRII

WDSRKGFIISNATYKEIGLLTCEATVNGHLYKTNYLTHRQTNTIIDVVLSPSHGIELSV

GEKLVLNCTARTELNVGIDFNWEYPSSKHQHKKLVNRDLKTQSGSEMKKFLSTLTID

GVTRSDQGLYTCAASSGLMTKKNSTFVRVHEKGGGGGGQCNAPEWLPFARPTNLT

DEFEFPIGTYLKYECRPGYYGRPFSIICLKNSVWTGAKDRCRRKSCRNPPDPVNGMV

HVIKDIQFGSQIKYSCTKGYRLIGSSSATCIISGNTVIWDNETPICDRIPCGLPPTITNGD

FISTNRENFHYGSVVTYRCNPGSGGRKVFELVGEPSIYCTSNDDQVGIWSGPAPQCI.

In other embodiments, the fusion polypeptide comprises the amino acid sequence of:

(SEQ ID NO: 37)
DKTHTCPPCPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKALPAPIE

KTISKAKGQPREPQVYTLPPSREEMTKNQVSLTCLVKGFYPSDIAVEWESNGQPENN

YKTTPPVLDSDGSFFLYSKLTVDKSRWQQGNVFSCSVMHEALHNHYTQKSLSLSPG

GGGGGGQCNAPEWLPFARPTNLTDEFEFPIGTYLKYECRPGYYGRPFSIICLKNSVWT

GAKDRCRRKSCRNPPDPVNGMVHVIKDIQFGSQIKYSCTKGYRLIGSSSATCIISGNT

-continued

```
VIWDNETPICDRIPCGLPPTITNGDFISTNRENFHYGSVVTYRCNPGSGGRKVFELVGE

PSIYCTSNDDQVGIWSGPAPQCIGGGGGGGRPFVEMYSEIPEIIHMTEGRELVIPCRVT

SPNITVTLKKFPLDTLIPDGKRIIWDSRKGFIISNATYKEIGLLTCEATVNGHLYKTNYL

THRQTNTIIDVVLSPSHGIELSVGEKLVLNCTARTELNVGIDFNWEYPSSKHQHKKLV

NRDLKTQSGSEMKKFLSTLTIDGVTRSDQGLYTCAASSGLMTKKNSTFVRVHEK.
```

In yet other embodiments, the fusion polypeptide comprises the amino acid sequence of:

```
                                                (SEQ ID NO: 40)
DTGRPFVEMYSEIPEIIHMTEGRELVIPCRVTSPNITVTLKKFPLDTLIPDGKRIIWDSR

KGFIISNATYKEIGLLTCEATVNGHLYKTNYLTHRQTNTIIDVVLSPSHGIELSVGEKL

VLNCTARTELNVGIDFNWEYPSSKHQHKKLVNRDLKTQSGSEMKKFLSTLTIDGVTR

SDQGLYTCAASSGLMTKKNSTFVRVHEKDKTHTCPPCPAPELLGGPSVFLFPPKPKD

TLMISRTPEVTCVVVDVSHEDPEVKFNWYVDGVEVHNAKTKPREEQYNSTYRVVSV

LTVLHQDWLNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLTVDKSRWQQ

GNVFSCSVMHEALHNHYTQKSLSLSPGKGGGGGGQCNAPEWLPFARPTNLTDEFEF

PIGTYLKYECRPGYYGRPFSIICLKNSVWTGAKDRCRRKSCRNPPDPVNGMVHVIKDI

QFGSQIKYSCTKGYRLIGSSSATCIISGNTVIWDNETPICDRIPCGLPPTITNGDFISTNR

ENFHYGSVVTYRCNPGSGGRKVFELVGEPSIYCTSNDDQVGIWSGPAPQCI.
```

Fusion proteins comprising at least two or more CIDs, two or more VIDs, and/or two or more half-life prolonging domains are also contemplated. For example, a fusion protein may comprise two CIDs, a VID, and an Fc region from N-terminal to C-terminal in an order of VID, Fc, CID, CID or any other combination thereof. In one embodiment, the fusion protein may comprise a CID, two VIDs, and an Fc region from N-terminal to C-terminal in an order of VID, VID, Fc, CID or any other combination thereof. In another embodiment, the fusion protein may comprise a CID, a VID, and two Fc regions from N-terminal to C-terminal in an order of VID, Fc, CID, Fc or any other combination thereof. In yet another embodiment, the fusion protein may comprise at least two CIDs, at least two VIDs, and at least two Fc regions from N-terminal to C-terminal in an order of VID, Fc, VID, Fc, CID, CID or any other combination thereof. Any combination of at least one VID, at least one CID, and at least one half-life-prolonging domain is provided herein as if each combination had been expressly stated herein.

The fusion proteins described in the present invention can comprise chemically modified forms of the CIDs. For example, the CIDs could be PEGylated or conjugated with polymers to increase half-life in vivo; or the CIDs could be chemically cross-linked to antibodies, fragment of antibodies, Fc regions, HSA, or other human proteins to increase half-life in vivo; or the CIDs could be formulated in any long-term sustained releasing format to prolong anti-complement activities in vivo.

The fusion proteins described in the present invention can comprise chemically modified forms of the VIDs. For example, the VIDs could be PEGylated or conjugated with polymers to increase half-life in vivo; or the VIDs could be chemically cross-linked to antibodies, fragment of antibodies, Fc regions, HSA, or other human proteins to increase half-life in vivo; or the VIDs could be formulated in any long-term sustained releasing format to prolong anti-complement activities in vivo.

The fusion proteins described in the present invention can comprise chemically modified forms of the CIDs and VIDs. For example, the CIDs and VIDs could be PEGylated or conjugated with polymers to increase half-life in vivo; or the CIDs and VIDs could be chemically cross-linked to antibodies, fragment of antibodies, Fc regions, HSA, or other human proteins to increase half-life in vivo; or the CIDs and VIDs could be formulated in any long-term sustained releasing format to prolong anti-complement activities in vivo.

In some embodiments, amino acid sequence variants of the fusion proteins provided herein are contemplated. For example, it may be desirable to improve the binding affinity and/or other biological properties of the CID, VID, and/or the half-life prolonging domain. Amino acid sequence variants of the fusion polypeptide may be prepared by introducing appropriate modifications into the nucleotide sequence encoding the CID, VID and/or half-life prolonging domain, or by peptide synthesis. Such modifications include, for example, deletions from, and/or insertions into and/or substitutions of residues within the amino acid sequences of the CID, VID and/or half-life prolonging domain. Any combination of deletion, insertion, and substitution can be made to arrive at the final construct, provided that the final construct possesses the desired characteristics (e.g., binding to a complement component, binding to a VEGF, inhibiting activation of complement pathway, inhibiting activation of VEGF pathway, and/or prolonged half-life). In some embodiments, the fusion polypeptide comprises at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence of a fusion polypeptide comprising any CID, VID, and Fc as disclosed herein from N-terminal to C-terminal in an order selected from the group consisting of (1) VID, Fc, CID; (2) CID, Fc, VID; (3) CID, VID, Fc; (4) VID, CID, Fc; (5) Fc, VID, CID; and (6) Fc, CID, VID. In some embodiments, the fusion polypeptide variant comprises at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence selected from the group consisting of SEQ ID NOs:12, 33-37, and 40.

Amino acid residue substitutions disclosed herein also include conservative substitutions. Conservative substitutions are shown in the Table 2 below under the heading of "preferred substitutions". If such substitutions result in a change in biological activity, then more substantial changes, denominated "exemplary substitutions" in Table 2, or as further described below in reference to amino acid classes, may be introduced and the products screened. Amino acid substitutions as shown in Table 2 or as described below in reference to the amino acid classes may be introduced into any of the fusion polypeptides or fragments thereof (e.g., CID, VID, half-life-prolonging domain, etc.) provided herein.

TABLE 2

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the proteins or polypeptides are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to common side-chain properties:
  (1) hydrophobic: Norleucine, Met, Ala, Val, Leu, Ile;
  (2) neutral hydrophilic: Cys, Ser, Thr, Asn, Gln;
  (3) acidic: Asp, Glu;
  (4) basic: His, Lys, Arg;
  (5) residues that influence chain orientation: Gly, Pro;
  (6) aromatic: Trp, Tyr, Phe;
  (7) large hydrophobic: Norleucine, Met, Val, Leu, Ile.

Non-conservative substitutions entail exchanging a member of one of these classes for another class.

A useful method for identification of certain residues or regions of the fusion protein that are preferred locations for mutagenesis is called "alanine scanning mutagenesis" as described by Cunningham and Wells in Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the target binding partner. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed fusion polypeptide variants are screened for the desired activity.

Any cysteine residue not involved in maintaining the proper conformation of the fusion polypeptides or fragments thereof (e.g., CID, VID, half-life-prolonging domain, etc.) also may be substituted, generally with serine, to improve the oxidative stability of the molecule and prevent aberrant crosslinking. Conversely, cysteine bond(s) may be added to the fusion polypeptides or fragments thereof (e.g., CID, VID, half-life-prolonging domain, etc.) to improve its stability.

In further embodiments, peptides or polypeptides of the invention may comprise one or more non-naturally occurring or modified amino acids. A "non-naturally occurring amino acid residue" refers to a residue, other than those naturally occurring amino acid residues listed above, which is able to covalently bind adjacent amino acid residues(s) in a polypeptide chain. Non-natural amino acids include, but are not limited to homo-lysine, homo-arginine, homo-serine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2 aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, citrulline, pentylglycine, pipecolic acid and thioproline. Modified amino acids include natural and non-natural amino acids which are chemically blocked, reversibly or irreversibly, or modified on their N-terminal amino group or their side chain groups, as for example, N-methylated D and L amino acids, side chain functional groups that are chemically modified to another functional group. For example, modified amino acids include methionine sulfoxide; methionine sulfone; aspartic acid-(beta-methyl ester), a modified amino acid of aspartic acid; N-ethylglycine, a modified amino acid of glycine; or alanine carboxamide and a modified amino acid of alanine. Additional non-natural and modified amino acids, and methods of incorporating them into proteins and peptides, are known in the art (see, e.g., Sandberg et al., (1998) J. Med. Chem. 41: 2481-91; Xie and Schultz (2005) Curr. Opin. Chem. Biol. 9: 548-554; Hodgson and Sanderson (2004) Chem. Soc. Rev. 33: 422-430.

Amino acid sequence insertions include amino-("N") and/or carboxy-("C") terminal fusions ranging in length from one residue to polypeptides containing a hundred or more residues, as well as intrasequence insertions of single or multiple amino acid residues. Examples of terminal insertions include a fusion polypeptide with an N-terminal methionyl residue or the fusion polypeptide fused to a cytotoxic polypeptide. Other insertional variants of the fusion polypeptide molecule include the fusion to the N- or C-terminus of the fusion polypeptide to an enzyme or a polypeptide which increases the serum half-life of the fusion polypeptide (e.g., half-life proloning domain).

The present invention provides a signal peptide that can be a component of any fusion polypeptides provided herein. For example, a fusion polypeptide comprising a CID, a VID, and a half-life prolonging domain may further comprise a heterologous polypeptide, preferably a signal sequence or other polypeptide having a specific cleavage site at the N-terminus of the mature protein or polypeptide. The heterologous signal sequence selected preferably is one that is recognized and processed (i.e., cleaved by a signal peptidase) by eukaryotic host-cells. For prokaryotic host-cells that do not recognize and process native mammalian signal sequences, the eukaryotic (i.e., mammalian) signal sequence is replaced by a prokaryotic signal sequence selected, for example, from the group consisting of leader sequences from alkaline phosphatase, penicillinase, lpp, or heat-stable enterotoxin II genes. For yeast secretion the native signal sequence may be substituted by, e.g., the yeast invertase leader, factor leader (including *Saccharomyces* and *Kluyveromyces*-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex virus gD signal, are available. In some embodiments, a fusion polypeptide comprising a VID, a CID, and a half-life prolonging domain further comprises a signal peptide comprising the amino acid sequence selected from the group consisting of SEQ ID NOs:9, 10 and 43. A signal peptide can be completely cleaved from the fusion polypeptide as it is produced from host cells or it can be partially cleaved. A mixed population of fusion polypeptides can be produced from a host cell wherein fusion polypeptides comprise a completely cleaved signal sequence (e.g., no signal sequence), a partially cleaved signal sequence (e.g., portion of the signal sequence) and/or a non-cleaved signal sequence (e.g., complete signal sequence). For example, any fusion polypeptide disclosed herein further comprising at its N-terminus a signal peptide comprising an amino acid sequence selected from the group consisting of SEQ ID NOs:9, 10, and 43 can be partially cleaved at the N-terminus. In one embodiment, a fusion polypeptide further comprising a signal peptide at the N-terminus can be cleaved at the N-terminus by any one of 1, 2, 3, 4, 5, 6, 7, 8, 9, 10, 11, 12, 13, 14, 15, 16, 17, 18, 19, 20, 21, or 22 amino acid residues. In another embodiment, a fusion polypeptide further comprising a signal peptide at the N-terminus can be cleaved at the N-terminus to produce a fusion polypeptide comprising any one of 1, 2, 3, 4, or 5 amino acid residues from the signal peptide. In some embodiments, a fusion polypeptide comprising the amino acid sequence selected from the group consisting of SEQ ID NOs:12, 33-37, and 40, further comprises a signal peptide comprising the amino acid sequence of SEQ ID NO:9. In other embodiments, a fusion polypeptide comprising the amino acid sequence selected from the group consisting of SEQ ID NOs:12, 33-37 and 40, further comprises a signal peptide comprising the amino acid sequence of SEQ ID NO:10 or 43.

The present invention provides a dimeric fusion protein comprising two fusion proteins, wherein each fusion protein comprises any fusion protein disclosed herein. In one embodiment, the dimeric fusion protein comprises two identical fusion proteins. In another embodiment, the dimeric fusion protein comprises two different fusion proteins. In another embodiment, the dimeric fusion protein comprises at least one fusion protein comprising the amino acid sequence selected from the group consisting of SEQ ID NOs:12, 33-37 and 40, or an amino acid sequence having at least 90% identity to the amino acid sequence selected from the group consisting of SEQ ID NOs:12, 33-37 and 40. In another embodiment, a fusion protein comprising the amino acid sequence selected from the group consisting of SEQ ID NOs:12, 33-37, and 40 can have 1, 2, 3, 4, or 5 amino acid residues removed from the N-terminus or C-terminus. In one embodiment, the fusion protein is recovered from a host cell comprising a nucleic acid encoding said fusion protein as a protein fusion dimer.

IV. Nucleic Acids, Vectors, and Host Cells

Nucleic Acids

Provided herein are isolated nucleic acids encoding any of the CIDs described herein. In some embodiments, the CID comprises an amino acid sequence encoded by the nucleic acid sequence selected from the group consisting of SEQ ID NOs:17-22 and 29-32. This disclosure further provides an isolated nucleic acid molecule, wherein the nucleic acid molecule encodes a CID comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence selected from the group consisting of SEQ ID NOs:1-6 and 13-16. Also provided herein are isolated nucleic acids encoding any of the VIDs described herein. In some embodiments, the VID comprises an amino acid sequence encoded by the nucleic acid sequence of SEQ ID NO:27. Further provided herein is an isolated nucleic acid molecule, wherein the nucleic acid molecule encodes a VID comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence selected from group consisting of SEQ ID NOs:11 and 38. Provided herein are also isolated nucleic acids encoding any of the half-life prolonging domains described herein. In some embodiments the half-life prolonging domain is an Fc region. In some embodiments, the Fc region comprises an amino acid sequence encoded by the nucleic acid sequence of SEQ ID NO:23. Further provided herein is an isolated nucleic acid molecule, wherein the nucleic acid molecule encodes a half-life prolonging domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence selected from the group consisting of SEQ ID NOs:7, 39, 41, and 42. Provided herein are isolated nucleic acids encoding any of the fusion polypeptides described herein. In some embodiments, the fusion polypeptide comprises an amino acid sequence encoded by the nucleic acid sequence of SEQ ID NO:28. Further provided herein is an isolated nucleic acid molecule, wherein the nucleic acid molecule encodes a fusion polypeptide comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence selected from the group consisting of SEQ ID NOs:12, 33-37 and 40.

Polynucleotide sequences encoding any of the polypeptides described herein (e.g., CIDs, VIDs, half-life prolonging domains, linkers, fusion polypeptides, etc.) can be obtained using standard synthetic and/or recombinant techniques. Desired polynucleotide sequences may be isolated and sequenced from appropriate source cells. Source cells for antibodies, peptides, and/or polypeptides would include antibody, peptide, and/or polypeptide producing cells such as hybridoma cells. Alternatively, polynucleotides can be synthesized using nucleotide synthesizer or PCR techniques.

Vectors

Once obtained, sequences encoding the peptide, and/or polypeptide are inserted into a recombinant vector capable of replicating and expressing heterologous polynucleotides in a host cell. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication (in particular when the vector is inserted into a prokaryotic cell), a selection marker gene, a promoter, a ribosome binding site (RBS), a signal sequence, the heterologous nucleic acid insert and a transcription termination sequence. In some embodiments, the vector is an expression vector. In some embodiments, the vector comprises a nucleic acid encoding a CID amino acid sequence. In some aspects, the vector comprises a nucleic acid sequence encoding a CID comprising an amino acid sequence selected from the group consisting of SEQ ID NOs:1-6 and 13-16. In some embodiments, the vector comprises a nucleic acid encoding a VID amino acid sequence. In some aspects, the vector comprises a nucleic acid sequence encoding a VID comprising an amino acid sequence selected from the group consisting of SEQ ID NOs:11 and 38. In some embodiments, the vector comprises a nucleic acid encoding a half-life prolonging domain amino acid sequence. In some aspects, the half-life prolonging domain is an Fc region. Suitable Fc region sequences are well known in the art. For example, a number of expression vectors encoding one or more Fc regions are available from the American Type Culture Collection (Rockville, Md.). In some aspects, the vector comprises a nucleic acid sequence encoding a Fc region comprising an amino acid sequence selected from the group consisting of SEQ ID NOs:7, 39, 41, and 42. In some embodiments, the vector comprises a nucleic acid encoding a fusion polypeptide amino acid sequence. In some aspects, the vector comprises a nucleic acid sequence encoding a fusion polypeptide comprising an amino acid sequence selected from the group consisting of SEQ ID NOs:12, 33-37, and 40.

In some embodiments, the vector comprising a nucleic acid encoding a fusion polypeptide amino acid sequence further comprises a nucleic acid encoding a signal peptide. The nucleic acid encoding the signal peptide is ligated in reading from to the nucleic acid encoding the fusion polypeptide. In some aspects, the vector comprising a nucleic acid encoding a fusion polypeptide further comprises a nucleic acid encoding a signal peptide comprising an amino acid sequence selected from the group consisting of SEQ ID NOs:9, 10 and 43. In some aspects, the vector comprises a nucleic acid encoding a fusion polypeptide comprising the amino acid sequence selected from the group consisting of SEQ ID NOs:12, 33-37, and 40 and a nucleic acid encoding a signal sequence comprising the amino acid sequence of SEQ ID NO:9, SEQ ID NO:10, or SEQ ID NO:43. In some aspects, the vector comprises a nucleic acid encoding a fusion polypeptide comprising the amino acid sequence of SEQ ID NO:12 and a nucleic acid encoding a signal sequence comprising the amino acid sequence of SEQ ID NO:9, SEQ ID NO:10, or SEQ ID NO:43. In other aspects, the vector comprises a nucleic acid encoding a fusion polypeptide comprising the amino acid sequence of SEQ ID NO:40 and a nucleic acid encoding a signal sequence comprising the amino acid sequence of SEQ ID NO:9, SEQ ID NO:10, or SEQ ID NO:43. Vectors well known in the art, as well as vectors disclosed herein (e.g., pCI-neo), can be used for replicating and expressing polynucleotides encoding any of the fusion polypeptides or fragments thereof (e.g., CID, VID, half-life-prolonging domain, etc.) disclosed herein in a host cell.

(1) Signal Sequence Component

In some embodiments, each cistron within a recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In some embodiments, the signal sequence is encoded by a nucleic acid selected from the group consisting of SEQ ID NOs:25 and 26.

(2) Origin of Replication

Both expression and cloning vectors contain a nucleic acid sequence that enables the vector to replicate in one or more selected host-cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2µ plasmid origin is suitable for yeast, and various viral origins (SV40, polyoma, adenovirus, vesicular stomatitis virus ("VSV") or bovine papilloma virus ("BPV") are useful for cloning vectors in mammalian cells. Generally, the origin of replication component is not needed for mammalian expression vectors (the SV40 origin may typically be used only because it contains the early promoter).

(3) Selection Gene Component

Expression and cloning vectors may also contain a selection gene, known as a selectable marker capable of providing phenotypic selection in transformed cells. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. One example of a selection scheme utilizes a drug to arrest growth of a host-cell. Those cells that are successfully transformed with a heterologous gene produce a protein conferring drug resistance and thus survive the selection regimen. Examples of such dominant selection strategies use the drugs neomycin, mycophenolic acid and hygromycin. Another example of suitable selectable markers for mammalian cells are those that enable the identification of cells competent to take up the fusion polypeptide- or fusion polypeptide fragment-encoding nucleic acids, such as dihydrofolate reductase ("DHFR"), glutamine synthetase (GS), thymidine kinase, metallothionein-I and -II, preferably primate metallothionein genes, adenosine deaminase, ornithine decarboxylase, and the like. For example, cells transformed with the DHFR selection gene are first identified by culturing all of the transformants in a culture medium that contains methotrexate (Mtx), a competitive antagonist of DHFR. An exemplary host-cell strain for use with wild-type DHFR is the Chinese hamster ovary ("CHO") cell line lacking DHFR activity (e.g., ATCC CRL-9096). Alternatively, cells transformed with the GS (glutamine synthetase) gene are identified by culturing the transformants in a culture medium containing L-methionine sulfoximine (Msx), an inhibitor of GS. Under these conditions, the GS gene is amplified along with any other co-transformed nucleic acid. The GS selection/amplification system may be used in combination with the DHFR selection/amplification system described above.

For another example, E. coli is typically transformed using pBR322, a plasmid derived from an E. coli species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins.

A suitable selection gene for use in yeast is the trp1 gene present in the yeast plasmid YRp7 (Stinchcomb et al., Nature, 282:39 (1979)). The trp1 gene provides a selection marker for a mutant strain of yeast lacking the ability to grow medium containing tryptophan (e.g., ATCC No. 44076 or PEP4-1). Jones, Genetics, 85:12 (1977). The presence of the trp1 lesion in the yeast host-cell genome then provides an effective environment for detecting transformation by growth in the absence of tryptophan. Similarly, Leu2-deficient yeast strains (e.g., ATCC 20,622 or 38,626) can be complemented by known plasmids bearing the Leu2 gene. In addition, vectors derived from the 1.6 µm circular plasmid pKD1 can be used for transformation of Kluyveromyces yeasts. Alternatively, an expression system for large-scale production of recombinant calf chymosin was reported for K. lactis. Van den Berg, Bio/Technology, 8:135 (1990). Stable multi-copy expression vectors for secretion of mature recombinant human serum albumin by industrial strains of Kluyveromyces have also been disclosed. Fleer et al., Bio/Technology, 9:968-975 (1991).

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as E. coli LE392.

(4) Promoter Component

Expression and cloning vectors usually contain a promoter that is recognized by the host organism and is operably linked to the nucleic acid encoding the fusion polypeptides or fragments thereof (e.g., CID, VID, half-life-prolonging domain, etc.). Promoters suitable for use with prokaryotic hosts include the phoA promoter, lactamase and lactose promoter systems, alkaline phosphatase promoter, a tryptophan promoter system, and hybrid promoters such as the tac promoter. However, other promoters that are functional in bacteria (such as other known bacterial or phage promoters) are suitable as well.

Either constitutive or inducible promoters can be used in the present invention, in accordance with the needs of a particular situation, which can be ascertained by one skilled in the art. A large number of promoters recognized by a variety of potential host cells are well known. The selected promoter can be operably linked to cistron DNA encoding a polypeptide described herein by removing the promoter from the source DNA via restriction enzyme digestion and inserting the isolated promoter sequence into the vector of choice. Both the native promoter sequence and many heterologous promoters may be used to direct amplification and/or expression of the target genes. However, heterologous promoters are preferred, as they generally permit greater transcription and higher yields of expressed target gene as compared to the native target polypeptide promoter.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the polyA tail to the 3' end of the coding sequence. All of these sequences may be inserted into eukaryotic expression vectors.

Examples of suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phosphoglucose isomerase, and glucokinase.

Inducible promoters in yeast have the additional advantage of permitting transcription controlled by growth conditions. Exemplary inducible promoters include the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Transcription of nucleic acids encoding fusion polypeptides or fragments thereof (e.g., CID, VID, half-life-prolonging domain, etc.) from vectors in mammalian host-cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), by heterologous mammalian promoters, e.g., the actin promoter or an immunoglobulin promoter, and by heat-shock gene promoters, provided such promoters are compatible with the desired host-cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature* 297:598-601 (1982), regarding methods for expression of human interferon cDNA in mouse cells under the control of a thymidine kinase promoter from herpes simplex virus. Alternatively, the Rous Sarcoma Virus long terminal repeat can be used as the promoter.

(5) Enhancer Element Component

Transcription of a DNA encoding the fusion polypeptides or fragments thereof (e.g., CID, VID, half-life-prolonging domain, etc.) by higher eukaryotes is often increased by inserting an enhancer sequence into the vector. Many enhancer sequences are now known from mammalian genes (globin, elastase, albumin, α-fetoprotein, and insulin). Typically, however, one of ordinary skill in the art will use an enhancer from a eukaryotic virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297:17-18 (1982) on enhancing elements for activation of eukaryotic promoters. The enhancer may be spliced into the vector at a position 5' or 3' to the fusion protein- or fusion protein-fragment encoding sequences, but is preferably located at a site 5' of the promoter.

(6) Transcription Termination Component

Expression vectors used in eukaryotic host-cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding antibodies or fragments thereof. One useful transcription termination component is the bovine growth hormone polyadenylation region. See WO94/11026 and the expression vector disclosed therein.

Host Cells

Suitable host-cells for cloning or expressing the DNA encoding fusion polypeptides or fragments thereof (e.g., CID, VID, half-life-prolonging domain, etc.) in the vectors described herein include the prokaryotic, yeast, or higher eukaryotic cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are also suitable. These examples are illustrative rather than limiting.

Fusion polypeptides or fragments thereof (e.g., CID, VID, half-life-prolonging domain, etc.) can be produced in bacteria, in particular when glycosylation is not needed, such as when the fusion polypeptides or fragments thereof (e.g., CID, VID, half-life-prolonging domain, etc.) is conjugated to a cytotoxic agent (e.g., a toxin). Production in *E. coli* is faster and more cost efficient. For expression of fusion polypeptides or fragments thereof (e.g., CID, VID, half-life-prolonging domain, etc.) in bacteria, see, e.g., U.S. Pat. No. 5,648,237 (Carter et. al.), U.S. Pat. No. 5,789,199 (Joly et al.), and U.S. Pat. No. 5,840,523 (Simmons et al.) which describes translation initiation region (TIR) and signal sequences for optimizing expression and secretion. After expression, fusion polypeptides or fragments thereof (e.g., CID, VID, half-life-prolonging domain, etc.) are isolated from the *E. coli* cell paste in a soluble fraction and can be purified through, e.g., a protein A or G column depending on the binding portion of the fusion polypeptide, such as the Fc region isotype. Final purification can be carried out by the same process used to purify fusion polypeptides or fragments thereof (e.g., CID, VID, half-life-prolonging domain, etc.) expressed, e.g., in CHO cells.

In addition to prokaryotes, eukaryotic microbes such as filamentous fungi or yeast are also suitable cloning or expression hosts for fusion polypeptides or fragments thereof (e.g., CID, VID, half-life-prolonging domain, etc.) encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* spp., such as *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*. For a review discussing the use of yeasts and filamentous fungi for the production of therapeutic proteins, see, e.g., Gerngross, *Nat. Biotech.* 22: 1409-1414 (2004).

Certain fungi and yeast strains may be selected in which glycosylation pathways have been "humanized," resulting in the production of a fusion polypeptides or fragments thereof (e.g., CID, VID, half-life-prolonging domain, etc.) with a partially or fully human glycosylation pattern. See, e.g., Li et al., *Nat. Biotech.* 24:210-215 (2006) (describing humanization of the glycosylation pathway in *Pichia pastoris*); and Gerngross et al., supra.

Suitable host-cells for the expression of glycosylated fusion polypeptides or fragments thereof (e.g., CID, VID, half-life-prolonging domain, etc.) are derived from multicellular organisms. Examples of invertebrate cells include plant and insect-cells. Numerous baculoviral strains and variants and corresponding permissive insect host-cells from hosts such as *Spodoptera frugiperda* (caterpillar), *Aedes aegypti* (mosquito), *Aedes albopictus* (mosquito), *Drosophila melanogaster* (fruitfly), and *Bombyx mori* (moth) have been identified. A variety of viral strains for transfection are publicly available, e.g., the L-1 variant of *Autographa californica* NPV and the Bm-5 strain of *Bombyx mori* NPV. Such viruses may be used as the virus herein according to the present invention, particularly for transfection of *Spodoptera frugiperda* cells.

Plant-cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host-cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Nat'l Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. *Acad. Sci.* 383:44-68 (1982)); MRC 5 cells; FS4 cells; and a human hepatoma line (Hep G2). Other useful mammalian host cell lines include Chinese hamster ovary (CHO) cells, including DHFR$^-$ CHO cells (Urlaub et al., Proc. Natl. Acad. Sci. USA 77:4216 (1980)); and myeloma cell lines such as NS0 and Sp2/0. For a review of certain mammalian host cell lines suitable for polypeptide production, see, e.g., Yazaki and Wu, Methods in Molecular Biology, Vol. 248 (B. K. C. Lo, ed., Humana Press, Totowa, N.J., 2003), pp. 255-268.

Examples of mammalian cells capable of expressing any of the proteins disclosed herein can be selected from the group consisting of a hamster cell, a mouse cell, a rat cell, a rabbit cell, a cat cell, a dog cell, a bovine cell, a goat cell, a porcine cell, an equine cell, a sheep cell, a monkey cell, a chimpanzee cell, and a human cell. In another embodiment, the animal cell is a neural cell (such as, but not limited to, a peripheral nervous system cell or a central nervous system cell), a muscle cell (such as a cardiac, skeletal, or smooth muscle cell), a gamete (such as a sperm cell or an oocyte), a cancer cell, an immune cell (such as, but not limited to, a macrophage, a T-cell, or a B-cell), a stem cell (such as, but not limited to, an embryonic stem cell or an adult stem cell), or an endocrine cell (such as, but not limited to, a thyroid cell, a hypothalamic cell, a pituitary cell, an adrenal cell, a testicular cell, an ovarian cell, a pancreatic cell (such as a β cell), a stomach cell, or an intestinal cell). In some embodiments, the cell is a human cell in cell culture. In some embodiments, the cell is a non-human cell in cell culture. In some embodiments, the cell is a cancer cell.

Host cells are transformed or transfected with the above-described expression or cloning vectors for fusion polypeptides or fragments thereof (e.g., CID, VID, half-life-prolonging domain, etc.) production and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, CaPO$_4$ precipitation and electroporation. Successful transfection is generally recognized when any indication of the operation of this vector occurs within the host cell.

Transformation means introducing DNA into the prokaryotic host so that the DNA is replicable, either as an extra-chromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Another technique that can be used is electroporation.

V. Methods of Producing Fusion Polypeptides and Fragments Thereof

Provided herein are methods for producing fusion polypeptides or fragments thereof (e.g., CID, VID, half-life-prolonging domain, etc.) of the invention as disclosed herein. In some embodiments, a method for producing any fusion polypeptide as disclosed herein comprising culturing a host cell comprising a nucleic acid encoding any of the fusion polypeptides disclosed herein under a condition that produces the fusion polypeptide, and recovering the fusion polypeptide produced by the host cell. In some aspects, a method for producing a fusion polypeptide comprising culturing the host cell comprising the nucleic acid encoding the fusion polypeptide comprising the amino acid sequence selected from the group consisting of SEQ ID NOs:12, 33-37, and 40 under a condition that produces the fusion polypeptide, and recovering the fusion polypeptide produced by the host cell.

(1) Culturing the Host Cells

Prokaryotic cells used to produce the fusion polypeptides or fragments thereof (e.g., CID, VID, half-life-prolonging domain, etc.) of the invention are grown in media known in the art and suitable for culture of the selected host cells. Examples of suitable media include luria broth (LB) plus necessary nutrient supplements. In preferred embodiments, the media also contains a selection agent, chosen based on the construction of the expression vector, to selectively permit growth of prokaryotic cells containing the expression vector. For example, ampicillin is added to media for growth of cells expressing ampicillin resistant gene. Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol. The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0. If an inducible promoter is used in the expression vector, protein expression is induced under conditions suitable for the activation of the promoter. For example, if a PhoA promoter is used for controlling transcription, the transformed host cells may be cultured in a phosphate-limiting medium for induction. A variety of other inducers may be used, according to the vector construct employed, as is known in the art.

The host cells used to produce the fusion polypeptides or fragments thereof (e.g., CID, VID, half-life-prolonging domain, etc.) described herein may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WIPO Publication Nos. WO 90/03430; WO 87/00195; or U.S. patent Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(2) Purification of Fusion Polypeptides and Fragments Thereof

When using recombinant techniques, the fusion polypeptides or fragments thereof (e.g., CID, VID, half-life-prolonging domain, etc.) described herein can be produced intracellularly, in the periplasmic space, or secreted directly into the medium. If the polypeptides are produced intracellularly, as a first step, protein recovery typically involves disrupting the microorganism, generally by such means as osmotic shock, sonication or lysis. Once cells are disrupted, particulate debris from either host cells or lysed fragments is removed, for example, by centrifugation or ultrafiltration. Carter et al., *Bio/Technology* 10:163-167 (1992) describe a procedure for isolating polypeptides which are secreted to the periplasmic space of *E. coli*. Briefly, cell paste is thawed in the presence of sodium acetate (pH 3.5), EDTA, and phenylmethylsulfonylfluoride (PMSF) over about 30 minutes. Cell debris can be removed by centrifugation. Where the polypeptides are secreted into the medium, supernatants from such expression systems are generally first filtered and concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The fusion polypeptides or fragments thereof (e.g., CID, VID, half-life-prolonging domain, etc.) compositions prepared from such cells can be purified using, for example, hydroxylapatite chromatography, gel electrophoresis, dialysis, and affinity chromatography, with affinity chromatography being the preferred purification technique. In some embodiments, protein A or protein G is used as an affinity ligand for use in affinity chromatography. The suitability of protein A as an affinity ligand depends on the species and isotype of any immunoglobulin Fc region that is present in the fusion polypeptides or fragments thereof (Lindmark et al., *J. Immunol. Meth.* 62:1-13 (1983). In a preferred embodiment, protein A is used as an affinity ligand for isolating and purifying fusion polypeptides or fragments thereof (e.g., CID, VID, half-life-prolonging domain, etc.) as described herein. In some embodiments, protein G is used as an affinity ligand for isolating and purifying fusion polypeptides or fragments thereof (e.g., CID, VID, half-life-prolonging domain, etc.) as described herein. The matrix to which the affinity ligand is attached is most often agarose, but other matrices are available. Mechanically stable matrices such as controlled pore glass or poly(styrene-divinyl) benzene allow for faster flow rates and shorter processing times than can be achieved with agarose. Other techniques for protein purification, such as fractionation on an ion-exchange column, ethanol precipitation, Reverse Phase HPLC, chromatography on silica, heparin, SEPHAROSE™, or anion or cation exchange resins (such as a polyaspartic acid column), as well as chromatofocusing, SDS-PAGE, and ammonium sulfate precipitation are also available depending on the fusion polypeptides or fragments thereof (e.g., CID, VID, half-life-prolonging domain, etc.) to be recovered. In some embodiments, the recovered fusion protein is substantially pure. In a further embodiment, the recovered fusion protein is at least any of 90%, 91%, 92.%, 93%, 94%, 95%, 96%, 97%, 98%, or 99% pure.

Following any preliminary purification step or steps, the mixture comprising the fusion polypeptide or fragments thereof (e.g., CID, VID, half-life-prolonging domain, etc.) of interest and contaminants may be subjected to low pH hydrophobic interaction chromatography using an elution buffer at a pH between about 2.5-4.5, preferably performed at low salt concentrations (e.g., from about 0-0.25 M salt).

In general, various methodologies for preparing fusion polypeptides or fragments thereof (e.g., CID, VID, half-life-prolonging domain, etc.) for use in research, testing, and clinical applications are well-established in the art, consistent with the above-described methodologies and/or as deemed appropriate by one skilled in the art for a particular fusion polypeptides or fragments thereof (e.g., CID, VID, half-life-prolonging domain, etc.) of interest.

(3) Biological Activities of Fusion Polypeptides and Fragments Thereof

Polypeptides may be purified and identified using commonly known methods such as fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; hydrophobic affinity resins, ligand affinity using a suitable binding partner immobilized on a matrix, ELISA, BIACore, Western blot assay, amino acid and nucleic acid sequencing, and biological activity.

The fusion proteins disclosed herein may be characterized or assessed for biological activities including, but not limited to, affinity to a target binding partner (e.g., VEGF or complement protein), competitive binding (e.g., blocking of target binding partner to complement regulatory protein or VEGFR), inhibitory activity (e.g., inhibition of complement activation or VEGF activation), half-life or the fusion protein, inhibition of cell proliferation, inhibition of tumor growth, and inhibition of angiogenesis (e.g., choroidal neovascularization). In some embodiments, the fusion proteins disclosed herein can be assessed for biological activity in vivo and in vitro. In any of the assays described herein, the assay is performed at a temperature of 4° C., 20-28° C. (e.g., 25° C.), or 37° C.

The fusion proteins disclosed herein can be assessed for affinity to a binding partner such as a complement protein (e.g., C3b, C4b, iC3b, C3dg, C1q, or MBP). Many methods for assessing binding affinity are known in the art and can be used to identify the binding affinities of fusion proteins to a binding partner. Binding affinities can be expressed as dissociation constant (Kd) values or half maximal effective concentration (EC50) values. Techniques for determining binding affinities (e.g., Kd values) are well known in the art such as Enzyme-Linked Immunosorbent Assay (ELISA) and BIAcore. See Harlow and Lane, *Antibodies: A Laboratory Manual*, CSH Publications, NY (1988); Ausubel et al., *Current Protocols in Molecular Biology*, John Wiley & Sons, New York, (2009); Altschuh et al., *Biochem.*, 31:6298 (1992); and the BIAcore method disclosed by Pharmacia Biosensor, all of which are incorporated herein by reference. For example, binding affinities of the fusion proteins to a binding partner can be determined using ELISA. In some embodiments, binding of fusion proteins to C3b or C4b is assayed using ELISA. In this exemplary assay, the wells of a 96-well ELISA plate are coated with 100 ng/well of C3b or C4b. About 0-1 µM of purified fusion protein is added to each well and incubated for 1 hour before washing to remove unbound C3b or C4b. A 1:5000 dilution of an anti-Fc HRP conjugate (e.g., Sigma Catalog No. A0170-1ML) is subsequently added to each well and incubated 1 hour. After incubation, the wells are washed before addition of a stop reagent for TMB Substrate (e.g., Sigma Catalog No. S5814-100ML). Absorption of the sample is measured at 450 nm and analyzed by sigmoidal curve fitting using computational software (e.g., Prism4) in order to obtain a Kd value and/or EC50 value for binding of the fusion protein to C3b or C4b. In a further example, binding of fusion proteins to a VEGF (e.g., VEGF-A VEGF-B, VEGF-C, VEGF-D or PlGF) is assayed using ELISA. In an exemplary assay, a 96-well ELISA plate is coated with 100 ng VEGF-A (e.g., R&D Systems) and about 0-10 nM of purified fusion protein is added to each well before incubation for 1 hour. After washing, a 1:5000 dilution of anti-Fc HRP conjugate is added to each well for an incubation of 1 hour before washing and adding a stop reagent for TMB Substrate to each well. Absorption of the sample is measured at 450 nm and analyzed by sigmoidal curve fitting using computational software in order to obtain a Kd value and/or EC50 value for binding of the fusion protein to a VEGF-A. In a further exemplary assay, binding of fusion proteins to a soluble VEGF is assayed by ELISA using a Human VEGF Quantikine ELISA Kit (R&D Systems Catalog No. DVE00).

The fusion proteins disclosed herein can be assessed for inhibitory activity of a complement pathway (e.g., classical pathway, the alternative pathway, and/or the lectin pathway). Many methods for assessing inhibitory activity are known in the art and can be used to identify the inhibitory activity of a fusion protein. Binding affinities can be expressed as half maximal effective concentration (EC50) values. For example, inhibitory activity of the classical complement pathway or the lectin pathway by a fusion protein can be determined using a total hemolytic (CH50) assay. In this exemplary assay, a dilution of normal human serum that lyses 90% of $1 \times 10^7$ antibody sensitized sheep erythrocytes/ml after 1 hour incubation at 37° C. is first determined. The assay was carried out in buffer containing 0.15 mM $CaCl_2$ and 0.5 mM $MgCl_2$. Inhibition of the classical complement pathway is activated by mixing the dilution of normal human serum that can lyse 90% of antibody sensitized sheep erythrocytes with 0-500 nM of a fusion protein for 1 hour at 37° C. Hemolysis of antibody sensitized sheep erythrocytes is then assayed after 1 hour incubation by measuring absorption at 541 nm before analysis by sigmoidal curve fitting using computational software (e.g., Prism4) to obtain an EC50 value for inhibitory activity of the classical complement pathway or the lectin pathway by the fusion protein. In a further exemplary assay, inhibitory activity of the alternative complement by a fusion protein is determined by inclusion of ethylene glycol tetraacetic acid (EGTA) for chelation of calcium ions in the buffer used in the CH50 assay. In some embodiments, the inhibitory activity of a complement pathway by a fusion protein is the inhibition of the decay-accelerating activity (DAA) for the alternative C3-convertase. In another embodiment, the inhibitory activity of a complement pathway by a fusion protein is the inhibition of the decay-accelerating activity (DAA) for the alternative C3-convertase. Inhibition of DAA by a fusion protein can be determined by methods known in the art as well as any of the methods disclosed herein (e.g., Example 7). For an exemplary CH50 assay see Costabile, M., (2010). *J. Vis. Exp.* 29(37):1923 which is incorporated herein by reference in its entirety.

In any of the embodiments herein, a fusion protein has an EC50 of ≤1 µM, ≤100 nM, ≤10 nM, ≤1 nM, ≤0.1 nM, ≤0.01 nM, or ≤0.001 nM (e.g., $10^{-8}$M or less, e.g., from $10^{-8}$M to $10^{-13}$M, e.g., from $10^{-9}$M to $10^{-13}$ M) for inhibition of an activity (e.g., inhibition of complement activity and/or VEGF activity). In any of the embodiments herein, a fusion protein has a Kd for a binding partner (e.g., complement protein and/or VEGF) of less than about any of about 1.0 mM, 500 µM, 100 µM, 50 µM, 25 µM, 10 µM, 5 µM, 1 µM, 900 nM, 800 nM, 700 nM, 600 nM, 500 nM, 400 nM, 350 nM, 300 nM, 250 nM, 200 nM, 150 nM, 100 nM, 95 nM, 90 nM, 85 nM, 80 nM, 75 nM, 70 nM, 65 nM, 60 nM, 55 nM, 50 nM, 45 nM, 40 nM, 35 nM, 30 nM, 25 nM, 20 nM, 15 nM, 10 nM, 5 nM, 1 nM, 900 pM, 800 pM, 700 pM, 600 pM, 500 pM, 400 pM, 300 pM, 200 pM, 100 pM, 50 pM, 25 pM, 12.5 pM, 6.25 pM, 5 pM, 4 pM, or 3 pM, inclusive, including any values in between these numbers. In some embodiments, the fusion polypeptides variants described herein bind to a binding partner with a higher affinity compared to the binding of a wild-type fusion polypeptide described herein. In some aspects, the fusion polypeptide variant binds to a binding partner with at least any of 10, 20, 30, 40, 50, 60, 70, 80, 90, 100, 200, 300, 400, 500, 600, 700, 800, 900, 1000, 1500, 2000, 2500, 3000, 3500, 4000, 4500, 5000, 6000, 7000, 8000, 9000, or 10,000, inclusive, including any value in between these numbers, higher fold affinity compared to the binding of the binding partner by a fusion polypeptide comprising the amino acid sequence selected from the group consisting of SEQ ID NOs:12, 33-37, and 40.

In some embodiments, the fusion proteins disclosed herein can be assessed for anti-proliferative activities such as reduction of cell proliferation or tumor growth. Many methods for assessing anti-proliferative properties for a fusion protein are known in the art. In one exemplary assay, human umbilical vein endothelial cells (HUVECs) can be used to demonstrate inhibition of VEGF-dependent cell proliferation. In this assay, HUVECs are maintained in Endothelial Cell Growth Medium (e.g., Lonza, Inc.) with 2% FBS. About 50 µl of 1 nM of VEGF-A is added to the wells of a 96-well flat bottom microtiter plate coated with collagen and various concentrations of the fusion protein. About 50 µl of HUVECs at $1 \times 10^5$ cells/ml in Medium-199 (e.g., Hyclone, Inc.) are added to each well and incubated for 72 hours at 37° C. with 5% $CO_2$. After incubation, cell proliferation is assayed by adding 10 µl of CCK-8 (e.g., Dojindo, Inc.) to each well and then measuring OD absorption at 450/650 nm to determine inhibition of cell proliferation by the fusion protein. In an exemplary in vivo assay, inhibition of tumor growth is assessed in xenograft mice bearing tumors derived for a certain cancer type (e.g., hepatocellular carcinoma, colorectal cancer, etc.). In this assay, various concentrations of the fusion protein is administered to the mice at a particular dosage regimen and tumor growth is measured at least twice over a period of time to determine inhibition of tumor growth by the fusion protein. In some embodiments, anti-angiogenic properties for a fusion protein are measured using techniques well known in the art. In one exemplary assay, an animal model of wet age-related macular degeneration is used to assay inhibition of neovascularization in the eye by the fusion protein. In this assay, laser photocoagulation is delivered to the retina of the animal (e.g., mouse, monkey, etc.) to obtain choroidal neovascularization (CNV) and the fusion protein is administered. CNV lesions in the eyes of the animals (e.g., mice, rat, and monkeys), using techniques known in the art and disclosed herein (e.g., Example 11 and 12), are measured to determine if they are reduced by administration of the fusion protein. See Liu, J., et al., (2011). *J. Biol. Chem.* 286(23): 20991-21001; Nork, T. M., (2011). *Arch. Ophthalmol.* 129 (8):1042-1052; and Lichtlen, P. (2010). Invest. Ophthalmol. Vis. Sci. 15(9):4738-4745, which are incorporated herein by reference in their entirety.

VI. Methods of Treatment Using Fusion Polypeptides and Fragments Thereof

The invention provides methods for treating or preventing an inflammatory disease, autoimmune disease, complement-related disease, ocular disease, and cancer. In some embodiments, the invention provides a method of treating a subject with an inflammatory disease, autoimmune disease, complement-related disease, ocular disease, and/or cancer, comprising administering to the subject an effective amount of any fusion protein described herein. In some embodiments, the method further comprises administering to the individual an effective amount of at least one additional therapeutic agent, e.g., as described below. In some embodiments, the invention provides a fusion protein for use in inhibiting binding of a complement protein to a complement regulating protein. In some embodiments, the invention provides a fusion protein for use in inhibiting binding of a complement protein to a complement regulating protein in a subject comprising administering to the subject an effective amount of the fusion protein to inhibit binding of a complement protein to a complement regulating protein. In some embodiments, the invention provides a fusion protein for use in inhibiting binding of a VEGF to a VEGFR. In some embodiments, the invention provides a fusion protein for use in inhibiting binding of a VEGF to a VEGFR in a subject comprising administering to the subject an effective amount of the fusion protein to inhibit binding of a VEGF to a VEGFR. In some embodiments, the invention provides a fusion protein for use in inhibiting complement activation and VEGF signaling pathway (e.g., inhibition of VEGF activity) in a subject comprising administering to the subject an effective amount of the fusion protein to inhibit complement activation and VEGF signaling pathway (e.g, inhibition of VEGF activity). A "subject" according to any of the above embodiments is preferably human.

An inflammatory disease that can be treated or prevented by the fusion proteins described herein include, but is not limited to, macular degeneration (e.g., age-related macular degeneration), acute myocardial infarction (AMI), atherosclerosis, glomernephritis, asthma, and multiple sclerosis. An autoimmune disease that can be treated or prevented by the fusion proteins described herein include, but is not limited to, Alzheimer's disease, autoimmune uveitis, systemic lupus erythematosus (SLE), lupus nephritis, ulcerative colitis, inflammatory bowel disease, Crohn's disease, adult respiratory distress syndrome (ARDS), multiple sclerosis, diabetes mellitus, Huntington's disease, Parkinson's disease, rheumatoid arthritis, juvenile rheumatoid arthritis, osteoarthritis, psoriatic arthritis, CNS inflammatory disorders, myasthenia gravis, glomerulonephritis, and autoimmune thrombocytopenia. A complement-related disease that can be treated or prevented by the fusion proteins described herein include, but is not limited to, aneurysm, atypical hemolytic uremic syndrome, thrombotic thrombocytopenic purpura, idiopathic thrombocytopenic purpura, AMD, spontaneous fetal loss, recurrent fetal loss, traumatic brain injury, psoriasis, autoimmune hemolytic anemia, hereditary angioedema, stroke, hemorrhagic shock, septic shock, complication from surgery such as coronary artery bypass graft (CABG) surgery, pulmonary complications such as chronic obstructive pulmonary disease (COPD), ischemia-reperfusion injury, organ transplant rejection, and multiple organ failure. In some embodiments, the cancer that can be treated or prevented by the fusion proteins described herein includes colorectal cancer, non-small cell lung cancer, lymphoma, leukemia, adenocarcinoma, glioblastoma, kidney cancer, gastric cancer, prostate cancer, retinoblastoma, ovarian cancer, endometrial cancer, and breast cancer. In a further embodiment, any of the cancers disclosed herein that can be treated or prevented by the fusion proteins described herein is metastatic. An ocular disease that can be treated or prevented by the fusion proteins described herein include, but is not limited to, wet age-related macular degeneration, dry age-related macular degeneration, diabetic retinopathy, diabetic retinal edema, diabetic macular edema, retrolental fibroplasias, retinal central occlusion, retinal vein occlusion, ischemic retinopathy, hypertensive retinopathy, uveitis (e.g., anterior, intermediate, posterior, or panuveitis), Behcet's disease, Biett's crystalline dystrophy, blepharitis, glaucoma (e.g., open-angle glaucoma), neovascular glaucoma, neovascularization of the cornea, choroidal neovascularization (CNV), subretinal neovascularization, corneal inflammation, and complications from corneal transplantation.

The fusion proteins and compositions described herein are particularly useful for treating macular degeneration such as AMD. AMD is the leading cause of blindness and visual impairment among the elderly (>50 years) in the United States and other developed countries (Bird, A. C., (2010). *J. Clin. Invest.*, 120(9): 3033-3041). AMD is broadly classified into two types, a wet form and a dry form, with the dry form constituting up to 80-90% of all AMD cases. Dry AMD (non-exudative) is a form of AMD in which cellular debris called drusen accumulates between the retina and the choroid. Dry AMD has three stages, early, intermediate, and advanced, and is characterized by the presence of macular drusen. In advanced dry AMD, central geographic atrophy occurs resulting loss of vision in the center of the eye. The wet (exudative or neovascular) form AMD is the more severe form in which abnormal blood vessels (choroidal neovascularization, CNV) grow up from the choroid through Bruch's membrane behind the macula, resulting in rapid vision loss. In recent years, increasing evidence has indicated that complement activation plays a major role in pathogenesis of AMD (Issa, P. C., et al, (2011), *Graefes. Arch. Clin. Exp. Ophthalmol.*, 249: 163-174). For example, high levels of complement proteins have been detected in drusen. Furthermore, genetic studies have confirmed association of AMD risk and polymorphism in genes of complement proteins including Factor H (CFH), CFHR1, CFHR3, C2, C3, Factor B, Factor I. In particular, the CFH Y402H allele correlates highly with AMD risk. Finally, increased levels of complement activation products have also been found in plasma of AMD patients. AMD can be detected in subjects with a visual acuity test, a dilated eye exam, an amsler grid, a fluorescein angiogram, or by genetic testing for AMD associated biomarkers. It is generally accepted that dry AMD can progress to wet AMD. The present invention provides methods of treating AMD (such as wet or dry forms of AMD) by administering an effective amount of a composition comprising a fusion protein as described herein. In some embodiments, the invention provides methods of treating or preventing one or more aspects or symptoms of AMD, including, but not limited to, formation of ocular drusen, inflammation in the eye or eye tissue, loss of photoreceptor cells, loss of vision (including for example visual acuity and visual field), neovascularization, subretinal hemorrhage, retinal detachment, blood vessel leakage and any other AMD related aspects.

In a further aspect, the invention provides for the use of a fusion protein in the manufacture or preparation of a medicament. In some embodiments, the medicament is for treatment of an inflammatory disease, autoimmune disease, complement-related disease, ocular disease, and cancer. In some embodiments, the invention provides a fusion protein for the manufacture of a medicament for use in inhibiting binding of a complement protein to a complement regulating protein. In some embodiments, the invention provides a fusion protein for the manufacture of a medicament for use in inhibiting binding of a VEGF to a VEGFR. In some embodiments, the invention provides a fusion protein for the manufacture of a medicament for use in inhibiting complement activation and VEGF signaling pathway (e.g., inhibition of VEGF activity) in a subject comprising administering to the subject an effective amount of the fusion protein to inhibit complement activation and VEGF signaling pathway (e.g., inhibition of VEGF activity). A "subject" according to any of the above embodiments is preferably human. In some embodiments, the medicament is used for treatment of an inflammatory disease including, but not limited to, macular degeneration (e.g., age-related macular degeneration), acute myocardial infarction (AMI), atherosclerosis, glomernephritis, asthma, and multiple sclerosis. In some embodiments, the medicament is used for treatment of an autoimmune disease including, but not limited to, Alzheimer's disease, autoimmune uveitis, systemic lupus erythematosus (SLE), lupus nephritis, ulcerative colitis, inflammatory bowel disease, Crohn's disease, adult respiratory distress syndrome (ARDS), multiple sclerosis, diabetes mellitus, Huntington's disease, Parkinson's disease, rheumatoid arthritis, juvenile rheumatoid arthritis, osteoarthritis, psoriatic arthritis, CNS inflammatory disorders, myasthenia gravis, glomerulonephritis, and autoimmune thrombocytopenia. In some embodiments, the medicament is used for treatment of a complement-related disease including, but not limited to, aneurysm, atypical hemolytic uremic syndrome, thrombotic thrombocytopenic purpura, idiopathic thrombocytopenic purpura, AMD, spontaneous fetal loss, recurrent fetal loss, traumatic brain injury, psoriasis, autoimmune hemolytic anemia, hereditary angioedema, stroke, hemorrhagic shock, septic shock, complication from surgery such as coronary artery bypass graft (CABG) surgery, pulmonary complications such as chronic obstructive pulmonary disease (COPD), ischemia-reperfusion injury, organ transplant rejection, and multiple organ failure. In some embodiments, the cancer that can be treated or prevented by the fusion proteins described herein includes colorectal cancer, metastatic colorectal cancer, non-small cell lung cancer, lymphoma, leukemia, adenocarcinoma, glioblastoma, kidney cancer, metastatic kidney cancer, gastric cancer, prostate cancer, retinoblastoma, ovarian cancer, endometrial cancer, and breast cancer. In other embodiments, the medicament is used for treatment of an ocular disease including, but not limited to, wet age-related macular degeneration, dry age-related macular degeneration, diabetic retinopathy, diabetic retinal edema, diabetic macular edema, retrolental fibroplasias, retinal central occlusion, retinal vein occlusion, ischemic retinopathy, hypertensive retinopathy, uveitis (e.g., anterior, intermediate, posterior, or panuveitis), Behcet's disease, Biett's crystalline dystrophy, blepharitis, glaucoma (e.g., open-angle glaucoma), neovascular glaucoma, neovascularization of the cornea, choroidal neovascularization (CNV), subretinal neovascularization, corneal inflammation, and complications from corneal transplantation.

Pharmaceutical Dosages

Dosages and desired drug concentration of pharmaceutical compositions of the present invention may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles laid down by Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46.

For in vivo administration of the fusion polypeptides described herein, normal dosage amounts may vary from about 10 ng/kg up to about 100 mg/kg of an individual's body weight or more per day, preferably about 1 mg/kg/day to 10 mg/kg/day, depending upon the route of administration. For repeated administrations over several days or longer, depending on the severity of the disease or disorder to be treated, the treatment is sustained until a desired suppression of symptoms is achieved.

An exemplary dosing regimen comprises administering an initial dose of a fusion protein of about 2 mg/kg, followed by a weekly maintenance dose of about 1 mg/kg every other week. Other dosage regimens may be useful, depending on the pattern of pharmacokinetic decay that the physician wishes to achieve. For example, dosing an individual from one to twenty-one times a week is contemplated herein. In certain embodiments, dosing ranging from about 3 µg/kg to about 2 mg/kg (such as about 3 µg/kg, about 10 µg/kg, about 30 µg/kg, about 100 µg/kg, about 300 µg/kg, about 1 mg/kg, and about 2/mg/kg) may be used. In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. Progress of the therapy is easily monitored by conventional techniques and assays. The dosing regimen, including the fusion protein administered, can vary over time independently of the dose used.

Dosages for a particular fusion protein may be determined empirically in individuals who have been given one or more administrations of fusion protein. Individuals are given incremental doses of a fusion protein. To assess efficacy of a fusion protein, a clinical symptom of an inflammatory disease (such as AMD) can be monitored.

Administration of a fusion protein according to the methods of the invention can be continuous or intermittent, depending, for example, on the recipient's physiological condition, whether the purpose of the administration is therapeutic or prophylactic, and other factors known to skilled practitioners. The administration of a fusion protein may be essentially continuous over a preselected period of time or may be in a series of spaced doses, e.g., either during or after development of an inflammatory disease (such as AMD).

Guidance regarding particular dosages and methods of delivery is provided in the literature; see, for example, U.S. Pat. Nos. 4,657,760; 5,206,344; or 5,225,212. It is within the scope of the invention that different formulations will be effective for different treatments and different diseases or disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

Administration of the Formulations

A fusion protein of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g., by injections, such as intravenous or subcutaneous injections, depending in part on whether the administration is brief or chronic. Various dosing schedules including but not limited to single or multiple administrations over various timepoints, bolus administration, and pulse infusion are contemplated herein. In some embodiments, the compositions are administered directly to the eye or the eye tissue. In some embodiments, the compositions are administered topically to the eye, for example, in eye drops. In some embodiments, the compositions are administered by injection to the eye (intraocular injection) or to the tissues associated with the eye. The compositions can be administered, for example, by intraocular injection, periocular injection, subretinal injection, intravitreal injection, trans-septal injection, subscleral injection, intrachoroidal injection, intracameral injection, subconjectval injection, subconjunctival injection, sub-Tenon's injection, retrobulbar injection, peribulbar injection, or posterior juxtascleral delivery. The compositions may also be administered, for example, to the vitreous, optic nerve, aqueous humor, sclera, conjunctiva, the area between the sclera and conjunctiva, the retina choroids tissues, macula, or other area in or proximate to the eye of an individual. In some embodiments, the compositions are administered to the individual as an ocular implant.

Fusion proteins of the invention would be formulated, dosed, and administered in a fashion consistent with good medical practice. Factors for consideration in this context include the particular disease or disorder being treated, the particular mammal being treated, the clinical condition of the individual patient, the cause of the disease or disorder, the site of delivery of the agent, the method of administration, the scheduling of administration, and other factors known to medical practitioners. The fusion protein need not be, but is optionally formulated with one or more agents currently used to prevent or treat the disease or disorder in question. The effective amount of such other agents depends on the amount of fusion protein present in the formulation, the type of disease or disorder or treatment, and other factors discussed above. These are generally used in the same dosages and with administration routes as described herein, or about from 1 to 99% of the dosages described herein, or in any dosage and by any route that is empirically/clinically determined to be appropriate.

Combination Treatment

Fusion proteins of the invention can be used either alone or in combination with one or more additional therapeutic agents. Such combination therapies encompass combined administration (where two or more therapeutic agents are included in the same or separate formulations), and separate administration, in which case, administration of the fusion protein of the invention can occur prior to, simultaneously, and/or following, administration of the additional therapeutic agent and/or adjuvant.

In some embodiments, a fusion protein is administered in combination with a therapeutic agent including, but not limited to, a complement inhibitor (e.g., ARC1905, TT30, Compstatin, and/or POT-4), a complement antibody (e.g. Eculizumab, FCFD4514S, TNX-558, and/or TNX-234), a VEGFR inhibitor (e.g., Sunitinib, Sorafenib, Vatalanib, and/or Vandetanib), VEGFR antibody (e.g., Ramucirumab), or VEGF antibody (e.g., Bevacizumab, Ranibizumab, Aflibercept, and/or Pegaptanib). For exemplary agents against complement proteins see Ehrnthaller, C., et al, (2011), Mol. Med., 17: 317-329. In further embodiments, a fusion protein is administered in combination with agents including, but not limited to, antioxidants (e.g., vitamin C, vitamin E, beta-carotene, lutein and/or zeaxanthin), long chain omega-3 fatty acids (e.g., docosahexaemoic acid and/or eicosapentaenoic acid), zinc or copper. In a further embodiment, a fusion protein is administered in combination with neuroprotectant cytokines including, but not limited to, ciliary neurotrophic factor. In further embodiments, a fusion protein is administered in combination with laser treatment (e.g., photodynamic therapy) in the case of AMD. In some embodiments, the combination of an effective amount of the fusion protein with one or more additional therapeutic agents is more efficacious compared to an effective amount of the fusion protein or other therapeutic agent alone.

In some embodiments, the fusion protein is administered by a different route of administration than one or more additional therapeutic agents. In some embodiments, one or more additional therapeutic agents are administered parentally (e.g., central venous line, intra-arterial, intravenous, intramuscular, intraperitoneal, intradermal, or subcutaneous injection), orally, gastrointestinally, topically, naso-pharyngeal and pulmonary (e.g. inhalation or intranasally).

VII. Compositions

Pharmaceutical formulations of a fusion protein as described herein are prepared by mixing such fusion protein having the desired degree of purity with one or more optional pharmaceutically acceptable carriers in the form of lyophilized formulations or aqueous solutions. Pharmaceutically acceptable carriers, excipients, or stabilizers are described herein and well known in the art (Remington: The Science and Practice of Pharmacy, 20th edition, Mack Publishing (2000)). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides;

proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). In one aspect, a sHASEGP is combined with one or more additional glycosaminoglycanases such as chondroitinases.

The formulation herein may also contain more than one active ingredients as necessary for the particular indication being treated, preferably those with complementary activities that do not adversely affect each other. For example, it may be desirable to further provide a VEGF antibody or complement inhibitor. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

In some embodiments, the pharmaceutical formulations comprising the fusion protein is suitable for parenteral administration. Among the acceptable vehicles and solvents are water, Ringer's solution, phosphate buffered saline, and isotonic sodium chloride solution. In addition, sterile, fixed oils are conventionally employed as a solvent or suspending medium. For this purpose any bland fixed mineral or non-mineral oil may be employed including synthetic mono- or diglycerides. In addition, fatty acids such as oleic acid find use in the preparation of injectables. In some embodiments, the pharmaceutical formulations comprising the fusion protein are suitable for subcutaneous, intramuscular, intraperitoneal, or intravenous delivery.

Sustained-release preparations may be prepared. Suitable examples of sustained-release preparations include semipermeable matrices of solid hydrophobic polymers containing the fusion protein, which matrices are in the form of shaped articles, e.g., films, or microcapsules. The pharmaceutical compositions are suitable for use in a variety of drug delivery systems. For a brief review of present methods for drug delivery, see Langer, R. (1990) *Science* 249:1527-33 (1990), which is incorporated herein by reference.

The formulations to be used for in vivo administration are generally sterile. Sterility may be readily accomplished, e.g., by filtration through sterile filtration membranes.

VIII. Articles of Manufacture or Kits

In another aspect, an article of manufacture or kit is provided which contains a fusion protein formulation. The article or kit may further comprise instructions for its use in the methods of the invention. Thus, in certain embodiments, the article of manufacture or kit comprises instructions for the use of fusion protein in methods for treating or preventing an inflammatory disease (such as age-related macular degeneration), complement-related disease, and/or cancer in an individual comprising administering to the individual an effective amount of a fusion protein. In certain embodiments, the individual is a human.

The article of manufacture or kit may further comprise a container. Suitable containers include, for example, bottles, vials (e.g., dual chamber vials), syringes (such as single or dual chamber syringes) and test tubes. The container may be formed from a variety of materials such as glass or plastic. The container holds the formulation. The article of manufacture or kit may further comprise a label or a package insert, which is on or associated with the container, may indicate directions for reconstitution and/or use of the formulation. The label or package insert may further indicate that the formulation is useful or intended for subcutaneous or other modes of administration for treating or preventing an inflammatory disease (such as age-related macular degeneration), complement-related disease, and/or cancer in an individual. The container holding the formulation may be a single-use vial or a multi-use vial, which allows for repeat administrations (e.g. from 2-6 administrations) of the reconstituted formulation. The article of manufacture or kit may further comprise a second container comprising a suitable diluent (e.g., BWFI). Upon mixing the diluent and the lyophilized formulation, the final protein, polypeptide, or small molecule concentration in the reconstituted formulation will generally be at least 50 mg/ml. The article of manufacture or kit may further include other materials desirable from a commercial, therapeutic, and user standpoint, including other buffers, diluents, filters, needles, syringes, and package inserts with instructions for use.

The article of manufacture or kit herein optionally further comprises a container comprising a second medicament, wherein the fusion polypeptide is a first medicament, and which article further comprises instructions on the package insert for treating the subject with the second medicament, in an effective amount. The second medicament may be any of those set forth above, with an exemplary second medicament being a complement inhibitor (e.g., ARC1905, TT30, Compstatin, and/or POT-4), a complement antibody (e.g. Eculizumab, FCFD4514S, TNX-558, and/or TNX-234), a VEGFR inhibitor (e.g., Sunitinib, Sorafenib, Vatalanib, and/or Vandetanib), VEGFR antibody (e.g., Ramucirumab), or VEGF antibody (e.g., Bevacizumab, Ranibizumab, Aflibercept, and/or Pegaptanib) if the fusion protein is used for treating age-related macular degeneration.

In another embodiment, provided herein is an article of manufacture or kit comprising the formulations described herein for administration in an auto-injector device. An auto-injector can be described as an injection device that upon activation, will deliver its contents without additional necessary action from the patient or administrator. They are particularly suited for self-medication of therapeutic formulations when the delivery rate must be constant and the time of delivery is greater than a few moments.

Also provided are unit dosage forms for the treatment and/or prevention of inflammatory disease (such as age-related macular degeneration), complement-related disease, and/or cancer, the dosage forms comprising any one of the fusion proteins or formulations described herein.

The invention will be more fully understood by reference to the following examples. They should not, however, be construed as limiting the scope of the invention. All citations throughout the disclosure are hereby expressly incorporated by reference.

VIIII. Exemplary Embodiments

1. A fusion protein that inhibits the complement activation and the VEGF signaling pathway, wherein the fusion proteins contains a complement inhibiting domain (CID), a VEGF inhibiting domain (VID), and a half-life prolonging domain;
2. The half-life prolonging domain in embodiment 1 is an immunoglobulin Fc region, wherein the Fc region is of a wild-type or a variant of any human immunoglobulin isotypes, subclasses, allotypes;
3. The Fc region in embodiment 2 is the Fc region with sequence in SEQ ID NO 7;
4. The half-life prolonging domain in embodiment 1 is an antibody, a fragment of antibody, Human Serum Albumin, or any other human proteins with long half-life in vivo;
5. The CID and the VID in embodiment 2 can be at either terminals of the Fc region, or at the same terminals of the Fc region, i.e., VID-Fc-CID, CID-Fc-VID, VID-CID-Fc, CID-VID-Fc, Fc-VID-CID, or Fc-CID-VID;
6. The CID in embodiment 1 is a portion of human Complement Receptor Type 1 (CR1) extracellular region; wherein the sequences of CIDs are from SEQ ID NO 1-6;
7. The CID in embodiment 1 is a portion of human DAF, MCP, Factor H, C4BP, wherein the sequences of CIDs are from SEQ ID NO 13-16;
8. The CID in embodiment 1 is an antibody fragment, or a scFv, or variable regions (VH or VK) of antibodies against Factor B, or Factor D, or Factor P, C3, or C5;
9. The CID in embodiment 1 is a peptide inhibitor or an oligonucleotide inhibitor to Factor B, or Factor D, or Factor P, C3, or C5;
10. The CID in embodiment 1 is a variant or a combination of the CIDs in embodiments 5-8;
11. The VID in embodiment 1 contains portions of the extracellular domains of VEGFRs;
12. The VID in embodiment 1 is the $2^{nd}$ extracellular domain of VEGFR-1 and the $3^{rd}$ extracellular domain of VEGFR-2 with sequence in SEQ ID NO 11;
13. The fusion protein in embodiment 1 has the sequence in SEQ ID NO 12.
14. A fusion protein that inhibits the complement activation, wherein the fusion protein contains a CID and a half-life prolonging domain;
15. The half-life prolong domain in embodiment 14 is an immunoglobulin Fc region, wherein the Fc region is of a wild-type or a variant of any human immunoglobulin isotypes, subclasses, and allotypes;
16. The Fc region in embodiment 15 is the Fc region with sequence in SEQ ID NO 7;
17. The half-life prolonging domain in embodiment 14 is an antibody, a fragment of antibody, Human Serum Albumin, or any other human proteins with long half-life in vivo;
18. The CID in embodiment 14 can be at either terminals of the Fc region, i.e., CID-Fc or Fc-CID;
19. The CID in embodiment 14 is a portion of human Complement Receptor Type 1 (CR1) extracellular region; wherein the sequences of CIDs are from SEQ ID NO 1-6;
20. The CID in embodiment 14 is a portion of human DAF, or MCP, or Factor H, or C4BP, wherein the sequences of CIDs are from SEQ ID NO 13-16;
21. The CID in embodiment 14 is an antibody fragment, or a scFv, or variable regions (VH or VK) of antibodies against Factor B, or Factor D, or Factor P, or C3, or C5;
22. The CID in embodiment 14 is a peptide inhibitor or an oligonucleotide inhibitor to Factor B, or Factor D, or Factor P, C3, or C5;
23. The CID in embodiment 14 is a variant or a combinations of the CIDs in embodiments 19-22;
24. A modified protein containing at least one of, or a variant, or a combination of the CIDs in embodiments 5-8, wherein the peptide is conjugated with a half-life prolonging domain;
25. The modified protein in embodiment 24 contains a VID in embodiments 11-12;
26. The half-life prolonging domain in embodiment 24 is a PEG or another polymer with long half-life in vivo;
27. The half-life prolonging domain in embodiment 24 is an immunoglobulin Fc region, wherein the Fc region is of a wild-type or a variant of any human immunoglobulin isotypes, subclasses, allotypes;
28. The half-life prolonging domain in embodiment 24 is an antibody, a fragment of antibody, Human Serum Albumin, or any other human proteins with long half-life in vivo.

EXAMPLES

Example 1: Expression and Purification of Anti-Complement Proteins (ACPs)

To produce a series of fusion proteins comprising a complement inhibiting domain (CID) and an Fc domain, cDNAs encoding various CIDs were synthesized and fused to the N-terminal end (see ACP-1-ACP-5 in FIG. 1A) or to the C-terminal end (see ACP-6-ACP-10 of FIG. 1A) of the IgG1 Fc domain. CIDs were portions of the extracellular region of human CR1. Specifically, CID-WT of ACP-1 and ACP-6 was wild-type human CR1 SCR1-3; CID-KN of ACP-2 and ACP-7 was human CR1 SCR1-3 with the amino acid substitution mutations N29K and D109N; CID-YD of ACP-3 and ACP-8 was human CR1 SCR1-3 with the amino acid substitution mutations S37Y and G79D; CID-KYDN of ACP-4 and ACP-9 was human CR1 SCR1-3 with the amino acid substitution mutations N29K, S37Y, G79D and D109N; and CID-NT of ACP-5 and ACP10 was human CR1 SCR 8-10 (FIG. 1A). The synthesized CID cDNAs and IgG1 Fc domain was ligated into an EcoRI/Not I-digested pCI-neo mammalian expression vector (Promega Catalog No. E1841). A short flexible peptide of six glycine residues was used between the CID and the Fc domain. All Fc fusion proteins contained the signal peptide SP2 at the N-termini to permit extracellular secretion of the ACPs.

Figure 2A:
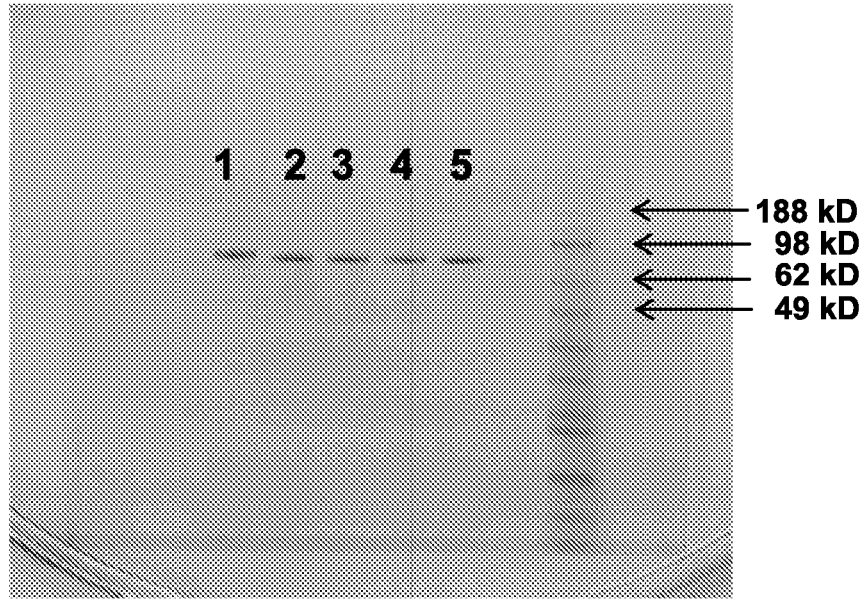
FIG. 2 shows SDS-PAGE gels of purified fusion proteins. A) Purified fusion proteins ACP-10 (lane 1), ACP-9 (lane 2), ACP-8 (lane 3), ACP-7 (lane 4), and ACP-6 (lane 5). B) Purified fusion protein ACVP-1 under non-reducing conditions (lane 1) and reducing conditions (lane 3); and purified fusion protein ACP-9 under non-reducing conditions (lane 2) and reducing conditions (lane 4).

Constructed plasmids for ACP-1 to ACP-10 were each transiently transfected into HEK293 cells. The cell culture media into which the ACPs were secreted was harvested 72 hours after transfection, and each ACP was purified via Protein A chromatography. Briefly, culture supernatants containing the secreted ACPs were mixed with Protein A agarose beads overnight before applying to a polypropylene column. The beads were washed with 0.1M Tris, pH 8.0 before elution of the ACPs with elution buffer (0.1M glycine buffer, pH 2.5) and neutralization with Tris buffer pH 8.0. The eluted ACPs were concentrated and dialyzed against phosphate buffered saline (PBS) before final protein concentration determination by the BCA assay. The purity of each isolated ACP was determined to be >90%. A 2 μg sample of each purified ACP-6 (lane 5), ACP-7 (lane 4), ACP-8 (lane 3), ACP-9 (lane 2), and ACP-10 (lane 1) protein was loaded onto an SDS-PAGE gel under non-reducing condition (FIG. 2A). The molecular weights of the dimeric Fc fusion proteins were ~94 kD.

ACPs in which DAF SCR2-4, MCP SCR2-4, Factor H SCR 1-4, or C4BPA SCR1-3 are each fused as a CID to the IgG1 Fc domain constructed, expressed, and purified in a similar manner.

Example 2: Inhibition of the Classical Complement Pathway by ACPs

The CH50 assay was used to quantify the degree of activity of the classical complement pathway. This assay determines the functional capability of serum complement components of the classical pathway (i.e., present in a sample) to lyse sheep red blood cells pre-coated with rabbit anti-sheep red blood cell antibody (EA, antibody sensitized sheep erythrocytes, Complement Technology Catalog No. B200). When EA are incubated with, e.g., test serum, magnesium ions, and calcium ions, the classical pathway of complement is activated and hemolysis results. A fixed volume of optimally sensitized EA is added to each serum dilution. After incubation, the mixture is centrifuged and the degree of hemolysis is quantified by measuring the absorbance of the hemoglobin released into the supernatant at ~540 nm. The amount of complement activity is determined by examining the capacity of various dilutions of test serum to lyse EA. The result of the assay is expressed as the reciprocal of the serum dilution required to produce lysis of 50% of defined numbers of erythrocytes under standard conditions.

The CH50 assay is sensitive to the reduction, absence and/or inactivity of any component of the classical complement pathway and was thus used to assess the abilities of ACP-6, -7, -9, and -10 to inhibit classical complement activation. For this assay, the dilution of the normal human serum (Complement Technology Catalog No. NHS) that lysed 90% of $1 \times 10^7$ EA/ml after 1 hour incubation at 37° C. was first determined. The assay was carried out in GVB$^{++}$ buffer (0.1% gelatin, 5 mM Veronal, 145 mM NaCl, 0.025% NaN$_3$, pH 7.3) containing 0.15 mM CaCl$_2$ and 0.5 mM MgCl$_2$. Inhibition of the classical complement pathway was activated by mixing the dilution of normal human serum that could lyse 90% of EA with 0-500 nM of fusion proteins ACP-6, ACP-7, ACP-9, or ACP-10 for 1 hour at 37° C. Hemolysis of EA was then assayed after 1 hour incubation of the serum and EA by measuring absorption at OD541 nm. The data was analyzed by sigmoidal curve fitting using Prism 4 (GraphPad, Inc.).

Figure 3A:
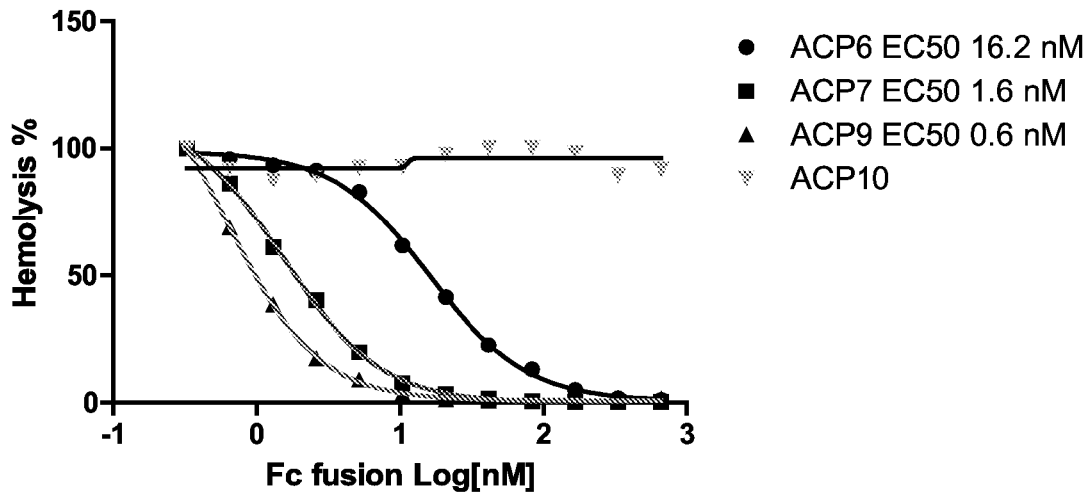
FIG. 3 is a series of graphs demonstrating inhibition of the complement pathway by fusion proteins ACPs. A) Inhibition of the classical complement pathway in antibody-sensitized sheep erythrocytes by various concentrations of fusion proteins ACP-6, ACP-7, ACP-9 and ACP-10. B) Inhibition of the alternative complement pathway in rabbit erythrocytes by various concentrations of fusion proteins ACP-6, ACP-7, ACP-9 and ACP-10. Fc fusion Log [nM] is log concentration of the indicated fusion protein (nM).

Analysis of the percentage of hemolysis of the EA in the presence of the fusion proteins demonstrated that ACP-6, in which the human CR1 SCR1-3 domain was fused to the C-terminal end of IgG1 Fc, exhibited robust inhibition of the complement activity with EC50 of 16.2 nM (FIG. 3A, closed circle). ACP-7, in which the human CR1 SCR1-3 N29K/D109N variant was fused to the C-terminal end of IgG1 Fc, significantly enhanced the inhibitory effect 10-fold to EC50 of 1.6 nM (FIG. 3A, closed square). ACP-9, in which the human CR1 SCR1-3 N29K/D109N S37Y/G79D variant was fused to the C-terminal end of IgG1, boosted the inhibitory activity further 2.7-fold to EC50 of 0.6 nM (FIG. 3A, closed triangle). In contrast, ACP-10, in which the human CR1 SCR 8-10 was fused to the C-terminal end of IgG1, did not show any inhibition on the complement activity up to 500 nM (FIG. 3A, inverted triangle).

Inhibition of the classical complement pathway by ACPs containing DAF SCR2-4, MCP SCR2-4, Factor H SCR 1-4, or C4BPA SCR1-3 CIDs are assayed similarly.

Example 3: Inhibition of the Alternative Complement Pathway by ACPs

In contrast to the classical and lectin complement pathways, which require both magnesium and calcium ions for activation, activation of the alternative complement pathway requires only magnesium ions. Thus, to quantify alternative complement activity in the presence of ACPs, the assay described above was modified such that rabbit erythrocytes (Er) were incubated with serum, 0-500 nM ACP, 5 mM Mg$^{2+}$, and 5 mM EGTA, which preferentially chelates calcium ions.

For this assay, the dilution of normal human serum (Complement Technology Catalog No. NHS) that lysed 90% of $1.25 \times 10^7$ rabbit erythrocytes/ml (Er, Complement Technology Catalog No. B300) was first determined after 30 minutes incubation at 37° C. The assay was performed in GVB$^0$ buffer (0.1% gelatin, 5 mM Veronal, 145 mM NaCl, 0.025% NaN$_3$, pH 7.3) containing 5 mM of MgCl$_2$ and 5 mM of EGTA. Inhibition of the alternative complement pathway was initiated by mixing the dilution of normal human serum that should lyse 90% of Er with 0-500 nM of the Fc fusion proteins ACP-6, ACP-7, ACP-9, or ACP-10 for 1 hour at 37° C. Hemolysis of Er was then assayed after 30 minutes incubation of the serum and Er by measuring absorption at OD412 nm. The data was analyzed by sigmoidal curve fitting using Prism 4.

Figure 3B:
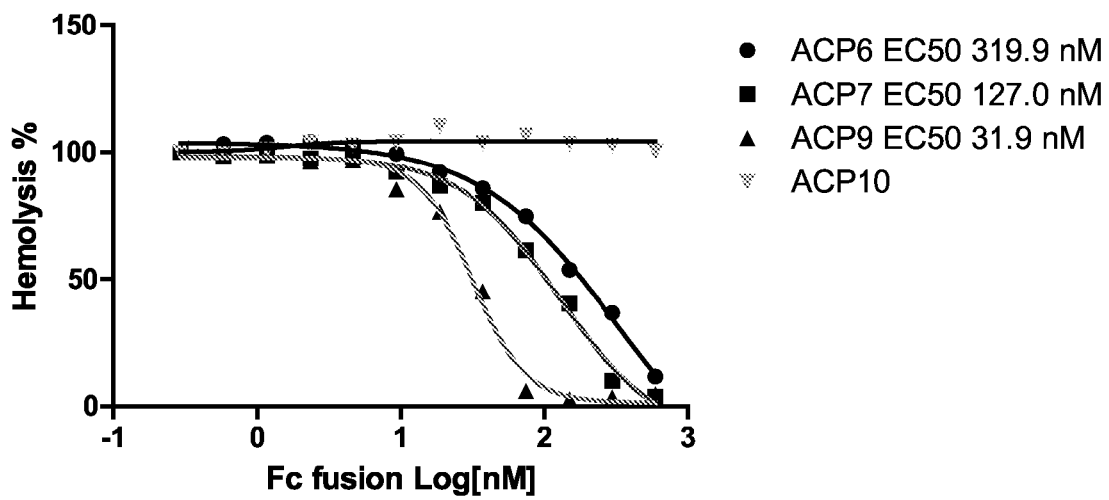

Analysis of the percentage of hemolysis of the EA in the presence of the fusion proteins demonstrated that ACP-6 exhibited a very low inhibitory activity with EC50 of 319.9 nM (FIG. 3B, closed circle). ACP-7 exhibited an improved inhibitory effect (2.5-fold) to EC50 of 127.0 nM (FIG. 3B, closed square). ACP-9 exhibited an even higher inhibitory effect to EC50 of 31.9 nM, i.e., 10 times better than the wild-type sequence (APC-6) (FIG. 3B, closed triangle). In contrast, ACP-10 did not show any effect on the complement activity up to 500 nM (FIG. 3B, inverted triangle).

Inhibition of the alternative complement pathway by ACPs containing DAF SCR2-4, MCP SCR2-4, Factor H SCR 1-4, or C4BPA SCR1-3 CIDs were assayed similarly.

Figure 1B:
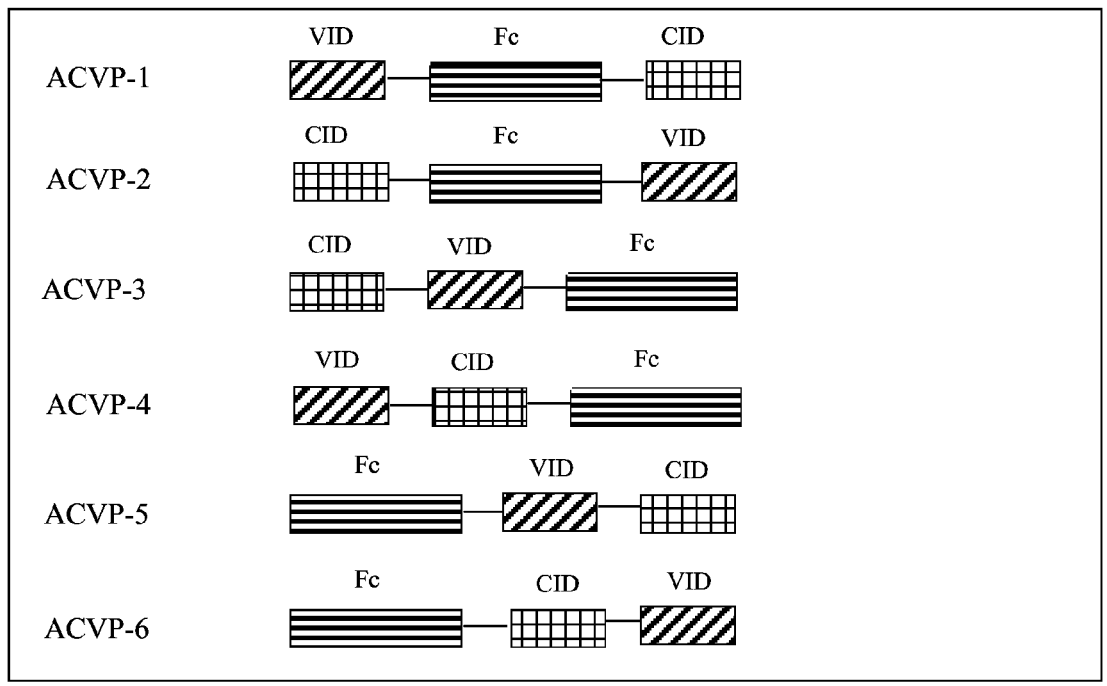
Figure 2B:
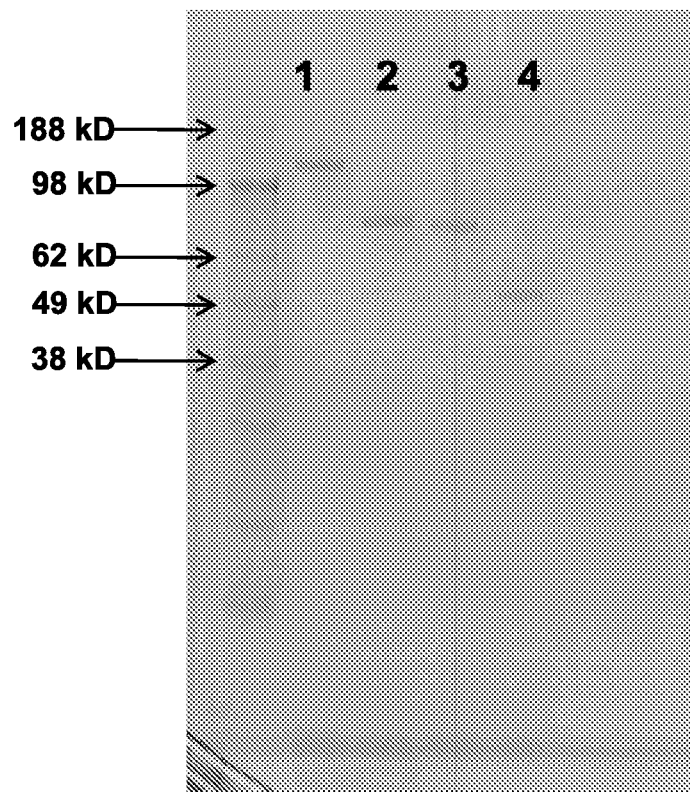

Example 4: Expression and Purification of Bispecific Protein ACVPs that Inhibited Both Complement and VEGF Pathways A series of bispecific fusion proteins comprising a complement inhibiting domain (CID), a VEGF-inhibiting domain (VID), and an Fc domain (i.e., the human IgG1 Fc region) were produced (FIG. 1B). The VID used for the bispecific fusion proteins was a VEGFR1_D2-VEGFR2_D3 fusion of the second Ig-like domain of VEGFR1 and the 3$^{rd}$ Ig-like domain of VEGFR2, i.e., similar to VEGF-trap-eye, which is also known as Aflibercept (see, e.g., Frampton (2012). *Drugs Aging* 29: 839-46 and Ohr et al. (2012). *Expert Opin. Pharmacother.* 13: 585-91). A nucleic acid encoding the fusion protein ACVP-1 was constructed by inserting a nucleic acid encoding the VID downstream of the SP2 signal peptide at the N-terminal of ACP-9 into the plasmid pV131. The constructed ACVP-1 plasmid was used transiently transfected into HEK293 cells. The cell culture media containing the secreted ACVP-1 was harvested 72 hours after transfection, and the protein was purified via Protein A chromatography. Briefly, the culture supernatant containing secreted ACVP-1 was mixed with Protein A agarose beads overnight before applying to a polypropylene column. The beads were washed with 0.1M Tris, pH 8.0 before elution of the ACVP-1 with elution buffer (0.1M glycine buffer, pH 2.5) and neutralization with Tris buffer pH 8.0. The eluted protein was concentrated and dialyzed against phosphate buffered saline (PBS) before final protein concentration determination by the BCA assay. The purity of each isolated ACVP-1 was determined to be >90%. A 2 µg sample of purified ACVP-1 (lanes 1 and 3) was compared to purified ACP-9 (lanes 2 and 4) by running on an SDS-PAGE gel under reducing (lanes 3 and 4) or non-reducing conditions (lanes 1 and 2) (FIG. 2B). The molecular weight of the dimeric ACVP-1 was ~139 kD.

The positions of the Fc domain, CID, and VID of ACVP-1 are rearranged relative to one another. In addition, the alternate CIDs, such as those present in the ACPs, and alternate VIDs are used. Nucleic acid constructs encoding any of the ACVPs depicted in FIG. 1B are prepared and expressed in mammalian cells, as described above. Similarly, such ACVPs are purified via Protein A chromatography, as described herein.

ACVPs containing DAF SCR2-4, MCP SCR2-4, Factor H SCR 1-4, or C4BPA SCR1-3 CIDs are constructed.

Example 5: In Vitro Binding of ACVPs to VEGF

Figure 4A:
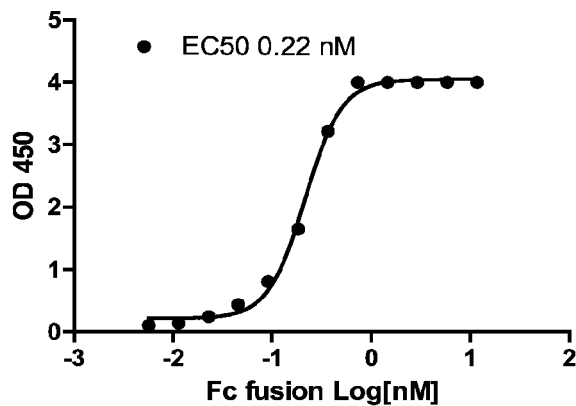
FIG. 4 is a series of graphs demonstrating in vitro binding of a VEGF by fusion proteins as detected by ELISA. A) Direct in vitro binding of mobilized VEGF by ACVP-1. B) In vitro binding of soluble VEGF by ACVP-1. C) In vitro binding of VEGF by ACVP-1, VID, or Avastin.

ELISAs were performed to determine whether ACVPs bind directly to VEGF. Briefly, the wells of a 96-well ELISA plate were coated with 100 ng VEGF-A (available from R&D Systems). 0-10 nM of purified ACVP was then added to each well and incubated for 1 hour. After washing three times with 400 µL PBS containing 0.1% (v/v) Tween20, a 100 µl of a 1:5000 dilution of anti-Fc HRP conjugate (Sigma Catalog No. A0170-1ML) is added to each well for incubation of 1 hour. After washing three times with 400 µL PBS containing 0.1% (v/v) Tween20, stop reagent for TMB Substrate (Sigma Catalog No. S5814-100ML) was added to each well, and OD absorption at 450 nm was measured. The data was analyzed by sigmoidal curve fitting using Prism 4. As shown in FIG. 4A, ACVP-1 exhibited strong binding to VEGF, with an EC50 of 0.22 nM.

Figure 4B:
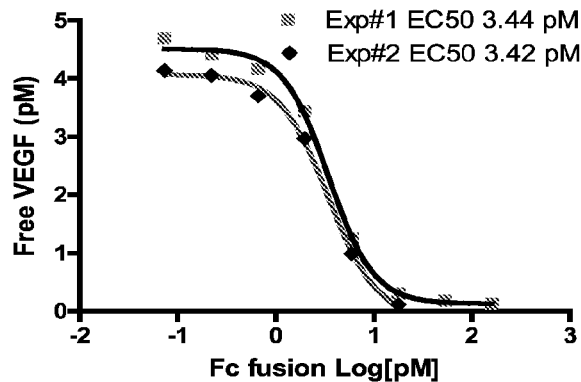

To better assess the binding affinity of ACVPs to VEGF in solution, 5 pM of VEGF-A was incubated with 0-100 pM of a purified ACVP overnight at 4° C. in dilution buffer RDSK (R&D Systems Catalog No. DVE00). Following incubation, the concentration of free VEGF in the buffer was determined via sandwich ELISA using the Human VEGF Quantikine ELISA Kit (R&D Systems Catalog No. DVE00). The data from two independent experiments using ACVP-1 was analyzed by sigmoidal curve fitting using Prism 4. As shown in FIG. 4B, ACVP-1 exhibited identical strong binding to VEGF with an affinity of 3.4 pM.

Figure 4C:
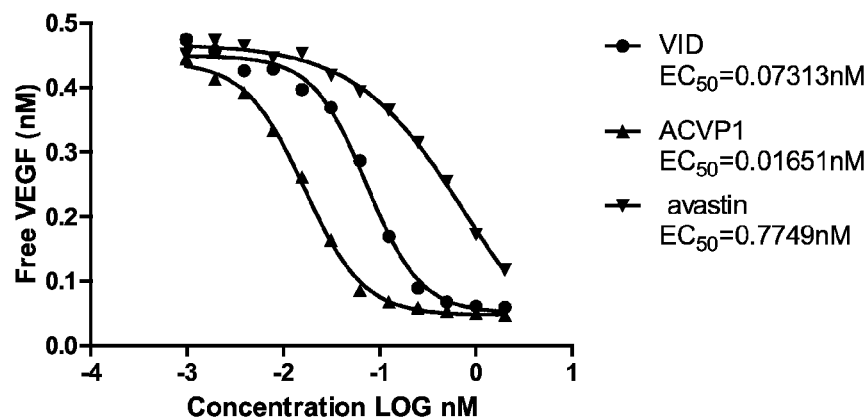

ELISAs were also performed to compare the binding affinities of ACVP-1, VID, and Avastin to VEGF-A. The tested VID was a fragment of ACVP-1 wherein the VID has the Fc domain fused to its C-terminus. About 40 pM of VEGF165 (293-VE) was incubated with 1 nM of purified ACVP-1, VID, or Avastin for 45 minutes at 37° C. After incubation, free VEGF was detected using the Human VEGF DuoSet ELISA Development Kit (R&D Systems Catalog No. DY293B) according to the manufacturer's instructions. The data was analyzed by sigmoidal curve fitting using Prism 4. As shown in FIG. 4C, ACVP-1 exhibits an affinity to VEGF (with an EC50 of ~0.01 nM) that is 70-fold higher than the binding of Avastin or VID to VEGF (each with an EC50 of ~0.7 nM).

Other ACVPs (e.g., containing DAF SCR2-4, MCP SCR2-4, Factor H SCR 1-4, or C4BPA SCR1-3 as CIDs) are assayed for their abilities to bind VEGF and to determine their binding affinities for VEGF as described above.

Example 6: In Vitro Binding of ACPs or ACVPs to C3b or C4b

Binding of ACPs or ACVPs to C3b or C4b are assayed in direct Elisa experiments. The wells of 96-well ELISA plates are coated with 100 ng/well of C3b or C4b (available from Complement Technology, Inc.). 0-1 µM of a purified ACP or ACVP depicted in FIG. 1 is then added to each well and incubated for 1 hour. After washing off unbound C3b or C4b, a 100 µl of a 1:5000 dilution of anti-Fc HRP conjugate (Sigma Catalog No. A0170-1ML) is added to each well and incubated 1 hour. After washing, stop reagent for TMB Substrate (Sigma Catalog No. S5814-100ML) is added, and OD450 nm absorptions are measured.

Example 7: Inhibition of DAA for the Alternative Convertases by ACPs or ACVPs

Decay-accelerating activity (DAA) for the alternative C3-convertase are determined by ELISA. The wells of 96-well ELISA plates are first coated with 1 µg/ml of C3b (available from Complement Technology, Inc.) and then blocked. Each well is then incubated with 400 ng/ml of Factor B (available from Complement Technology, Inc.), 25 ng/ml of Factor D (available complement Technology, Inc.), and 2 mM of $NiCl_2$. After washing, the plate-bound C3bBb ($Ni^{2+}$) complexes are incubated with varying concentrations of ACPs or ACVPs. After a second wash, the remaining plate-bound C3bBb($Ni^{2+}$) complexes are detected with goat anti-Factor B polyclonal antibody (available Complement Technology, Inc.) followed by HRP-conjugated rabbit anti-goat polyclonal antibody (Sigma, Inc.). After washing, stop reagent for TMB Substrate (Sigma Catalog No. S5814-100ML) is added, and OD450 nm absorptions are measured.

DAA for the alternative C5-convertase are determined by ELISA as described above, except the wells of the ELISA plates are coated with 1 µg/ml of C3b dimers. The C3b dimers are generated by treating 2 mg of C3 (available Complement Technology, Inc.) with 20 µg of trypsin (available from Sigma, Inc.) in 200 µl of PBS for 3 min at 37° C. The reaction is then stopped with 200 µg of soybean trypsin inhibitor (available from Sigma, Inc.). C3b dimers are then formed after breaking the thioester bond for 3 days at 4° C. using 15 µg of 0.34 mM bismaleimidohexane (available from Pierce, Inc.) dissolved in methanol. The C3b dimer is purified by SEC chromatography.

Example 8: Inhibition of the Classical Complement Pathway by ACVPs

Figure 5A:
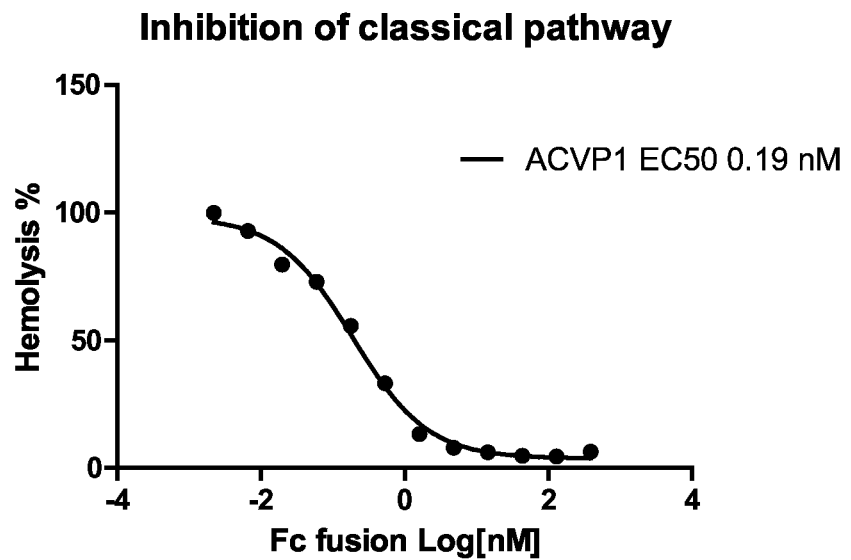
FIG. 5 is a series of graphs demonstrating inhibition of the complement pathway by fusion proteins ACVPs. A) Inhibition of the classical complement pathway in antibody-sensitized sheep erythrocytes by various concentrations of fusion protein ACVP-1. B) Inhibition of the alternative complement pathway in rabbit erythrocytes by various concentrations of fusion protein ACVP-1. Fc fusion Log [nM] is log concentration of the indicated fusion protein (nM).

The ability of ACVPs to inhibit the classical complement pathway was assayed as described in Example 2. The assay was carried out in GVB++ buffer (0.1% gelatin, 5 mM Veronal, 145 mM NaCl, 0.025% $NaN_3$, pH 7.3) containing 0.15 mM $CaCl_2$ and 0.5 mM $MgCl_2$. Inhibition of the classical complement pathway was activated by mixing the dilution of normal human serum that could lyse 90% of EA with 0-500 nM of ACVP-1 for 1 hour at 37° C. The inhibitory data was analyzed by sigmoidal curve fitting using Prism 4. As shown in FIG. 5A, the bispecific fusion protein ACVP-1 exhibited a very high potency of inhibitory effect on the classical complement activation, with an EC50 of 0.19 nM.

Other ACVPs (e.g., containing DAF SCR2-4, MCP SCR2-4, Factor H SCR 1-4, or C4BPA SCR1-3 as CIDs) are assayed as described herein to determine their abilities to inhibit the classical complement pathway.

Example 9: Inhibition of the Alternative Complement Pathway by ACVPs

Figure 5B:
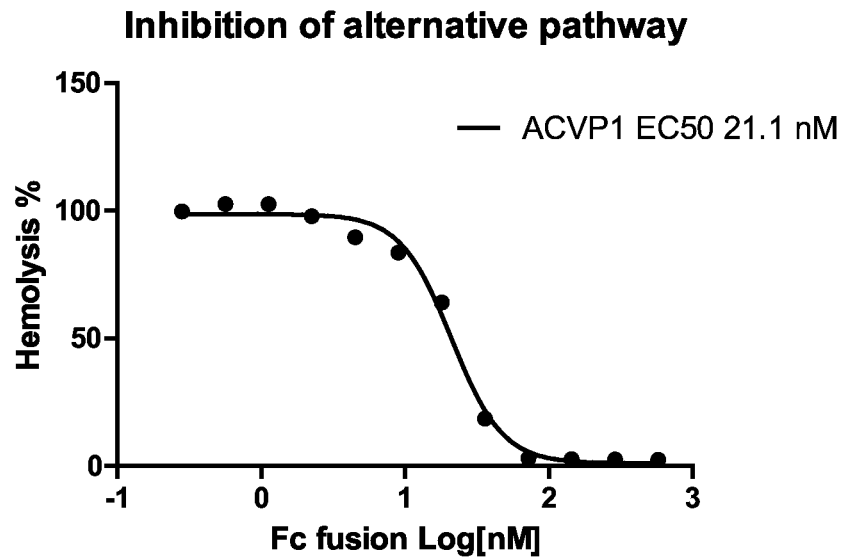

The ability of ACVPs to inhibit the alternative complement pathway was assayed as described in Example 3. The assay was performed in $GVB^0$ buffer (0.1% gelatin, 5 mM Veronal, 145 mM NaCl, 0.025% $NaN_3$, pH 7.3) containing 5 mM of $MgCl_2$ and 5 mM of EGTA. Inhibition of the alternative complement pathway was initiated by mixing the dilution of normal human serum that could lyse 90% of Er with 0-500 nM of ACVP-1 for 1 hour at 37° C. Hemolysis of Er was then assayed after 30 minutes incubation of the serum and Er. The inhibitory data was analyzed by sigmoidal curve fitting using Prism 4. As shown in FIG. 5B the bispecific ACVP-1 fusion protein exhibited a highly potent inhibitory effect on the alternative complement activation, with an EC50 of 21.1 nM.

Other ACVPs (e.g., containing DAF SCR2-4, MCP SCR2-4, Factor H SCR 1-4, or C4BPA SCR1-3 as CIDs) are assayed as described above to determine their abilities to inhibit the alternative complement pathway.

Example 10: Inhibition of VEGF-Dependent HUVEC Proliferation Assay by ACVPs

ACVPs are tested for the ability to inhibit VEGF signaling pathway (e.g., inhibition of VEGF activity) in a cell-based assay. Human Umbilical Vein Endothelial Cells (HUVECs, Lonza, Inc.) are often used to demonstrate VEGF-dependent cell proliferation which can be inhibited by binding of ACVPs to VEGF. In this assay, HUVECs are maintained in Endothelial Cell Growth Medium (Lonza, Inc.) with 2% FBS. A 96-well flat bottom microtiter plate is coated with collagen, and is then incubated with 50 µl of 1 nM of VEGF-A (R&D systems, Inc.) and various concentrations of ACVPs in each well for 1 hour at 37° C. After incubation for 1 hour, 50 µl of HUVECs at $1\times10^5$ cells/ml in Medium-199 (10% FBS, Hyclone, Inc.) is added to each well. After incubation for 72 hours at 37° C. with 5% $CO_2$, cell proliferation is assayed by adding 10 µl of CCK-8 (Dojindo, Inc.) to each well. Cell proliferation is measured at OD absorption of 450/650 nm.

Figure 6:
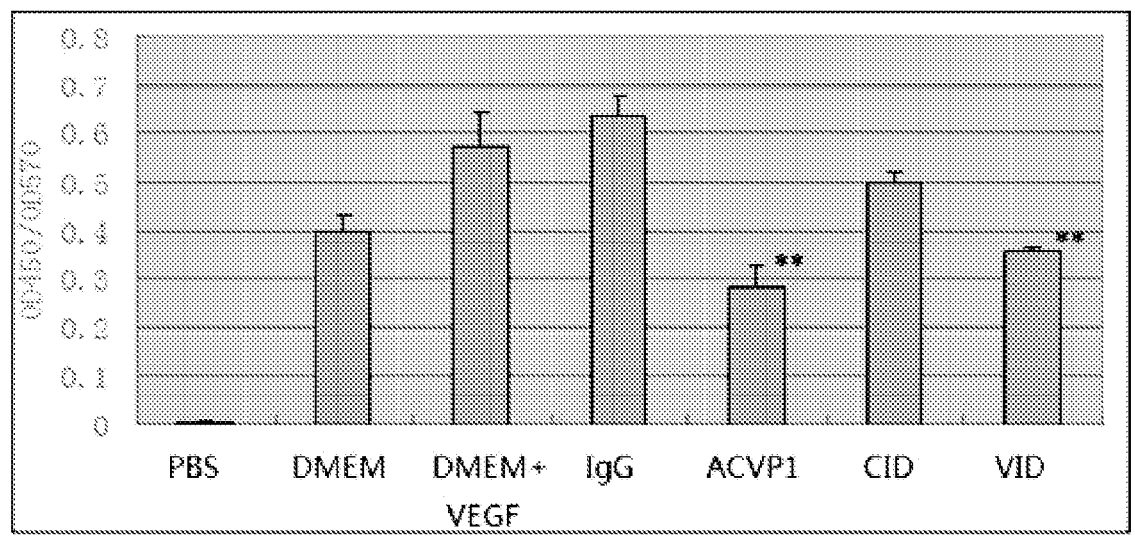
FIG. 6 is a graph demonstrating inhibition of VEGF-induced proliferation of human umbilical vein endothelial cells (HUVECs) by ACVP-1, VID, or CID fusion proteins. All assays were performed in triplicate. **p<0.01 as compared to DMEM+ VEGF control.

For example, ACVP-1 was tested for the ability to inhibit VEGF signaling pathway (e.g, inhibition of VEGF activity) in this cell-based assay and compared to the VEGF inhibitory activity of a CID and a VID. The tested VID was a fragment of ACVP-1 wherein the VID has the Fc domain fused to its C-terminus. The tested CID was a fragment of ACVP-1 wherein the CID has the Fc domain fused to its N-terminus. To measure endothelial cell proliferation, human umbilical vein endothelial cells (HUVECs, available from Lonza, Inc.), were seeded in 96-well plates ($4\times10^4$ cells/well) with EndoGRO-VEGF Complete Media Kit. After 24 hours, cells were washed with PBS and incubated with 35 nM per ml ACVP-1, VID, or CID in the presence of 0.3 nM VEGF165 in DMEM supplemented with 20% FBS. For controls, cells were incubated with PBS, DMEM supplemented with 20% FBS, 0.3 nM VEGF165 in DMEM with 20% FBS or with 35 nM per ml of IgG in DMEM with 20% FBS. After 48 hours, 10 µl CCK-8 (Dojindo, Inc.) was added to each well and cell proliferation was measured at an OD absorption of 450/570 nm on a microplate reader. Statistical analysis using the student t-test showed that ACVP-1 significantly inhibited VEGF-induced HUVEC proliferation as compared to the DMEM+VEGF control ($p<0.01$) and the inhibitory effect of ACVP-1 was greater than that of VID or CID (FIG. 6**).

Example 11: ACVPs Inhibit Activation of ERK and AKT in HUVECs Through the VEGFR2 Pathway ACVPs are tested for the ability to inhibit activation of downstream intracellular signaling by a VEGFR pathway. In this assay, HUVECs are pretreated with 3 nmol/ml of IgG, VID, CID, or an ACVP for 30 minutes and then stimulated with 3 nmol/ml $VEGF_{165}$ for an additional 10 minutes. Cells are harvested and analyzed by Western blot, in which VEGFR (e.g., VEGFR1, VEGFR2 or VEGFR3), AKT, and ERK phosphorylation are evaluated. GAPDH is used as a loading control. Blocked membranes are probed with primary antibodies against phosphorylated VEGFR (e.g., VEGFR1, VEGFR2 or VEGFR3), GAPDH (1:3000 dilution; Cell Signaling Technology, Beverly, Mass.), phosphorylated Erk (p-Erk), Erk protein, phosphorylated AKT (p-Akt), and Akt protein overnight at 4° C. After washing off the primary antibodies, secondary antibodies conjugated to horseradish peroxidase (HRP) are added to the membranes and incubated at room temperature for 1 hour before further washing and the protein was visualized with a chemiluminescent substrate for HRP.

Figure 7:
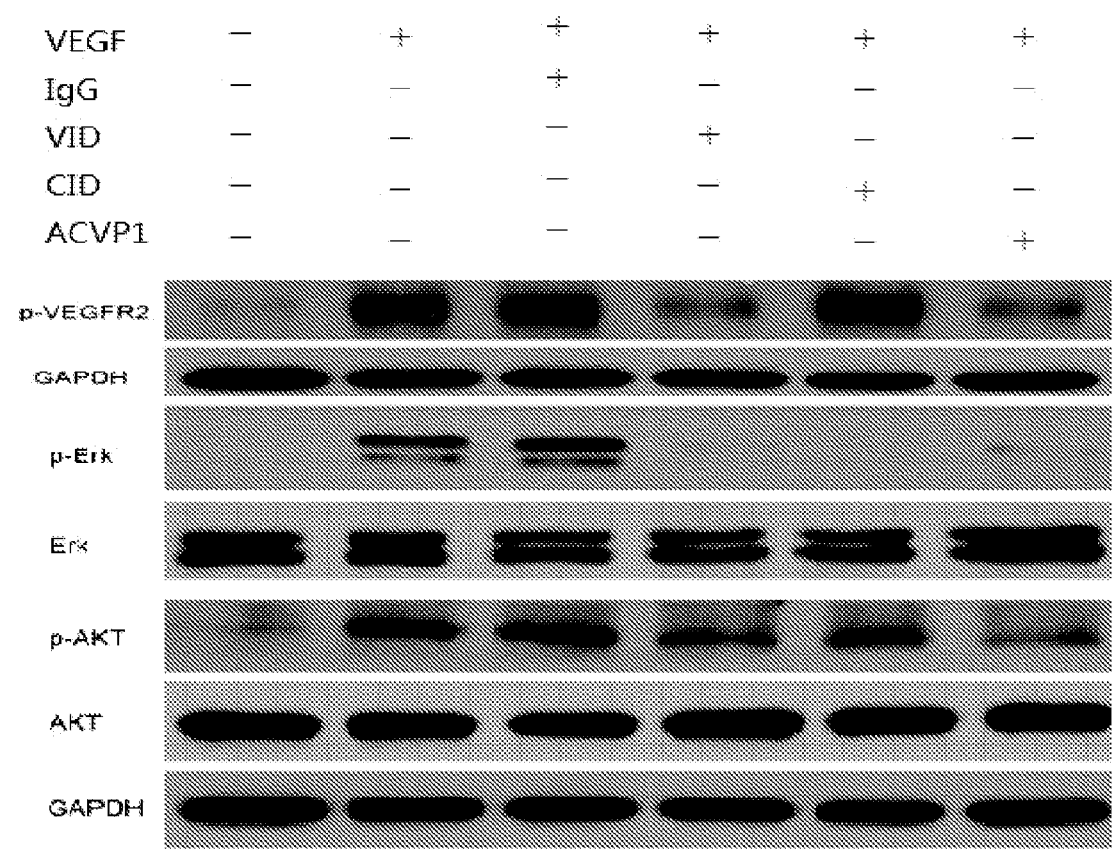
FIG. 7 is a western blot demonstrating inhibition of VEGFR2 pathway activation by fusion proteins ACVP-1, VID, or CID.

For example, ACVP-1 was tested for the ability to inhibit activation of ERK and AKT through the VEGFR2 pathway. In this assay, HUVECs were pretreated with 3 nmol/ml of IgG, VID, CID, or ACVP-1 for 30 minutes and then stimulated with 3 nmol/ml $VEGF_{165}$ for an additional 10 minutes. The tested VID was a fragment of ACVP-1 wherein the VID has the Fc domain fused to its C-terminus. The tested CID was a fragment of ACVP-1 wherein the CID has the Fc domain fused to its N-terminus. Cells were harvested and analyzed by Western blot, in which VEGFR2, AKT, and ERK phosphorylation were evaluated. GAPDH was used as a loading control. Blocked membranes were probed with primary antibodies against phosphorylated VEGFR2, (1:1000 dilution; Cell Signaling Technology, Beverly, Mass.), GAPDH (1:3000 dilution; Cell Signaling Technology, Beverly, Mass.), phosphorylated Erk (p-Erk), Erk protein, phosphorylated AKT (p-Akt), and Akt protein overnight at 4° C. After washing off the primary antibodies, secondary antibodies conjugated to horseradish peroxidase (HRP) were added to the membranes and incubated at room temperature for 1 hour before further washing and visualization of the protein by a chemiluminescent substrate for HRP. As shown in FIG. 7, ACVP-1 and VID inhibited $VEGF_{165}$ induced VEGFR2, ERK, and AKT phosphorylation, and CID inhibited ERK phosphorylation.

Example 12: Inhibition of Laser-Induced CNV in Mice by ACVPs

Choroidal neovascularization (CNV) is a common symptom of wet age-related macular degeneration (AMD). CNV occurs when new blood vessels that originate in the choroid layer of the eye grow through a break or defect in Bruch's membrane and invade the sub-retinal pigment epithelium or subretinal space. This process forms scar tissue that ultimately causes blindness. Laser-induced choroidal neovascularization (CNV) as an animal model is commonly used to test treatments for wet AMD. For example, this model can be used to assess the abilities of ACVPs to inhibit CNV.

Laser-induced CNV in mice is used to test the ability of ACVPs and ACPs to inhibit CNV. In this assay, mice are anesthetized with ketamine hydrochloride (100 mg/kg body weight) and the pupils are dilated with 1% tropicamide, three burns of 532 nm diode laser photocoagulation are delivered to each retina. Burns are performed in the 9, 12, and 3 o'clock positions of the posterior pole of the retina. Production of a bubble at the time of laser which indicates rupture of Bruch's membrane, is an important factor in obtaining CNV. To test the abilities of an ACVP or ACP to prevent formation of laser-induced CNV, 4 μg of an ACVP or ACP is injected intravitreally at the same day of laser burns. At 14 days following laser injury, the mice are injected intravenously with 50 mg fluorescein-labeled dextran and euthanized. The eyes of the mice are then dissected for choroidal flat mounts to assess the change in the size of CNV lesions.

Example 13: Inhibition of Laser-Induced CNV in Monkeys by ACVPs

Laser-induced CNV in monkey is used to test the ability of ACVPs and ACPs to inhibit CNV. Briefly, 6 to 9 burns of 532 nm diode laser photocoagulation are delivered around the macula in each eye. A dosage of 0.1 to 0.5 mg of an ACVP is injected intravitreally at the same day of laser burns. Around 20 days later, the animals are sedated with intravenous 2.5% soluble pentobarbitone (1 mL/kg). The eyelids are fixed to keep the eye open and accessible. Color photographs are first taken using a fundus camera. After the initial photograph, fluorescein dye (20% fluorescein sodium; 0.05 mL/kg) is injected via a vein of lower extremity. Photographs are taken at several time points after dye injection, including the arterial phase, early arteriovenous phase, and several late arteriovenous phases. Leakage of fluorescein associated with CNV lesions is monitored.

Figure 8:
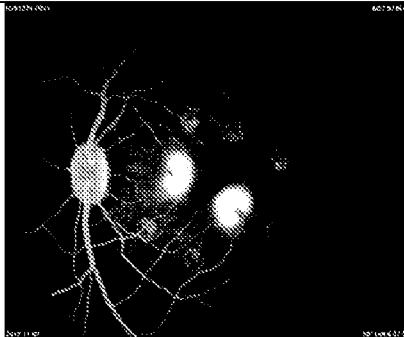
FIG. 8 is a series of photographs of eyes from a laser-induced CNV monkey model. Twenty-one days after 532 nm diode laser photocoagulation was delivered around the macula, monkeys were injected intravitreally with A) vehicle control (PBS); B) ACVP-1; C) VID; or D) CID at the indicated concentrations and photographs of the treated eye were taken 14-days post-dose to measure spot leakage.
Figure 8:
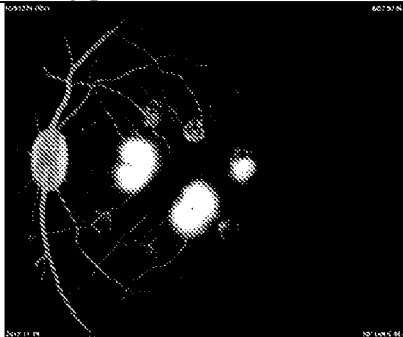
Figure 8:
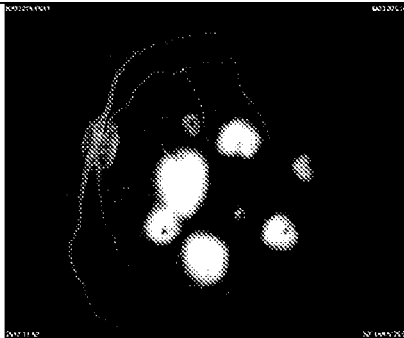
Figure 8:
Figure 8:
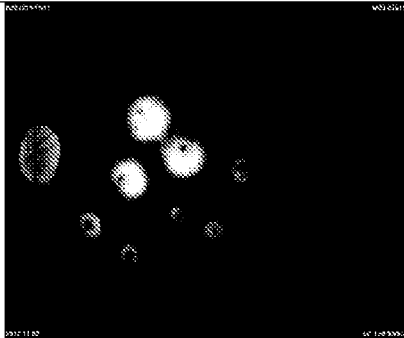
Figure 8:
Figure 8:
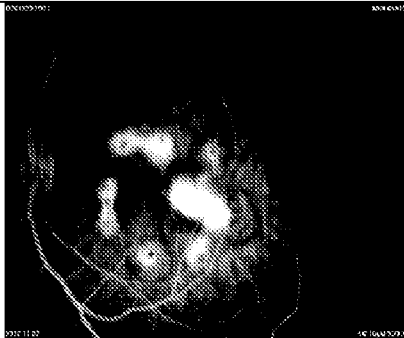
Figure 8:
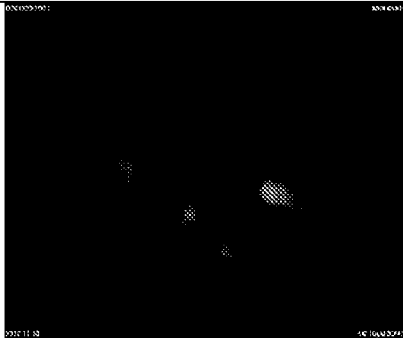

For example, a laser-induced CNV model was set up in Rhesus monkeys, ages ranging from 3 to 6 years old. A total of 8 monkeys were divided into the following four groups that were administered: 1) vehicle control (PBS); 2) ACVP1 (0.5 mg/eye); 3) VID (0.5 mg/eye); or 4) CID (0.5 mg/eye). In total there were two monkeys (four eyes) per group. The tested VID was a fragment of ACVP-1 wherein the VID has the Fc domain fused to its C-terminus. The tested CID was a fragment of ACVP-1 wherein the CID has the Fc domain fused to its N-terminus. Approximately 6 to 9 burns of 532 nm diode laser photocoagulation were delivered around the macula in each eye. Vehicle control (PBS) or a dosage of 0.5 mg ACVP-1, VID, or CID, was injected intravitreally at 21 days post laser burns. Fourteen days after dose administration, the animals were sedated with intravenous 2.5% soluble pentobarbitone (1 ml/kg). The eyelids were fixed to keep the eye open and accessible. Color photographs were first taken using a fundus camera. After the initial photograph, fluorescein dye (20% fluorescein sodium; 0.05 mL/kg) was injected via a vein of lower extremity. Photographs were taken at 5 minutes after dye injection, including the arterial phase, early arteriovenous phase, and several late arteriovenous phases to monitor leakage of fluorescein associated with CNV lesions. A spot area in the photo picture was measured as a leakage area. Analysis of the spot leakage photographs showed that that the mean leakage area in the vehicle treated group was larger at 14 days post-injection as compared to the leakage area before PBS injection (FIG. 8A). By contrast, leakage in monkeys injected with either ACVP-1 (FIG. 8B), VID (FIG. 8C), or CID (FIG. 8D) was reduced at 14 days post-injection as compared to the leakage area before injection. Statistical analysis using the student t-test showed that the spot number and leakage area was significantly less than pre-dose in animals treated with ACVP-1 or VID (Table 3). In the CID treated animals the leakage area was also significantly less than pre-dose (Table 3). Overall. ACVP-1 had better efficacy than VID and CID at inhibiting laser-induced CNV.

TABLE 3

Spot number and leakage area in monkey CNV model

| Group | Animal Number | Eye Number | Pre-dose Spot number | Pre-dose Leakage area (mm$^2$) | 14-day post dose Spot number | 14-day post dose Leakage area (mm$^2$) |
|---|---|---|---|---|---|---|
| PBS | 2 | 4 | 5.50 ± 2.65 | 10.7 ± 6.3 | 5.50 ± 2.65 | 12.3 ± 5.2 |
| ACVP-1 | 2 | 4 | 5.25 ± 2.63 | 12.9 ± 6.3 | 1.50 ± 1.29** | 0.5 ± 0.3** |
| VID | 2 | 4 | 5.00 ± 2.16 | 10.4 ± 4.1 | 2.00 ± 1.82* | 1.6 ± 0.7** |
| CID | 2 | 4 | 5.25 ± 1.71 | 11.4 ± 3.5 | 4.25 ± 1.50 | 6.5 ± 2.8* |

As compared to pre-dose,
*p < 0.05,
**p < 0.01

Example 14: Inhibition of Human Tumor Growth in Xenograft Mice by ACPs and ACVPs Various human cancer cells, such as human hepatocellular carcinoma Hep3B cells (ATCC# HB-8064) and human colorectal cancer LoVo cells (ATCC# CCL-229), can be used to establish xenograft models in nude mice. In order to assess the inhibitory effects of ACPs and ACVPs on tumor growth, various concentrations of each ACP and each ACVP (e.g., from 0.1-10 mg/kg) is administered twice weekly intravenously in the mice after tumor cell implantation. Tumor growth is measured weekly up to 7 weeks.

Example 15: Pharmacokinetic Assessment of ACPs and ACVPs in Mice and Monkeys A dosage of 10 to 40 mg/kg of each ACP and ACVP are administered into mice or monkeys via subcutaneous injection or intravenous injection. Serum samples are taken at different time points after the injection for up to 15 days. Concentrations of each ACP or ACVP fusion protein in the serum samples are determined using a sandwiched ELISA assay.

SEQUENCES

Human CR1 SCR1-3 nucleic acid and amino acid sequences

```
  1 caatgcaatg ccccagaatg gcttccattt gccaggccta ccaacctaac tgatgaattt
    Q  C  N    A  P  E   W  L  P  F   A  R  P    T  N  L    T  D  E  F
 61 gagtttccca ttgggacata tctgaactat gaatgccgcc ctggttattc cggaagaccg
    E  F  P    I  G  T   Y  L  N  Y  E  C  R    P  G  Y    S  G  R  P
121 ttttctatca tctgcctaaa aaactcagtc tggactggtg ctaaggacag gtgcagacgt
    F  S  I    I  C  L   K  N  S  V  W  T  G    A  K  D    R  C  R  R
181 aaatcatgtc gtaatcctcc agatcctgtg aatggcatgg tgcatgtgat caaaggcatc
    K  S  C    R  N  P   P  D  P  V  N  G  M    V  H  V    I  K  G  I
241 cagttcggat cccaaattaa atattcttgt actaaaggat accgactcat tggttcctcg
    Q  F  G    S  Q  I   K  Y  S  C  T  K  G    Y  R  L    I  G  S  S
301 tctgccacat gcatcatctc aggtgatact gtcatttggg ataatgaaac acctatttgt
    S  A  T    C  I  I   S  G  D  T  V  I  W    D  N  E    T  P  I  C
361 gacagaattc cttgtgggct accccccacc atcaccaatg gagatttcat tagcaccaac
    D  R  I    P  C  G   L  P  P  T  I  T  N    G  D  F    I  S  T  N
421 agagagaatt tcactatgg atcagtggtg acctaccgct gcaatcctgg aagcggaggg
    R  E  N    F  H  Y   G  S  V  V  T  Y  R    C  N  P    G  S  G  G
481 agaaaggtgt ttgagcttgt gggtgagccc tccatatact gcaccagcaa tgacgatcaa
    R  K  V    F  E  L   V  G  E  P  S  I  Y    C  T  S    N  D  D  Q
541 gtgggcatct ggagcggccc cgcccctcag tgcatt (SEQ ID NO: 17)
    V  G  I    W  S  G   P  A  P  Q  C  I  (SEQ ID NO: 1)
```

Human CR1 SCR1-3_N29K/D109N nucleic acid and amino acid sequences

```
  1 caatgcaatg ccccagaatg gcttccattt gccaggccta ccaacctaac tgatgaattt
    Q  C  N    A  P  E   W  L  P  F   A  R  P    T  N  L    T  D  E  F
 61 gagtttccca ttgggacata tctgaaatat gaatgccgcc ctggttattc cggaagaccg
    E  F  P    I  G  T   Y  L  K  Y  E  C  R    P  G  Y    S  G  R  P
121 ttttctatca tctgcctaaa aaactcagtc tggactggtg ctaaggacag gtgcagacgt
    F  S  I    I  C  L   K  N  S  V  W  T  G    A  K  D    R  C  R  R
181 aaatcatgtc gtaatcctcc agatcctgtg aatggcatgg tgcatgtgat caaaggcatc
    K  S  C    R  N  P   P  D  P  V  N  G  M    V  H  V    I  K  G  I
241 cagttcggat cccaaattaa atattcttgt actaaaggat accgactcat tggttcctcg
    Q  F  G    S  Q  I   K  Y  S  C  T  K  G    Y  R  L    I  G  S  S
301 tctgccacat gcatcatctc aggtaatact gtcatttggg ataatgaaac acctatttgt
    S  A  T    C  I  I   S  G  N  T  V  I  W    D  N  E    T  P  I  C
361 gacagaattc cttgtgggct accccccacc atcaccaatg gagatttcat tagcaccaac
    D  R  I    P  C  G   L  P  P  T  I  T  N    G  D  F    I  S  T  N
421 agagagaatt tcactatgg atcagtggtg acctaccgct gcaatcctgg aagcggaggg
    R  E  N    F  H  Y   G  S  V  V  T  Y  R    C  N  P    G  S  G  G
481 agaaaggtgt ttgagcttgt gggtgagccc tccatatact gcaccagcaa tgacgatcaa
    R  K  V    F  E  L   V  G  E  P  S  I  Y    C  T  S    N  D  D  Q
541 gtgggcatct ggagcggccc cgcccctcag tgcatt (SEQ ID NO: 18)
    V  G  I    W  S  G   P  A  P  Q  C  I  (SEQ ID NO: 2)
```

Human CR1 SCR1-3_S37Y/G79D nucleic acid and amino acid sequences

```
  1 caatgcaatg ccccagaatg gcttccattt gccaggccta ccaacctaac tgatgaattt
    Q  C  N    A  P  E   W  L  P  F   A  R  P    T  N  L    T  D  E  F
 61 gagtttccca ttgggacata tctgaactat gaatgccgcc ctggttatta cggaagaccg
    E  F  P    I  G  T   Y  L  N  Y  E  C  R    P  G  Y    S  G  R  P
121 ttttctatca tctgcctaaa aaactcagtc tggactggtg ctaaggacag gtgcagacgt
    F  S  I    I  C  L   K  N  S  V  W  T  G    A  K  D    R  C  R  R
181 aaatcatgtc gtaatcctcc agatcctgtg aatggcatgg tgcatgtgat caaagacatc
    K  S  C    R  N  P   P  D  P  V  N  G  M    V  H  V    I  K  D  I
241 cagttcggat cccaaattaa atattcttgt actaaaggat accgactcat tggttcctcg
    Q  F  G    S  Q  I   K  Y  S  C  T  K  G    Y  R  L    I  G  S  S
301 tctgccacat gcatcatctc aggtgatact gtcatttggg ataatgaaac acctatttgt
    S  A  T    C  I  I   S  G  D  T  V  I  W    D  N  E    T  P  I  C
361 gacagaattc cttgtgggct accccccacc atcaccaatg gagatttcat tagcaccaac
    D  R  I    P  C  G   L  P  P  T  I  T  N    G  D  F    I  S  T  N
421 agagagaatt tcactatgg atcagtggtg acctaccgct gcaatcctgg aagcggaggg
    R  E  N    F  H  Y   G  S  V  V  T  Y  R    C  N  P    G  S  G  G
481 agaaaggtgt ttgagcttgt gggtgagccc tccatatact gcaccagcaa tgacgatcaa
    R  K  V    F  E  L   V  G  E  P  S  I  Y    C  T  S    N  D  D  Q
541 gtgggcatct ggagcggccc cgcccctcag tgcatt (SEQ ID NO: 19)
    V  G  I    W  S  G   P  A  P  Q  C  I  (SEQ ID NO: 3)
```

Human CR1 SCR1-3_N29K/S37Y/G79D/D109N nucleic acid and amino acid sequences

```
  1 caatgcaatg ccccagaatg gcttccattt gccaggccta ccaacctaac tgatgaattt
    Q  C  N    A  P  E   W  L  P  F   A  R  P    T  N  L    T  D  E  F
 61 gagtttccca ttgggacata tctgaaatat gaatgccgcc ctggttatta cggaagaccg
    E  F  P    I  G  T   Y  L  K  Y  E  C  R    P  G  Y    S  G  R  P
121 ttttctatca tctgcctaaa aaactcagtc tggactggtg ctaaggacag gtgcagacgt
    F  S  I    I  C  L   K  N  S  V  W  T  G    A  K  D    R  C  R  R
181 aaatcatgtc gtaatcctcc agatcctgtg aatggcatgg tgcatgtgat caaagacatc
    K  S  C    R  N  P   P  D  P  V  N  G  M    V  H  V    I  K  D  I
241 cagttcggat cccaaattaa atattcttgt actaaaggat accgactcat tggttcctcg
    Q  F  G    S  Q  I   K  Y  S  C  T  K  G    Y  R  L    I  G  S  S
301 tctgccacat gcatcatctc aggtaatact gtcatttggg ataatgaaac acctatttgt
    S  A  T    C  I  I   S  G  N  T  V  I  W    D  N  E    T  P  I  C
```

| SEQUENCES |
|---|
| 361 gacagaattc cttgtgggct acccccccacc atcaccaatg agagtttcat tagcaccaac<br>     D  R  I    P  C  G    L  P  P    T  I  T  N    G  D  F    I  S  T  N<br>421 agagagaatt ttcactatgg atcagtggtg acctaccgct gcaatcctgg aagcggaggg<br>     R  E  N    F  H  Y    G  S  V  V    T  Y  R    C  N  P    G  S  G  G<br>481 agaaaggtgt ttgagcttgt gggtgagccc tccatatact gcaccagcaa tgacgatcaa<br>     R  K  V    F  E  L    V  G  E  P    S  I  Y    C  T  S    N  D  D  Q<br>541 gtgggcatct ggagcggccc cgcccctcag tgcatt (SEQ ID NO: 20)<br>     V  G  I    W  S  G    P  A  P  Q    C  I (SEQ ID NO: 4) |
| Human CR1 SCR8-10 nucleic acid and amino acid sequences<br>  1 cactgtcaag ccccagatca ttttctgttt gccaagttga aaacccaaac caatgcatct<br>     H  C  Q    A  P  D    H  F  L  F    A  K  L    K  T  Q    T  N  A  S<br> 61 gactttccca ttgggacatc tttaaagtac gaatgccgtc ctgagtacta cgggaggcca<br>     D  F  P    I  G  T    S  L  K  Y    E  C  R    P  E  Y    Y  G  R  P<br>121 ttctctatca catgtctaga taacctggtc tggtcaagtc ccaaagatgt ctgtaaacgt<br>     F  S  I    T  C  L    D  N  L  V    W  S  S    P  K  D    V  C  K  R<br>181 aaatcatgta aaactcctcc agatccagtg aatggcatgg tgcatgtgat cacagacatc<br>     K  S  C    K  T  P    P  D  P  V    N  G  M    V  H  V    I  T  D  I<br>241 caggttggat ccagaatcaa ctattcttgt actacagggc accgactcat tggtcactca<br>     Q  V  G    S  R  I    N  Y  S  C    T  T  G    H  R  L    I  G  H  S<br>301 tctgctgaat gtatcctctc gggcaatgct gcccattgga gcacgaagcc gccaatttgt<br>     S  A  E    C  I  L    S  G  N  A    A  H  W    S  T  K    P  I  C<br>361 caacgaattc cttgtgggct acccccccacc atcgccaatg agagtttcat tagcaccaac<br>     Q  R  I    P  C  G    L  P  P    T  I  A  N    G  D  F    I  S  T  N<br>421 agagagaatt ttcactatgg atcagtggtg acctaccgct gcaatcctgg aagcggaggg<br>     R  E  N    F  H  Y    G  S  V  V    T  Y  R    C  N  P    G  S  G  G<br>481 agaaaggtgt ttgagcttgt gggtgagccc tccatatact gcaccagcaa tgacgatcaa<br>     R  K  V    F  E  L    V  G  E  P    S  I  Y    C  T  S    N  D  D  Q<br>541 gtgggcatct ggagcggccc ggcccctcag tgcatt (SEQ ID NO: 21)<br>     V  G  I    W  S  G    P  A  P  Q    C  I (SEQ ID NO: 5) |
| Human CR1 SCR1-10 nucleic acid and amino acid sequences<br>  1 caatgcaatg ccccagaatg gcttccattt gccaggccta ccaacctaac tgatgaattt<br>     Q  C  N    A  P  E    W  L  P  F    A  R  P    T  N  L    T  D  E  F<br> 61 gagtttccca ttgggacata tctgaactat gaatgccgcc ctggttattc cggaagaccg<br>     E  F  P    I  G  T    Y  L  N  Y    E  C  R    P  G  Y    S  G  R  P<br>121 ttttctatca tctgcctaaa aaactcagtc tggactggtg ctaaggacag gtgcgacgt<br>     F  S  I    I  C  L    K  N  S  V    W  T  G    A  K  D    R  C  R  R<br>181 aaatcatgtc gtaatcctcc agatcctgtg aatggcatgg tgcatgtgat caaaggcatc<br>     K  S  C    R  N  P    P  D  P  V    N  G  M    V  H  V    I  K  G  I<br>241 cagttcggat cccaaattaa atattcttgt actaaaggat accgactcat tggttcctcg<br>     Q  F  G    S  Q  I    K  Y  S  C    T  K  G    Y  R  L    I  G  S  S<br>301 tctgccacat gcatcatctc aggtgatact gtcatttggg ataatgaaac acctatttgt<br>     S  A  T    C  I  I    S  G  D  T    V  I  W    D  N  E    T  P  I  C<br>361 gacagaattc cttgtgggct acccccccacc atcaccaatg agagtttcat tagcaccaac<br>     D  R  I    P  C  G    L  P  P    T  I  T  N    G  D  F    I  S  T  N<br>421 agagagaatt ttcactatgg atcagtggtg acctaccgct gcaatcctgg aagcggaggg<br>     R  E  N    F  H  Y    G  S  V  V    T  Y  R    C  N  P    G  S  G  G<br>481 agaaaggtgt ttgagcttgt gggtgagccc tccatatact gcaccagcaa tgacgatcaa<br>     R  K  V    F  E  L    V  G  E  P    S  I  Y    C  T  S    N  D  D  Q<br>541 gtgggcatct ggagcggccc cgcccctcag tgcattatac ctaacaaatg cacgcctcca<br>     V  G  I    W  S  G    P  A  P  Q    C  I  I    P  N  K    C  T  P  P<br>601 aatgtgaaaa atgaatatt ggtatctgac aacagaagct tatttttcctt aaatgaagtt<br>     N  V  E    N  G  I    L  V  S  D    N  R  S    L  F  S    L  N  E  V<br>661 gtggagttta ggtgtcagcc tggctttgtc atgaaaggac cccgccgtgt gaagtgccag<br>     V  E  F    R  C  Q    P  G  F  V    M  K  G    P  R  R    V  K  C  Q<br>721 gccctgaaca aatgggagcc ggagctacca agctgctcca gggtatgtca gccacctcca<br>     A  L  N    K  W  E    P  E  L  P    S  C  S    R  V  C    Q  P  P  P<br>781 gatgtcctgc atgctgagcg tacccaaagg gacaaggaca cttttcacc tgggcaggaa<br>     D  V  L    H  A  E    R  T  Q  R    D  K  D    N  F  S    P  G  Q  E<br>841 gtgttctaca gctgtgagcc cggctacgac ctcagagggg ctgcgtctat gcgctgcaca<br>     V  F  Y    S  C  E    P  G  Y  D    L  R  G    A  A  S    M  R  C  T<br>901 ccccagggag actggagccc tgcagccccc acatgtgaag tgaaatcctg tgatgacttc<br>     P  Q  G    D  W  S    P  A  A  P    T  C  E    V  K  S    C  D  D  F<br>961 atgggccaac ttcttaatgg ccgtgtgcta tttccagtaa atctccagct tggagcaaaa<br>     M  G  Q    L  L  N    G  R  V  L    F  P  V    N  L  Q    L  G  A  K<br>1021 gtggattttg tttgtgatga aggatttcaa ttaaaaggca gctctgctag ttactgtgtc<br>     V  D  F    V  C  D    E  G  F  Q    L  K  G    S  S  A    S  Y  C  V<br>1081 ttggctggaa tggaaagcct ttggaatagc agtgttccag tgtgtgaaca aatcttttgt<br>     L  A  G    M  E  S    L  W  N  S    S  V  P    V  C  E    Q  I  F  C<br>1141 ccaagtcctc cagttattcc taatgggaga cacacaggaa aacctctgga agtctttccc<br>     P  S  P    P  V  I    P  N  G  R    H  T  G    K  P  L    E  V  F  P<br>1201 tttgggaaaa cagtaaatta cacatgcgac ccccacccag acagagggac gagcttcgac<br>     F  G  K    T  V  N    Y  T  C  D    P  H  P    D  R  G    T  S  F  D<br>1261 ctcattggag agagcaccat ccgctgcaca agtgaccctc aagggaatgg ggtttggagc<br>     L  I  G    E  S  T    I  R  C  T    S  D  P    Q  G  N    G  V  W  S |

SEQUENCES

```
1321 agccctgccc ctcgctgtgg aattctgggt cactgtcaag ccccagatca ttttctgttt
      S   P   A   P   R   C   G   I   L   G   H   C   Q   A   P   D   H   F   L   F
1381 gccaagttga aacccaaac caatgcatct gactttccca ttgggacatc tttaaagtac
      A   K   L   K   T   Q   T   N   A   S   D   F   P   I   G   T   S   L   K   Y
1441 gaatgccgtc ctgagtacta cgggaggcca ttctctatca catgtctaga taacctggtc
      E   C   R   P   E   Y   Y   G   R   P   F   S   I   T   C   L   D   N   L   V
1501 tggtcaagtc ccaaagatgt ctgtaaacgt aaatcatgta aaactcctcc agatccagtg
      W   S   S   P   K   D   V   C   K   R   K   S   C   K   T   P   P   D   P   V
1561 aatggcatgg tgcatgtgat cacagacatc caggttggat ccagaatcaa ctattcttgt
      N   G   M   V   H   V   I   T   D   I   Q   V   G   S   R   I   N   Y   S   C
1621 actacagggc accgactcat tggtcactca tctgctgaat gtatcctctc gggcaatgct
      T   T   G   H   R   L   I   G   H   S   S   A   E   C   I   L   S   G   N   A
1681 gcccattgga gcacgaagcc gccaatttgt caacgaattc cttgtgggct accccccacc
      A   H   W   S   T   K   P   P   I   C   Q   R   I   P   C   G   L   P   P   T
1741 atcgccaatg gagatttcat tagcaccaac agagagaatt ttcactatgg atcagtggtg
      I   A   N   G   D   F   I   S   T   N   R   E   N   F   H   Y   G   S   V   V
1801 acctaccgct gcaatcctgg aagcggaggg agaaaggtgt ttgagcttgt gggtgagccc
      T   Y   R   C   N   P   G   S   G   G   R   K   V   F   E   L   V   G   E   P
1861 tccatatact gcaccagcaa tgacgatcaa gtgggcatct ggagcggccc ggcccctcag
      S   I   Y   C   T   S   N   D   D   Q   V   G   I   W   S   G   P   A   P   Q
1921 tgcatt (SEQ ID NO: 22)
      C   I (SEQ ID NO: 6)
```

Human IgG1 Fc nucleic acid and amino acid sequences

```
  1 gacaaaactc acacatgccc accgtgccca gcacctgaac tcctgggggg accgtcagtc
      D   K   T   H   T   C   P   P   C   P   A   P   E   L   L   G   G   P   S   V
 61 ttcctcttcc ccccaaaacc caaggacacc ctcatgatct cccggacccc tgaggtcaca
      F   L   F   P   P   K   P   K   D   T   L   M   I   S   R   T   P   E   V   T
121 tgcgtggtgg tggacgtgag ccacgaagac cctgaggtca agttcaactg gtacgtggac
      C   V   V   V   D   V   S   H   E   D   P   E   V   K   F   N   W   Y   V   D
181 ggcgtggagg tgcataatgc caagacaaag ccgcgggagg agcagtacaa cagcacgtac
      G   V   E   V   H   N   A   K   T   K   P   R   E   E   Q   Y   N   S   T   Y
241 cgtgtggtca gcgtcctcac cgtcctgcac caggactggc tgaatggcaa ggagtacaag
      R   V   V   S   V   L   T   V   L   H   Q   D   W   L   N   G   K   E   Y   K
301 tgcaaggtct ccaacaaagc cctcccagcc cccatcgaga aaaccatctc caaagccaaa
      C   K   V   S   N   K   A   L   P   A   P   I   E   K   T   I   S   K   A   K
361 gggcagcccc gagaaccaca ggtgtacacc ctgcccccat cccgggagga gatgaccaag
      G   Q   P   R   E   P   Q   V   Y   T   L   P   P   S   R   E   E   M   T   K
421 aaccaggtca gcctgacctg cctggtcaaa ggcttctatc ccagcgacat cgccgtggag
      N   Q   V   S   L   T   C   L   V   K   G   F   Y   P   S   D   I   A   V   E
481 tgggagagca atgggcagcc ggagaacaac tacaagacca cgcctcccgt gctggactcc
      W   E   S   N   G   Q   P   E   N   N   Y   K   T   T   P   P   V   L   D   S
541 gacggctcct tcttcctcta tagcaagctc accgtggaca agagcaggtg gcagcagggg
      D   G   S   F   F   L   Y   S   K   L   T   V   D   K   S   R   W   Q   Q   G
601 aacgtcttct catgctccgt gatgcatgag gctctgcaca accactacac gcagaagagc
      N   V   F   S   C   S   V   M   H   E   A   L   H   N   H   Y   T   Q   K   S
661 ctctccctgt ctccgggtaa a (SEQ ID NO: 23)
      L   S   L   S   P   G   K (SEQ ID NO: 7)
```

G6 nucleic acid and amino acid sequences

```
  1 ggaggtggag gcggtggt (SEQ ID NO: 24)
      G   G   G   G   G (SEQ ID NO: 8)
```

SP1 nucleic acid and amino acid sequences

```
  1 atggcctgga tgatgcttct cctcggactc cttgcttatg gatcaggagt cgactct (SEQ ID NO: 25)
      M   A   W   M   M   L   L   L   G   L   L   A   Y   G   S   G   V   D   S (SEQ ID NO: 9)
```

SP2 nucleic acid and amino acid sequences

```
  1 atggagacag acacactcct gctatgggta ctgctgctct gggttccagg gtcgactggc
      M   E   T   D   T   L   L   L   W   V   L   L   L   W   V   P   G   S   T   G
 61 gacact (SEQ ID NO: 26)
      D   T (SEQ ID NO: 10)
```

VEGFR-1_D2-VEGFR-2 D3 nucleic acid and amino acid sequences

```
  1 ggtagacctt tcgtagagat gtacagtgaa atccccgaaa ttatacacat gactgaagga
      G   R   P   F   V   E   M   Y   S   E   I   P   E   I   I   H   M   T   E   G
 61 agggagctcg tcattccctg ccgggttacg tcacctaaca tcactgttac ttttaaaaag
      R   E   L   V   I   P   C   R   V   T   S   P   N   I   T   V   T   L   K   K
121 tttccacttg acactttgat ccctgatgga aaacgcataa tctgggacag tagaaagggc
      F   P   L   D   T   L   I   P   D   G   K   R   I   I   W   D   S   R   K   G
181 ttcatcatat caaatgcaac gtacaaagaa ataggtcttc tgacctgtga agcaacagtc
      F   I   I   S   N   A   T   Y   K   E   I   G   L   L   T   C   E   A   T   V
241 aatgggcatt tgtataagac aaactatctc acacatcgac aaaccaatac aatcatagat
      N   G   H   L   Y   K   T   N   Y   L   T   H   R   Q   T   N   T   I   I   D
301 gtggttctga gtccgtctca tggaattgaa ctatctgttg gagaaaagct tgtcttaaat
      V   V   L   S   P   S   H   G   I   E   L   S   V   G   E   K   L   V   L   N
```

| SEQUENCES |
| --- |

```
 361 tgtacagcaa gaactgaact aaatgtgggg attgacttca actgggaata cccttcttcg
       C  T  A    R  T  E    L  N  V    G  I  D  F    N  W  E    Y  P  S  S
 421 aagcatcagc ataagaaact tgtaaaccga gacctaaaaa cccagtctgg gagtgagatg
       K  H  Q    H  K  K    L  V  N  R    D  L  K    T  Q  S    G  S  E  M
 481 aagaaatttt tgagcacctt aactatagat ggtgtaaccc ggagtgacca aggattgtac
       K  K  F    L  S  T    L  T  I  D    G  V  T    R  S  D    Q  G  L  Y
 541 acctgtgcag catccagtgg gctgatgacc aagaagaaca gcacatttgt cagggtccat
       T  C  A    A  S  S    G  L  M  T    K  K  N    S  T  F    V  R  V  H
 601 gaaaag (SEQ ID NO: 27)
       E  K (SEQ ID NO: 11)

ACVP-1 nucleic acid and amino acid sequences
    1 ggaagacctt ttgttgaaat gtattctgaa attcctgaaa ttattcatat gactgaagga
        G  R  P    F  V  E    M  Y  S  E    I  P  E    I  I  H    M  T  E  G
   61 agagaacttg ttattccttg tagagttact tctcctaata ttactgttac tcttaagaag
        R  E  L    V  I  P    C  R  V  T    S  P  N    I  T  V    T  L  K  K
  121 tttcctcttg atactcttat tcctgatgga aagagaatta tttgggattc tagaaaggga
        F  P  L    D  T  L    I  P  D  G    K  R  I    I  W  D    S  R  K  G
  181 tttattattt ctaatgctac ttataaggaa attggacttc ttacttgtga agctactgtt
        F  I  I    S  N  A  T    Y  K  E    I  G  L    L  T  C    E  A  T  V
  241 aatggacatc tttataagac taattatctt actcatagac aaactaatac catcatcgac
        N  G  H    L  Y  K    T  N  Y  L    T  H  R    Q  T  N    T  I  I  D
  301 gtggttctga gtccgtctca tggaattgaa ctatctgttg agaaaagct  tgtcttaaat
        V  V  L    S  P  S    H  G  I  E    L  S  V    E  K       L  V  L  N
  361 tgtacagcaa gaactgaact aaatgtgggg attgacttca actgggaata cccttcttcg
        C  T  A    R  T  E    L  N  V    G  I  D  F    N  W  E    Y  P  S  S
  421 aagcatcagc ataagaaact tgtaaaccga gacctaaaaa cccagtctgg gagtgagatg
        K  H  Q    H  K  K    L  V  N  R    D  L  K    T  Q  S    G  S  E  M
  481 aagaaattct tgagcaccct gactatagat ggtgtaaccc ggagtgacca aggattgtac
        K  K  F    L  S  T    L  T  I  D    G  V  T    R  S  D    Q  G  L  Y
  541 acctgtgcag catccagtgg gctgatgacc aagaagaaca gcacatttgt cagggtccat
        T  C  A    A  S  S    G  L  M  T    K  K  N    S  T  F    V  R  V  H
  601 gaaaagaca aaactcacac atgtccaccg tgtccagcac ctgaactcct gggtggaccg
        E  K  D    K  T  H    T  C  P  P    C  P  A    P  E  L    L  G  G  P
  661 tcagtcttcc tcttcccccc aaaacccaag gacaccctca tgatctcccg gacccctgag
        S  V  F    L  F  P    P  K  P  K    D  T  L    M  I  S    R  T  P  E
  721 gtcacatgcg tggtggtgga cgtgagccac gaagaccctg aggtcaagtt caactggtac
        V  T  C    V  V  V    D  V  S  H    E  D  P    E  V  K    F  N  W  Y
  781 gtggacggcg tggaggtgca taatgccaag acaaagccgc gggaggagca gtacaacagc
        V  D  G    V  E  V    H  N  A  K    T  K  P    R  E  E    Q  Y  N  S
  841 acgtaccgtg tggtcagcgt cctcaccgtc ctgcaccagg actggctgaa tggcaaggag
        T  Y  R    V  V  S    V  L  T  V    L  H  Q    D  W  L    N  G  K  E
  901 tacaagtgca aggtctccaa caaagccctc ccagccccca tcgagaaaac catctccaaa
        Y  K  C    K  V  S    N  K  A  L    P  A  P    I  E  K    T  I  S  K
  961 gccaaagggc agccccgaga accacaggtg tacaccctgc cccatcccg gatgagctg
        A  K  G    Q  P  R    E  P  Q  V    Y  T  L    P  P  S    R  D  E  L
 1021 accaagaacc aggtcagcct gacctgcctg gtcaaaggct tctatcccag cgacatcgcc
        T  K  N    Q  V  S    L  T  C    L  V  K  G    F  Y  P    S  D  I  A
 1081 gtggagtggg agagcaatgg gcagccggag aacaactaca agaccacgcc tcccgtgctg
        V  E  W    E  S  N    G  Q  P  E    N  N  Y    K  T  T    P  P  V  L
 1141 gactccgacg gctccttctt cctctacagc aagctcaccg tggacaagag caggtggcag
        D  S  D    G  S  F    F  L  Y  S    K  L  T    V  D  K    S  R  W  Q
 1201 caggggaacg tcttctcatg ctccgtgatg catgaggctc tgcacaacca ctacacgcag
        Q  G  N    V  F  S    C  S  V  M    H  E  A    L  H  N    H  Y  T  Q
 1261 aagagcctct ccctgtctcc gggtaaaggt ggaggaggcg tggtcaatg caatgccca
        K  S  L    S  L  S    P  G  K  G    G  G  G    G  Q    C  N  A  P
 1321 gaatggcttc catttgccag gcctaccaac ctaactgatg aatttgagtt tcccattggg
        E  W  L    P  F  A  R    P  T  N    L  T  D    E  F  E    F  P  I  G
 1381 acatatctga aatatgaatg ccgccctggt tattacggaa gaccgttttc tatcatctgc
        T  Y  L    K  Y  E    C  R  P  G    Y  Y  G    R  P  F    S  I  I  C
 1441 ctaaaaaact cagtctggac tggtgctaag gacaggtgca gactgtaaatc atgtcgtaat
        L  K  N    S  V  W    T  G  A  K    D  R  C    R  R  K    S  C  R  N
 1501 cctccagatc ctgtgaatgg catggtgcat gtgatcaaag acatccagtt cggatcccaa
        P  P  D    P  V  N    G  M  V  H    V  I  K    D  I  Q    F  G  S  Q
 1561 attaaatatt cttgtactaa aggataccga ctcattggtt cctcgtctgc acatgcatc
        I  K  Y    S  C  T    K  G  Y  R    L  I  G    S  S  S    A  T  C  I
 1621 atctcaggta atactgtcat ttgggataat gaaacaccta tttgtgacag aattccttgt
        I  S  G    N  T  V    I  W  D  N    E  T  P    I  C  D    R  I  P  C
 1681 gggctacccc ccaccatcac caatggagat ttcattagca ccaacagaga gaattttcac
        G  L  P    P  T  I    T  N  G  D    F  I  S    T  N  R    E  N  F  H
 1741 tatggatcag tggtgaccta ccgctgcaat cctggaagcg gagggagaaa ggtgtttgag
        Y  G  S    V  V  T    Y  R  C  N    P  G  S    G  G  R    K  V  F  E
 1801 cttgtgggtg agccctccat atactgcacc agcaatgacg atcaagtggg catctggagc
        L  V  G    E  P  S    I  Y  C  T    S  N  D    D  Q  V    G  I  W  S
 1861 ggccccgcac ctcagtgcat t (SEQ ID NO: 28)
        G  P  A    P  Q  C    I (SEQ ID NO: 12)
```

| SEQUENCES |
| --- |

DAF SCR2-4 nucleic acid and amino acid sequences
```
  1 cgtagctgcg aggtgccaac aaggctaaat tctgcatccc tcaaacagcc ttatatcact
    R   S   C   E   V   P   T   R   L   N   S   A   S   L   K   Q   P   Y   I   T
 61 cagaattatt ttccagtcgg tactgttgtg aatatgagt gccgtccagg ttacagaaga
    Q   N   Y   F   P   V   G   T   V   V   E   Y   E   C   R   P   G   Y   R   R
121 gaaccttctc tatcaccaaa actaacttgc cttcagaatt taaaatggtc cacagcagtc
    E   P   S   L   S   P   K   L   T   C   L   Q   N   L   K   W   S   T   A   V
181 gaattttgta aaagaaatc atgccctaat ccgggagaaa tacgaaatgg tcagattgat
    E   F   C   K   K   S   C   P   N   P   G   E   I   R   N   G   Q   I   D
241 gtaccaggtg gcatattatt tggtgcaacc atctccttct catgtaacac agggtacaaa
    V   P   G   G   I   L   F   G   A   T   I   S   F   S   C   N   T   G   Y   K
301 ttatttggct cgacttctag tttttgtctt atttcaggca gctctgtcca gtggagtgac
    L   F   G   S   T   S   S   F   C   L   I   S   G   S   S   V   Q   W   S   D
361 ccgttgccag agtgcagaga aatttattgt ccagcaccac acaaattga caatggaata
    P   L   P   E   C   R   E   I   Y   C   P   A   P   P   Q   I   D   N   G   I
421 attcaagggg aacgtgacca ttatggatat agacagtctg taacgtatgc atgtaataaa
    I   Q   G   E   R   D   H   Y   G   Y   R   Q   S   V   T   Y   A   C   N   K
481 ggattcacca tgattggaga gcactctatt tattgtactg tgaataatga tgaaggagag
    G   F   T   M   I   G   E   H   S   I   Y   C   T   V   N   N   D   E   G   E
541 tggagtggcc caccacctga atgcaga (SEQ ID NO: 29)
    W   S   G   P   P   P   E   C   R (SEQ ID NO: 13)
```

MCP SCR2-4 nucleic acid and amino acid sequences
```
  1 agagaaacat gtccatatat acgggatcct ttaaatggcc aagcagtccc tgcaaatggg
    R   E   T   C   P   Y   I   R   D   P   L   N   G   Q   A   V   P   A   N   G
 61 acttacgagt ttggttatca gatgcacttt atttgtaatg agggttatta cttaattggt
    T   Y   E   F   G   Y   Q   M   H   F   I   C   N   E   G   Y   Y   L   I   G
121 gaagaaattc tatattgtga acttaaagga tcagtagcaa tttggagcgg taagccccca
    E   E   I   L   Y   C   E   L   K   G   S   V   A   I   W   S   G   K   P   P
181 atatgtgaaa aggttttgtg tacaccacct ccaaaaataa aaaatggaaa acacaccttt
    I   C   E   K   V   L   C   T   P   P   P   K   I   K   N   G   K   H   T   F
241 agtgaagtag aagtatttga gtatcttgat gcagtaactt atagttgtga tcctgcacct
    S   E   V   E   V   F   E   Y   L   D   A   V   T   Y   S   C   D   P   A   P
301 ggaccagatc cattttcact tattggagag agcacgattt attgtggtga caattcagtg
    G   P   D   P   F   S   L   I   G   E   S   T   I   Y   C   G   D   N   S   V
361 tggagtcgtg ctgctccaga gtgtaaagtg gtcaaatgtc gatttccagt agtgtagaaat
    W   S   R   A   A   P   E   C   K   V   V   K   C   R   F   P   V   V   E   N
421 ggaaaacaga tatcaggatt tggaaaaaaa ttttactaca aagcaacagt tatgtttgaa
    G   K   Q   I   S   G   F   G   K   K   F   Y   Y   K   A   T   V   M   F   E
481 tgcgataagg gtttttacct cgatggcagc gacacaattg tctgtgacag taacagtact
    C   D   K   G   F   Y   L   D   G   S   D   T   I   V   C   D   S   N   S   T
541 tgggatcccc cagttccaaa gtgtctt (SEQ ID NO: 30)
    W   D   P   P   V   P   K   C   L (SEQ ID NO: 14)
```

Factor H SCR1-4 nucleic acid and amino acid sequences
```
  1 gaagattgca atgaacttcc tccaagaaga aatacagaaa ttctgacagg ttcctggtct
    E   D   C   N   E   L   P   P   R   R   N   T   E   I   L   T   G   S   W   S
 61 gaccaaacat atccagaagg cacccaggct atctataaat gccgccctgg atatagatct
    D   Q   T   Y   P   E   G   T   Q   A   I   Y   K   C   R   P   G   Y   R   S
121 cttggaaatg taataatggt atgcaggaag ggagaatggg ttgctcttaa tccattaagg
    L   G   N   V   I   M   V   C   R   K   G   E   W   V   A   L   N   P   L   R
181 aaatgtcaga aaaggccctg tggacatcct ggagatactc cttttggtac ttttaccctt
    K   C   Q   K   R   P   C   G   H   P   G   D   T   P   F   G   T   F   T   L
241 acaggaggaa atgtgtttga atatggtgta aaagctgtgt atacatgtaa tgaggggtat
    T   G   G   N   V   F   E   Y   G   V   K   A   V   Y   T   C   N   E   G   Y
301 caattgctag gtgagattaa ttaccgtgaa tgtgacacag atggatggac caatgatatt
    Q   L   L   G   E   I   N   Y   R   E   C   D   G   W   T   N   D   I
361 cctatatgtg aagttgtgaa gtgtttacca gtgacagcac cagagaatgg aaaaattgtc
    P   I   C   E   V   V   K   C   L   P   V   T   A   P   E   N   G   K   I   V
421 agtagtgcaa tggaaccaga tcgggaatac catttttggac aagcagtacg gtttgtatgt
    S   S   A   M   E   P   D   R   E   Y   H   F   G   Q   A   V   R   F   V   C
481 aactcaggct acaagattga aggagatgaa gaaatgcatt gttcagacga tggttttttgg
    N   S   G   Y   K   I   E   G   D   E   M   H   C   S   D   D   G   F   W
541 agtaaagaga aaccaaagtg tgtggaaatt tcatgcaaat ccccagatgt tataaatgga
    S   K   E   K   P   K   C   V   E   I   S   C   K   S   P   D   V   I   N   G
601 tctcctatat ctcagaagat tatttataag gagaatgaac gatttcaata taaatgtaac
    S   P   I   S   Q   K   I   I   Y   K   E   N   E   R   F   Q   Y   K   C   N
661 atgggttatg aatacagtga aagaggagat gctgtatgca ctgaatctgg atggcgtccg
    M   G   Y   E   Y   S   E   R   G   D   A   V   C   T   E   S   G   W   R   P
721 ttgccttcat gtgaa (SEQ ID NO: 31)
    L   P   S   C   E (SEQ ID NO: 15)
```

C4BPA SCR1-3 nucleic acid and amino acid sequences
```
  1 aattgtggtc ctccacccac tttatcattt gctgccccga tggatattac gttgactgag
    N   C   G   P   P   P   T   L   S   F   A   A   P   M   D   I   T   L   T   E
 61 acacgcttca aaactggaac tactctgaaa tacacctgcc tccctggcta cgtcagatcc
    T   R   F   K   T   G   T   T   L   K   Y   T   C   L   P   G   Y   V   R   S
```

-continued

SEQUENCES

```
121 cattcaactc agacgcttac ctgtaattct gatggcgaat gggtgtataa cacttctgt
      H  S  T    Q  L     T  C  N  S    D  G  E    W  V  Y     N  T  F  C
181 atctacaaac gatgcagaca cccaggagag ttacgtaatg ggcaagtaga gattaagaca
      I  Y  K    R  C  R    P  G  E     L  R  N    G  Q  V     E  I  K  T
241 gatttatctt ttggatcaca aatagaattc agctgttcag aaggattttt cttaattggc
      D  L  S    F  G  S    Q  I  E  F    S  C  S    E  G  F    L  I  G
301 tcaaccacta gtcgttgtga agtccaagat agaggagttg gctggagtca tcctctccca
      S  T  T    S  R  C    E  V  Q  D    R  G  V    G  W  S    H  P  L  P
361 caatgtgaaa ttgtcaagtg taagcctcct ccagacatca ggaatggaag gcacagcggt
      Q  C  E   I  V  K    C  K  P  P    P  D  I  R    N  G    R  H  S  G
421 gaagaaaatt tctacgcata cggctttttct gtcacctaca gctgtgaccc ccgcttctca
      E  E  N    F  Y  A    Y  G  F  S    V  T  Y     S  C  D    P  R  F  S
481 ctcttgggcc atgcctccat ttcttgcact gtggagaatg aaacaatagg tgtttggaga
      L  L  G    H  A  S    I  S  C  T    V  E  N     E  T  I    G  V  W  R
541 ccaagccctc ctacctgtga a (SEQ ID NO: 32)
      P  S  P    P  T  C    E  (SEQ ID NO: 16)
```

ACVP-2 amino acid sequence
QCNAPEWLPFARPTNLTDEFEFPIGTYLKYECRPGYYGRPFSIICLKNSVWTGAKDRC
RRKSCRNPPDPVNGMVHVIKDIQFGSQIKYSCTKGYRLIGSSSATCIISGNTVIWDNET
PICDRIPCGLPPTITNGDFISTNRENFHYGSVVTYRCNPGSGGRKVFELVGEPSIYCTSN
DDQVGIWSGPAPQCIGGGGGGDKTHTCPPCPAPELLGGPSVFLFPPKPKDTLMISRTP
EVTCVVVDVSHEDPEVKFNWYVDGVEVHNAKTKPREEQYNSTYRVVSVLTVLHQD
WLNGKEYKCKVSNKALPAPIEKTISKAKGQPREPQVYTLPPSREEMTKNQVSLTCLV
KGFYPSDIAVEWESNGQPENNYKTTPPVLDSDGSFFLYSKLTVDKSRWQQGNVFSCS
VMHEALHNHYTQKSLSLSPGKGGGGGGGGGRPFVEMYSEIPEIIHMTEGRELVIPCRVTS
PNITVTLKKFPLDTLIPDGKRIIWDSRKGFIISNATYKEIGLLTCEATVNGHLYKTNYLT
HRQTNTIIDVVLSPSHGIELSVGEKLVLNCTARTELNVGIDFNWEYPSSKHQHKKLVN
RDLKTQSGSEMKKFLSTLTIDGVTRSDQGLYTCAASSGLMTKKNSTFVRVHEK
(SEQ ID NO: 33)

ACVP-3 amino acid sequence
QCNAPEWLPFARPTNLTDEFEFPIGTYLKYECRPGYYGRPFSIICLKNSVWTGAKDRC
RRKSCRNPPDPVNGMVHVIKDIQFGSQIKYSCTKGYRLIGSSSATCIISGNTVIWDNET
PICDRIPCGLPPTITNGDFISTNRENFHYGSVVTYRCNPGSGGRKVFELVGEPSIYCTSN
DDQVGIWSGPAPQCIGGGGGGGRPFVEMYSEIPEIIHMTEGRELVIPCRVTSPNITVTL
KKFPLDTLIPDGKRIIWDSRKGFIISNATYKEIGLLTCEATVNGHLYKTNYLTHRQTNT
IIDVVLSPSHGIELSVGEKLVLNCTARTELNVGIDFNWEYPSSKHQHKKLVNRDLKTQ
SGSEMKKFLSTLTIDGVTRSDQGLYTCAASSGLMTKKNSTFVRVHEKDKTHTCPPCP
APELLGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQP
REPQVYTLPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPGK (SEQ ID NO: 34)

ACVP-4 amino acid sequence
GRPFVEMYSEIPEIIHMTEGRELVIPCRVTSPNITVTLKKFPLDTLIPDGKRIIWDSRKG
FIISNATYKEIGLLTCEATVNGHLYKTNYLTHRQTNTIIDVVLSPSHGIELSVGEKLVL
NCTARTELNVGIDFNWEYPSSKHQHKKLVNRDLKTQSGSEMKKFLSTLTIDGVTRSD
QGLYTCAASSGLMTKKNSTFVRVHEKGGGGGGQCNAPEWLPFARPTNLTDEFEFPI
GTYLKYECRPGYYGRPFSIICLKNSVWTGAKDRCRRKSCRNPPDPVNGMVHVIKDIQ
FGSQIKYSCTKGYRLIGSSSATCIISGNTVIWDNETPICDRIPCGLPPTITNGDFISTNRE
NFHYGSVVTYRCNPGSGGRKVFELVGEPSIYCTSNDDQVGIWSGPAPQCIGGGGGGD
KTHTCPPCPAPELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALPAPIEK
TISKAKGQPREPQVYTLPPSREEMTKNQVSLTCLVKGFYPSDIAVEWESNGQPENNY
KTTPPVLDSDGSFFLYSKLTVDKSRWQQGNVFSCSVMHEALHNHYTQKSLSLSPG
(SEQ ID NO: 35)

ACVP-5 amino acid sequence
DKTHTCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALPAPIE
KTISKAKGQPREPQVYTLPPSREEMTKNQVSLTCLVKGFYPSDIAVEWESNGQPENN
YKTTPPVLDSDGSFFLYSKLTVDKSRWQQGNVFSCSVMHEALHNHYTQKSLSLSPG
GGGGGGGRPFVEMYSEIPEIIHMTEGRELVIPCRVTSPNITVTLKKFPLDTLIPDGKRII
WDSRKGFIISNATYKEIGLLTCEATVNGHLYKTNYLTHRQTNTIIDVVLSPSHGIELSV
GEKLVLNCTARTELNVGIDFNWEYPSSKHQHKKLVNRDLKTQSGSEMKKFLSTLTID
GVTRSDQGLYTCAASSGLMTKKNSTFVRVHEKGGGGGGQCNAPEWLPFARPTNLT
DEFEFPIGTYLKYECRPGYYGRPFSIICLKNSVWTGAKDRCRRKSCRNPPDPVNGMV
HVIKDIQFGSQIKYSCTKGYRLIGSSSATCIISGNTVIWDNETPICDRIPCGLPPTITNGD
FISTNRENFHYGSVVTYRCNPGSGGRKVFELVGEPSIYCTSNDDQVGIWSGPAPQCI
(SEQ ID NO: 36)

ACVP-6 amino acid sequence
DKTHTCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALPAPIE
KTISKAKGQPREPQVYTLPPSREEMTKNQVSLTCLVKGFYPSDIAVEWESNGQPENN
YKTTPPVLDSDGSFFLYSKLTVDKSRWQQGNVFSCSVMHEALHNHYTQKSLSLSPG

| SEQUENCES |
| --- |
| GGGGGGQCNAPEWLPFARPTNLTDEFEFPIGTYLKYECRPGYYGRPFSIICLKNSVWT<br>GAKDRCRRKSCRNPPDPVNGMVHVIKDIQFGSQIKYSCTKGYRLIGSSSATCIISGNT<br>VIWDNETPICDRIPCGLPPTITNGDFISTNRENFHYGSVVTYRCNPGSGGRKVFELVGE<br>PSIYCTSNDDQVGIWSGPAPQCIGGGGGGGRPFVEMYSEIPEIIHMTEGRELVIPCRVT<br>SPNITVTLKKFPLDTLIPDGKRIIWDSRKGFIISNATYKEIGLLTCEATVNGHLYKTNYL<br>THRQTNTIIDVVLSPSHGIELSVGEKLVLNCTARTELNVGIDFNWEYPSSKHQHKKLV<br>NRDLKTQSGSEMKKFLSTLTIDGVTRSDQGLYTCAASSGLMTKKNSTFVRVHEK<br>(SEQ ID NO: 37)<br><br>VEGFR-1_D2-VEGFR-2_D3 amino acid sequence<br>DTGRPFVEMYSEIPEIIHMTEGRELVIPCRVTSPNITVTLKKFPLDTLIPDGKRIIWDSR<br>KGFIISNATYKEIGLLTCEATVNGHLYKTNYLTHRQTNTIIDVVLSPSHGIELSVGEKL<br>VLNCTARTELNVGIDFNWEYPSSKHQHKKLVNRDLKTQSGSEMKKFLSTLTIDGVTR<br>SDQGLYTCAASSGLMTKKNSTFVRVHEK (SEQ ID NO: 38)<br><br>Human IgG1 Fc amino acid sequence<br>DKTHTCPPCPAPELLGGPSVFLFPPKPKDTLMISRTPEVTCVVVDVSHEDPEVKFNWY<br>VDGVEVHNAKTKPREEQYNSTYRVVSVLTVLHQDWLNGKEYKCKVSNKALPAPIE<br>KTISKAKGQPREPQVYTLPPSRDELTKNQVSLTCLVKGFYPSDIAVEWESNGQPENN<br>YKTTPPVLDSDGSFFLYSKLTVDKSRWQQGNVFSCSVMHEALHNHYTQKSLSLSPGK<br>(SEQ ID NO: 39)<br><br>ACVP-1' amino acid sequence<br>DTGRPFVEMYSEIPEIIHMTEGRELVIPCRVTSPNITVTLKKFPLDTLIPDGKRIIWDSR<br>KGFIISNATYKEIGLLTCEATVNGHLYKTNYLTHRQTNTIIDVVLSPSHGIELSVGEKL<br>VLNCTARTELNVGIDFNWEYPSSKHQHKKLVNRDLKTQSGSEMKKFLSTLTIDGVTR<br>SDQGLYTCAASSGLMTKKNSTFVRVHEKDKTHTCPPCPAPELLGGPSVFLFPPKPKD<br>TLMISRTPEVTCVVVDVSHEDPEVKFNWYVDGVEVHNAKTKPREEQYNSTYRVVSV<br>LTVLHQDWLNGKEYKCKVSNKALPAPIEKTISKAKGQPREPQVYTLPPSRDELTKNQ<br>VSLTCLVKGFYPSDIAVEWESNGQPENNYKTTPPVLDSDGSFFLYSKLTVDKSRWQQ<br>GNVFSCSVMHEALHNHYTQKSLSLSPGKGGGGGGQCNAPEWLPFARPTNLTDEFEF<br>PIGTYLKYECRPGYYGRPFSIICLKNSVWTGAKDRCRRKSCRNPPDPVNGMVHVIKDI<br>QFGSQIKYSCTKGYRLIGSSSATCIISGNTVIWDNETPICDRIPCGLPPTITNGDFISTNR<br>ENFHYGSVVTYRCNPGSGGRKVFELVGEPSIYCTSNDDQVGIWSGPAPQCI (SEQ ID NO: 40)<br><br>Human IgG1 Fc amino acid sequence<br>DKTHTCPPCPAPELLGGPSVFLFPPKPKDTLMISRTPEVTCVVVDVSHEDPEVQFNWY<br>VDGVEVHNAKTKPREEQFNSTFRVVSVLTVVHQDWLNGKEYKCKVSNKALPAPIEK<br>TISKTKGQPREPQVYTLPPSREEMTKNQVSLTCLVKGFYPSDIAVEWESNGQPENNY<br>KTTPPMLDSDGSFFLYSKLTVDKSRWQQGNVFSCSVMHEALHNHYTQKSLSLSPGK<br>(SEQ ID NO: 41)<br><br>Human IgG1 Fc amino acid sequence<br>DKTHTCPPCPAPELLGGPSVFLFPPKPKDTLMISRTPEVTCVVVDVSHEDPEVKFNWY<br>VDGVEVHNAKTKPREEQYNSTYRVVSVLTVLHQDWLNGKDYKCKVSNKALPAPM<br>QKTISKAKGQPREPQVYTLPPSRDELTKNQVSLTCLVKGFYPRHIAVEWESNGQPEN<br>NYKTTPPVLDSDGSFFLYSKLTVDKSRWQQGNVFSCSVMHEALHNHYTQKSLSLSP<br>GK (SEQ ID NO: 42)<br><br>SP2 amino acid sequence<br>METDTLLLWVLLLWVPGSTG (SEQ ID NO: 43) |

What is claimed is:

1. A fusion protein comprising a complement inhibiting domain (CID), a VEGF inhibiting domain (VID), and a half-life prolonging domain, wherein the fusion protein inhibits complement activation and VEGF activity, wherein the CID comprises an amino acid sequence selected from the group consisting of SEQ ID NO:1-4, or an amino acid sequence having at least 98% identity to an amino acid sequence selected from the group consisting of SEQ ID NO:1-4, and wherein the VID comprises the amino acid sequence of SEQ ID NO:11 or 38, or an amino acid sequence having at least 98% identity to the amino acid sequence of SEQ ID NO:11 or 38.

2. The fusion protein of claim 1, wherein the CID comprises an amino acid sequence selected from the group consisting of SEQ ID NO:1-4.

3. The fusion protein of claim 1, wherein the VID comprises the amino acid sequence of SEQ ID NO:11 or 38.

4. The fusion protein of claim 1, wherein the half-life prolonging domain comprises an immunoglobulin Fc region.

5. The fusion protein of claim 4, wherein the Fc region is a human Fc of IgG1, IgG2, IgG3, or IgG4.

6. The fusion protein of claim 4, wherein the Fc region comprises the amino acid sequence of SEQ ID NO:7 or 39, or an amino acid sequence having at least 90% identity to the amino acid sequence of SEQ ID NO:7 or 39.

7. The fusion protein of claim 1, where the fusion protein further comprises a peptide linker between domains.

8. The fusion protein of claim 7, wherein the peptide linker comprises the amino acid sequence of SEQ ID NO:8.

9. The fusion protein of claim 4, wherein the fusion protein comprises said VID, CID, and Fc from N-terminal to C-terminal in an order selected from the group consisting of (1) VID, Fc, CID; (2) CID, Fc, VID; (3) CID, VID, Fc; (4) VID, CID, Fc; (5) Fc, VID, CID; and (6) Fc, CID, VID.

10. A fusion protein comprising, from the N-terminal to C-terminal, a VEGF inhibiting domain (VID), an immunoglobulin Fc region, and a complement inhibiting domain (CID), wherein the fusion protein inhibits complement activation and VEGF activity, wherein the CID comprises an amino acid sequence selected from the group consisting of SEQ ID NO:1-4, or an amino acid sequence having at least 98% identity to an amino acid sequence selected from the group consisting of SEQ ID NO:1-4, and wherein the VID comprises the amino acid sequence of SEQ ID NO:11 or 38, or an amino acid sequence having at least 98% identity to the amino acid sequence of SEQ ID NO:11 or 38.

11. The fusion protein of claim 10, wherein the CID comprises an amino acid sequence selected from the group consisting of SEQ ID NO:1-4.

12. The fusion protein of claim 10, wherein the VID comprises the amino acid sequence of SEQ ID NO:11 or 38.

13. The fusion protein of claim 10, wherein the Fc region is a human Fc of IgG1, IgG2, IgG3 or IgG4.

14. The fusion protein of claim 13, wherein the Fc region comprises the sequence of SEQ ID NO:7 or 39, or an amino acid sequence having at least 90% identity to the amino acid sequence of SEQ ID NO:7 or 39.

15. The fusion protein of claim 10, where the fusion protein further comprises a peptide linker between domains.

16. The fusion protein of claim 15, wherein the peptide linker is between the Fc region and the CID.

17. The fusion protein of claim 15, wherein the peptide linker comprises the amino acid sequence of SEQ ID NO:8.

18. The fusion protein of claim 10, wherein the fusion protein comprises the amino acid sequence of SEQ ID NO:12 or 40, or an amino acid sequence having at least 98% identity to the amino acid sequence of SEQ ID NO:12 or 40.

19. A fusion protein produced by culturing a host cell comprising a nucleic acid encoding the fusion protein of claim 1 under a condition that produces the fusion protein, and recovering the fusion protein produced by the host cell.

20. A dimeric fusion protein comprising two fusion proteins, wherein each fusion protein comprises the fusion protein of claim 10.

21. A composition comprising the fusion protein of claim 1 and a pharmaceutically acceptable carrier.

22. The composition of claim 21, wherein the fusion protein is a dimeric form.

23. A method of producing a fusion protein comprising culturing a host cell comprising a nucleic acid encoding the fusion protein of claim 1 under a condition that produces the fusion protein, and recovering the fusion protein produced by the host cell.

24. The method of claim 23, wherein the fusion protein is recovered from the cell culture medium and purified.

25. The method of claim 23, wherein the host cell is a mammalian cell or a yeast cell.

26. The method of claim 23, wherein the fusion protein recovered is a dimer.

27. A kit comprising the fusion protein of claim 1.

28. The kit of claim 27, further comprising a package insert comprising instructions for use the fusion protein for treating an inflammatory disease, an autoimmune disease, an ocular disease or cancer in a subject.

29. A composition comprising the fusion protein of claim 10 and a pharmaceutically acceptable carrier.

30. The composition of claim 29, wherein the fusion protein is a dimeric form.

31. The fusion protein of claim 10, wherein the fusion protein comprises the amino acid sequence of SEQ ID NO:12 or 40.

32. A fusion protein produced by culturing a host cell comprising a nucleic acid encoding a fusion protein comprising the amino acid sequence of SEQ ID NO:12 or 40 under a condition that produces the fusion protein, and recovering the fusion protein produced by the host cell.

33. A dimeric fusion protein comprising two fusion proteins, wherein each fusion protein comprises the amino acid sequence of SEQ ID NO:12 or 40.

34. A composition comprising the fusion protein of claim 31 and a pharmaceutically acceptable carrier.

35. The composition of claim 34, wherein the fusion protein is a dimeric form.

36. A method of producing a fusion protein comprising culturing a host cell comprising a nucleic acid encoding the amino acid sequence of SEQ ID NO:12 or 40 under a condition that produces the fusion protein, and recovering the fusion protein produced by the host cell.

37. The method of claim 36, wherein the fusion protein is recovered from the cell culture medium and purified.

38. The method of claim 36, wherein the host cell is a mammalian cell or a yeast cell.

39. The method of claim 36, wherein the fusion protein recovered is a dimer.

40. A kit comprising the fusion protein of claim 31.

41. The kit of claim 40, further comprising a package insert comprising instructions for use the fusion protein for treating an inflammatory disease, an autoimmune disease, an ocular disease or cancer in a subject.

* * * * *

UNITED STATES PATENT AND TRADEMARK OFFICE
CERTIFICATE OF CORRECTION

PATENT NO. : 9,988,611 B2
APPLICATION NO. : 14/362109
DATED : June 5, 2018
INVENTOR(S) : Jeng-Horng Her and Huang-Tsu Chen Page 1 of 1

It is certified that error appears in the above-identified patent and that said Letters Patent is hereby corrected as shown below:

On the Title Page

Item (71) Applicants, please delete "Innovent Biologies, Inc." and add --Innovent Biologics, Inc.--

Signed and Sealed this
Twenty-eighth Day of August, 2018

Andrei Iancu
*Director of the United States Patent and Trademark Office*